(12) United States Patent
Kehler et al.

(10) Patent No.: US 7,384,957 B2
(45) Date of Patent: Jun. 10, 2008

(54) 3,4-DIHYDRO-1H-ISOQUINOLIN-2-YL-DERIVATIVES

(75) Inventors: Jan Kehler, Kgs. Lyngby (DK); Anders Poulsen, Copenhagen (DK); Berith Bjornholm, Vaerlose (DK); Friedrich Kroll, Valby (DK); Morten Bang Norgaard, Lyngby (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 374 days.

(21) Appl. No.: 10/499,880

(22) PCT Filed: Dec. 16, 2002

(86) PCT No.: PCT/DK02/00858

§ 371 (c)(1),
(2), (4) Date: Oct. 28, 2004

(87) PCT Pub. No.: WO03/051869

PCT Pub. Date: Jun. 26, 2003

(65) Prior Publication Data

US 2005/0070713 A1    Mar. 31, 2005

Related U.S. Application Data

(60) Provisional application No. 60/341,905, filed on Dec. 19, 2001.

(30) Foreign Application Priority Data

Dec. 19, 2001 (DK) ............................... 2001 01916

(51) Int. Cl.
*C07D 471/04* (2006.01)
*A61K 31/445* (2006.01)

(52) U.S. Cl. ................. 514/307; 514/255.05; 544/405; 546/148

(58) Field of Classification Search ................ 546/148; 514/307, 255.05; 544/405
See application file for complete search history.

(56) References Cited

U.S. PATENT DOCUMENTS 3,994,891 A   11/1976   Hughes et al.
6,465,483 B1  10/2002   Losel et al.

FOREIGN PATENT DOCUMENTS

DE    3827727 A1    2/1990
DE    4104257    *   8/1992
WO    WO 97/17344 A1    5/1997

OTHER PUBLICATIONS

Hromatka et al, Monatshefte fuer Chemie, vol. 97, No. 1, 1966, pp. 19-32.*
Griebel, G., et al., Neuroscience and Behavioral Reviews, (2001) vol. 25, p. 619-626.
Rupniak, N.M.J. et al., Neuropharmacology (2000) vol. 39, p. 1413-1421.
Walsh, D.M. et al., Psychopharmacology (1995) vol. 121, p. 186-191.

* cited by examiner

*Primary Examiner*—Zinna N. Davis
(74) *Attorney, Agent, or Firm*—Stephen G. Kalinchak; Margaret M. Buck

(57) ABSTRACT

The present invention relates to novel compounds of formula I wherein the variable groups are as defined in the claims or a pharmaceutically acceptable acid addition salt thereof. The compounds of the invention are NK2 antagonists.

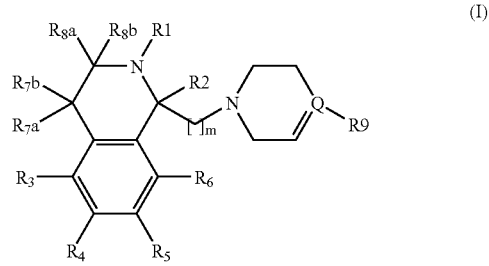

36 Claims, No Drawings

3,4-DIHYDRO-1H-ISOQUINOLIN-2-YL-DERIVATIVES

CROSS REFERENCE TO RELATED APPLICATIONS

The present application is the 371 national stage application of international application no. PCT/DK02/00858, filed Dec. 16, 2002, and claims the benefit of priority under 35 U.S.C. §119(e) of U.S. provisional application 60/341,905, filed Dec. 19, 2001, and the benefit of priority under 35 U.S.C. §119(a)-(d) of Danish application PA200101916, filed Dec. 19, 2001. All of the aforementioned applications are hereby incorporated herein by reference in their entireties.

FIELD OF THE INVENTION

The compounds of the present invention belong to a novel class of 3,4-dihydro-1H-isoquinolin-2-yl-derivatives having affinity for the neurokinin 2 (NK2) receptor. The compounds are NK2-antagonists and are useful in the treatment of those diseases where an NK2-receptor is implicated like asthma and a CNS-disease. These novel 3,4-dihydro-1H-isoquinolin-2-yl-derivatives are capable of penetrating the blood brain barrier and therefore useful in treating a variety of CNS diseases.

BACKGROUND OF THE INVENTION

Three tachykinins, Substance P (SP), neurokinin A (NKA) and neurokinin B (NKB) are widely distributed throughout the peripheral and central nervous systems. The biological effects of these neuropeptides are carried out via binding to their preferred receptors, NK1, NK2 and NK3 (Guard, S. and Watson, S. P. Neurochem. Int. 1991, 18, 149). Substance P displays highest affinity for the NK1 receptors, whereas NKA and NKB bind preferentially to NK2 and NK3 receptors, respectively. The selectivities of the endogenous ligands for their respective receptors are not absolute (reviewed in Regoli, D. et al. Pharmacol. Rev. 1994, 46, No. 4, 551 plus Bremer, A. A. et al. Eur J Pharmacol 2001, 423, 143). The three receptor subtypes belong to the G-protein-coupled receptor super family and have been cloned in various species including mice, rats and humans (Giardina, G. A. M. et al. Drugs of the Future 1997, 22, 1235 and references herein).

Activation of the tachykinin receptors influences a broad array of biological actions, including pain transmission, vasodilation, smooth muscle contraction, secretion of saliva, bronchoconstriction, activation of the immune system (inflammatory pain), neurogenic inflammation and neurotransmission (Patacchini, R. et Maggi, C. A. Eur J Pharmacol. 2001, 429, 13; Longmore, J. et al. Can J Physiol Pharmacol 1997, 75, 612; Giardina, G. A. M. et al. Drugs of the Future 1997, 22, 1235 and references herein).

Expression of NK2 receptors in human is somewhat controversial. The receptor is generally expressed in low amounts in CNS, and autoradiographic studies have failed to show NK2 receptors in the human brain. A recent reverse transcription-polymerase chain reaction (RT-PCR) study, however, has revealed a detectable expression of NK2 receptor mRNA in various human brain regions including caudate nucleus, putamen, hippocampus, substantia nigra and cerebral cortex (Bensaid, M et al. Neurosci Lett 2001, 303, 25).

Up-regulation of the preprotachykinin (PPT) genes and mRNAs for the neurokinin receptors occurs both in animal models of disease (Fischer, A. et al. J Clin Invest 1996, 98, 2284) and in human diseases, such as asthma (Adcock, I. M. et al. J Mol Endocrino 1993, 11, 1).

NK antagonists have been and are under investigations for the treatment of a vast amount of both CNS related and peripheral diseases. A number of pre-clinical studies have been performed to assess the involvement of NK1 and NK2 receptors mediation and modulation of diseases related to anxiety and/or depression (Griebel, G. Et al. Psychopharmacology, 2001, 158, 241; Walsh, D. M. et al. Psychopharmacology 1995, 121, 186; Rupniak, N. M. et al. Neuropharmacology 2000, 39, 1413; Rupniak, N. M. et Kramer, M. S. TiPS 1999, 20, 485; ; Giardina, G. A. M. et al. Drugs of the Future 1997, 22, 1235, and references in these).

These studies indicate that NK2 antagonists will be useful in treating or preventing a variety of brain disorders including depression, manic depression, bipolar disorder, dysthymia, mixed anxiety depression, generalised anxiety disorder, social anxiety disorder, panic anxiety disorder, post traumatic stress disorder, obsessive compulsive disorder, acute stress disorder, phobia, pre-menstrual dysphoric disorder, psychosis, and Huntington's disease as well as Parkinson's disease, adjustment disorders, pain, emesis, migraine, epilepsia, obesity, asthma and cerebrovascular disease. However, peripheral diseases such as inflammation, inflammatory bowel disease, hypertension, arthritis, cardiovascular diseases, neuritis, neuralgia, urticaria, incontinence, gastrointestinal diseases, influenza, allergy, pulmonary allergy and carcinoma/tumoral growth may also be addressed by NK2 antagonists.

U.S. Pat. No. 3,994,891 discloses tetrahydroisoquinolines of the general formula

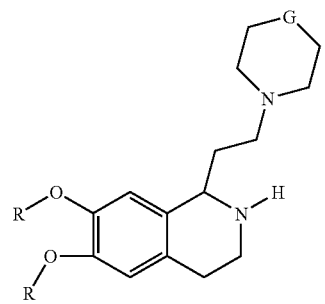

wherein R is hydrogen or methyl, and G is NH or CH$_2$. The dihydroxy compounds are described as effective vasodilators, whereas the dimethoxy compounds are intermediates in the manufacture of the dihydroxy compounds.

Hence, there is a desire for novel compounds that are antagonists at the NK2 receptor.

SUMMARY OF THE INVENTION

The objective of the present invention is to provide compounds that are antagonists at the NK2 receptor.

A further objective of the present invention is to provide compounds with such activities which have improved solubility, metabolic stability and/or bioavailability compared to prior art compounds.

Accordingly, the present invention relates to novel compounds of formula I

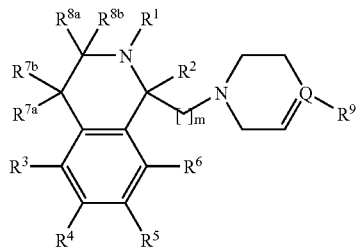

I wherein
R$^1$ is a group R$^{11}$CO—, R$^{11}$CS—, R$^{11}$SO$_2$—, R$^{11}$OCO—, R$^{11}$SCO— or R$^{11}$CO—CR$^{12}$R$^{13}$— wherein R$^{11}$ is C$_{1-12}$-alkyl, C$_{2-6}$-alkenyl, C$_{2-6}$-alkynyl, C$_{3-8}$-cycloalkyl, C$_{3-8}$-cycloalkyl-C$_{1-6}$-alkyl, aryl, aryl-C$_{1-6}$-alkyl, heteroaryl, heteroaryl-C$_{1-6}$-alkyl, tetrahydropyranyl, 1,2,3,4-tetrahydronaphtalenyl, or 4H-benzo[1,3]dioxinyl optionally substituted with halogen wherein each of said C$_{1-6}$-alkyl, aryl, heteroaryl and C$_{3-8}$-cycloalkyl groups independently are unsubstituted or substituted with one or more substituents selected from the group comprising halogen, C$_{1-6}$-alkyl, C$_{1-6}$-alkoxy, aryl-C$_{1-6}$-alkoxy, C$_{1-6}$-alkylsulfanyl, aryl and aryloxy wherein said aryl and aryloxy independently are unsubstituted or substituted with one or more halogen, and R$^{12}$ and R$^{13}$ independently are hydrogen or C$_{1-6}$-alkyl; or R$^1$ is a group R$^{14}$R$^{15}$NCO—, R$^{14}$R$^{15}$NCS—, wherein R$^{14}$ and R$^{15}$ are independently hydrogen, C$_{1-6}$-alkyl, C$_{2-6}$-alkenyl, C$_{2-6}$-alkynyl, C$_{3-8}$-cycloalkyl, C$_{3-8}$-cycloalkyl-C$_{1-6}$-alkyl, aryl or aryl-C$_{1-6}$-alkyl, wherein each of said C$_{1-6}$-alkyl, aryl and C$_{3-8}$-cycloalkyl groups independently are unsubstituted or substituted with one or more substituents selected from the group comprising halogen, C$_{1-6}$-alkyl and C$_{1-6}$-alkoxy, or R$^{14}$ and R$^{15}$ together with the N-atom to which they are linked, form a pyrrolidinyl, piperidinyl or perhydroazepinyl group;
R$^2$ is selected from hydrogen, trifluoromethyl and C$_{1-6}$-alkyl;
R$^3$-R$^6$, R$^{7a}$, R$^{7b}$, R$^{8a}$ and R$^{8b}$ are independently selected from hydrogen, halogen, cyano, nitro, C$_{1-6}$-alkyl, C$_{2-6}$-alkenyl, C$_{2-6}$-alkynyl, C$_{3-8}$-cycloalkyl, C$_{3-8}$-cycloalkyl-C$_{1-6}$-alkyl, amino, C$_{1-6}$-alkylamino, di-(C$_{1-6}$-alkyl)amino, C$_{1-6}$-alkylcarbonyl, aminocarbonyl, C$_{1-6}$-alkylaminocarbonyl, di-(C$_{1-6}$-alkyl)aminocarbonyl, C$_{1-4}$-alkoxy, C$_{1-6}$-alkylthio, hydroxy, trifluoromethyl, trifluoromethylsulfonyl and C$_{1-6}$-alkylsulfonyl;
m is 2-6;
R$^9$ is benzyl, benzoyl, 2,3-dihydrobenzofuranyl or mono- or bicyclic aryl or heteroaryl wherein each benzyl, benzoyl, aryl or heteroaryl optionally is substituted with one or more substituents selected from halogen, cyano, nitro, C$_{1-6}$-alkyl, C$_{2-6}$-alkenyl, C$_{2-6}$-alkynyl, C$_{3-8}$-cycloalkyl, C$_{3-8}$-cycloalkyl-C$_{1-6}$-alkyl, amino, C$_{1-6}$-alkylamino, di-(C$_{1-6}$-alkyl)amino, C$_{1-6}$-alkylcarbonyl, aminocarbonyl, C$_{1-6}$-alkylaminocarbonyl, di-(C$_{1-6}$-alkyl)aminocarbonyl, C$_{1-6}$-alkoxy, C$_{1-6}$-alkylthio, hydroxy, trifluoromethyl, difluoromethyl, fluoromethyl and trifluoromethylsulfonyl;
Q is C, N or CR$^{10}$;
wherein R$^{10}$ is selected from hydrogen, halogen, cyano, nitro, C$_{1-6}$-alkyl, C$_{2-6}$-alkenyl, C$_{2-6}$-alkynyl, C$_{3-8}$-cycloalkyl, C$_{3-8}$-cycloalkyl-C$_{1-6}$-alkyl, amino, C$_{1-6}$-alkylamino, di-(C$_{1-6}$-alkyl)amino, C$_{1-6}$-alkylcarbonyl, aminocarbonyl, C$_{1-6}$-alkylaminocarbonyl, di-(C$_{1-6}$-alkyl)aminocarbonyl, C$_{1-6}$-alkoxy, C$_{1-6}$-alkylthio, hydroxy, trifluoromethyl, difluoromethyl, fluoromethyl, trifluoromethylsulfonyl, a group —NR$^{30}$COR$^{31}$ wherein R$^{30}$ is hydrogen or C$_{1-6}$-alkyl and R$^{31}$ is C$_{1-6}$-alkyl, a group —COOR$^{16}$ wherein R$^{16}$ is hydrogen or C$_{1-6}$-alkyl, or a group —CONR$^{17}$R$^{18}$ wherein R$^{17}$ and R$^{18}$ independently are selected from hydrogen and C$_{1-6}$-alkyl or R$^{17}$ and R$^{18}$ together with the nitrogen to which they are attached form a piperidinyl, piperazinyl or morpholinyl, wherein said piperidinyl, piperazinyl and morpholinyl is unsubstituted or substituted with a C$_{1-6}$-alkyl;

or R$^9$ and R$^{10}$ together with the carbon to which they are attached form a cyclic structure selected from the group comprising:

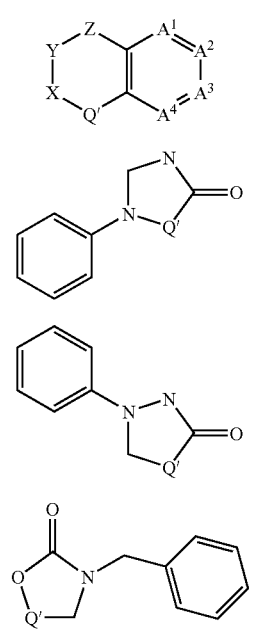

wherein Q' is the carbon shared with the piperidine ring, so that said cyclic structure together with said piperidine ring form a spiro structure; and X, Y, and Z are independently chosen from O; NR$^{19}$; CR$^{23}$R$^{24}$; S(O)$_n$ and a bond; wherein R$^{19}$ is selected from hydrogen, C$_{1-6}$-alkyl, C$_{2-6}$-alkenyl, C$_{2-6}$-alkynyl, C$_{3-8}$-cycloalkyl, C$_{3-8}$-cycloalkyl-C$_{1-6}$-alkyl, trifluoromethyl, acyl, thioacyl and trifluoromethylsulfonyl, or R$^{19}$ is a group R$^{20}$SO$_2$—, R$^{20}$OCO— or R$^{20}$SCO— wherein R$^{20}$ is C$_{1-6}$-alkyl, C$_{2-6}$-alkenyl, C$_{2-6}$-alkynyl, C$_{3-8}$-cycloalkyl, C$_{3-8}$-cycloalkyl-C$_{1-6}$-alkyl or aryl, or R$^{19}$ is a group R$^{21}$R$^{22}$NCO— or R$^{21}$R$^{22}$NCS—, wherein R$^{21}$ and R$^{22}$ are independently hydrogen, C$_{1-6}$-alkyl, C$_{2-6}$-alkenyl, C$_{2-6}$-alkynyl, C$_{3-8}$-cycloalkyl, C$_{3-8}$-cycloalkyl-C$_{1-6}$-alkyl, or aryl, wherein said aryl is unsubstituted or substituted with one or more substituents selected from C$_{1-6}$-alkyl or halogen; or R$^{21}$ and R$^{22}$ together with the N-atom to which they are linked, form a pyrrolidinyl, piperidinyl or perhydroazepinyl group; R$^{23}$ and R$^{24}$ are independently selected from hydrogen, halogen, cyano, nitro, C$_{1-6}$-alkyl, C$_{2-6}$-alkenyl, C$_{2-6}$-alkynyl, C$_{3-8}$-cycloalkyl, C$_{3-8}$-cycloalkyl-C$_{1-6}$-alkyl, aryl, heteroaryl, wherein said aryl is unsubstituted or substituted with one or more substituents selected from $C_{1-6}$-alkyl or halogen, amino, $C_{1-6}$-alkylamino, a group $NR^{25}R^{26}$ wherein $R^{25}$ and $R^{26}$ are independently selected from $C_{1-6}$-alkyl $C_{1-6}$-alkylcarbonyl, aminocarbonyl, $C_{1-6}$-alkylaminocarbonyl, di-($C_{1-6}$-alkyl)aminocarbonyl, $C_{1-6}$-alkoxy, $C_{1-6}$-alkylthio, hydroxy, trifluoromethyl, trifluoromethylsulfonyl and $C_{1-6}$-alkylsulfonyl or $R^{25}$ and $R^{26}$ together with the N-atom to which they are linked, form a pyrrolidinyl, piperidinyl, perhydroazepinyl or morpholinyl group, or $R^{23}$ and $R^{24}$ together is oxo; and n is 0, 1 or 2; provided that no more than one of X, Y and Z may be a bond, and provided that two adjacent groups X, Y or Z may not at the same time be selected from O and S; and $A^1$, $A^2$, $A^3$ and $A^4$ are independently selected from N and $CR^{27}$ wherein $R^{27}$ is hydrogen, halogen, cyano, nitro, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, $C_{1-6}$-alkylcarbonyl, aminocarbonyl, $C_{1-6}$-alkylaminocarbonyl, di-($C_{1-6}$-alkyl)aminocarbonyl, $C_{1-6}$-alkoxy, $C_{1-6}$-alkylthio, hydroxy, trifluoromethyl, difluoromethyl, fluoromethyl, trifluoromethylsulfonyl $C_{1-6}$-alkylsulfonyl amino or a group $NR^{28}R^{29}$ wherein $R^{28}$ and $R^{29}$ are independently selected from hydrogen and $C_{1-6}$-alkyl or $R^{28}$ and $R^{29}$ together with the N-atom to which they are linked, form a pyrrolidinyl, piperidinyl, perhydroazepinyl or morpholinyl group; provided that only one of $A^1$, $A^2$, $A^3$ and $A^4$ may be N; and the dotted line emanating from Q is a bond when Q is C, and no bond when Q is $CR^{10}$ or N;

or a pharmaceutically acceptable acid addition salt thereof

DETAILED DESCRIPTION OF THE INVENTION

The $C_{1-12}$-alkyl groups defined for $R^{11}$ are preferably selected from $C_{1-10}$-alkyl, more preferred $C_{1-8}$-alkyl, and most preferred $C_{3-8}$-alkyl.

In one embodiment, the present invention relates to such compounds wherein Q is $CR^{10}$, and $R^9$ and $R^{10}$ together with the carbon to which they are attached form a bicyclic structure:

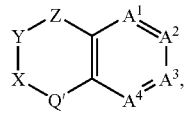

1)

wherein Q' is the carbon shared with the piperidine ring, so that said bicyclic structure together with said piperidine ring form a spiro structure; and X, Y and Z are independently chosen from O; $NR^{19}$; $CR^{23}R^{24}$ and $S(O)n$ wherein $R^{19}$ is selected from hydrogen, $C1_{-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, trifluoromethyl, acyl, thioacyl and trifluoromethylsulfonyl, or $R^{19}$ is a group $R^{20}SO_2$—, $R^{20}OCO$— or $R^{20}SCO$— wherein $R^{20}$ is $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl or aryl, or $R^{19}$ is a group $R^{21}R^{22}NCO$—, $R^{21}R^{22}NCS$—, wherein $R^{21}$ and $R^{22}$ are independently hydrogen, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl or aryl, wherein said aryl is unsubstituted or substituted with one or more substituents selected from $C_{1-6}$-alkyl or halogen; or $R^{21}$ and $R^{22}$ together with the N-atom to which they are linked, form a pyrrolidinyl, piperidinyl or perhydroazepinyl group; $R^{23}$ and $R^{24}$ are independently selected from hydrogen, halogen, cyano, nitro, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, aryl, heteroaryl, wherein said aryl is unsubstituted or substituted with one or more substituents selected from $C_{1-6}$-alkyl or halogen, amino, $C_{1-6}$-alkylamino, a group $NR^{25}R^{26}$ wherein $R^{25}$ and $R^{26}$ are independently selected from $C_{1-6}$-alkyl or $R^{25}$ and $R^{26}$ together with the N-atom to which they are linked, form a pyrrolidinyl, piperidinyl, perhydroazepinyl or morpholinyl group, $C^{1-6}$-alkylcarbonyl, aminocarbonyl, $C_{1-6}$-alkylaminocarbonyl, di-($C_{1-6}$-alkyl)aminocarbonyl, $C_{1-6}$-alkoxy, $C_{1-6}$-alkylthio, hydroxy, trifluoromethyl, trifluoromethylsulfonyl, and $C_{1-6}$-alkylsulfonyl or $R^{23}$ and $R^{24}$ together is oxo; and n is 0, 1 or 2; and a bond; provided that no more than one of X, Y and Z may be a bond, and provided that two adjacent groups X, Y or Z may not at the same time be selected from O and S; and $A^1$, $A^2$, $A^3$ and $A^4$ are independently selected from N and $CR^{27}$ wherein $R^{27}$ is hydrogen, halogen, cyano, nitro, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, amino, a group $NR^{28}R^{29}$ wherein $R^{28}$ and $R^{29}$ are independently selected from hydrogen and $C_{1-6}$-alkyl or $R^{28}$ and $R^{29}$ together with the N-atom to which they are linked, form a pyrrolidinyl, piperidinyl, perhydroazepinyl or morpholinyl group, $C_{1-6}$-alkylcarbonyl, aminocarbonyl, $C_{1-6}$-alkylaminocarbonyl, di-($C_{1-6}$alkyl)aminocarbonyl, $C_{1-6}$-alkoxy, $C_{1-6}$-alkylthio, hydroxy, trifluoromethyl, difluoromethyl, fluoromethyl, trifluoromethylsulfonyl or $C_{1-6}$-alkylsulfonyl; provided that only one of $A^1$, $A^2$, $A^3$ and $A^4$ may be N.

In a preferred embodiment, the present invention relates to such compounds wherein X, Y and Z are selected from one of the combinations: X is oxygen, Y is a bond and Z is $CR^{23}R^{24}$; X is $CR^{23}R^{24}$, Y is a bond and Z is oxygen; X is $NR^{19}$, Y is a bond and Z is $CR^{23}R^{24}$; X is $CR^{23}R^{24}$, Y is a bond and Z is $NR^{19}$; X is CO, Y is a bond and Z is $NR^{19}$; X is $SO_2$, Y is a bond and Z is $NR^{19}$; X is SO, Y is a bond and Z is $NR^{19}$; X is $CR^{23}R^{24}$, Y is a bond and Z is S; X is $CR^{23}R^{24}$, Y is a bond and Z is SO; X is $CR^{23}R^{24}$, Y is a bond and Z is $SO_2$; wherein $R^{19}$ is hydrogen, acetyl or methylsulfonyl and $R^{23}$ and $R^{24}$ are independently selected from hydrogen, methyl, isobutyl, cyclohexyl and 4-fluorophenyl.

In another preferred embodiment, the present invention relates to such compounds wherein —X—Y-Z- together form a group selected from: —O—$CR^{23}R^{24}$—, —$CR^{23}R^{24}$—O—, —$NR^{19}$—$CR^{23}R^{24}$—, —$CR^{23}R^{24}$—$NR^{19}$—, —CO—$NR^{19}$—, —$SO_2$—$NR^{19}$—, —SO—$NR^{19}$—, —$CR^{23}R^{24}$—S—, —$CR^{23}R^{24}$—SO—, —$CR^{23}R^{24}$—$SO_2$—; wherein $R^{19}$ is hydrogen, acetyl or methylsulfonyl tyl and $R^{23}$ and $R^{24}$ are independently selected from hydrogen, methyl, isobutyl, cyclohexyl and 4-fluorophenyl.

In another preferred embodiment, the present invention relates to such compounds wherein $A^3$ is N or $CR^{27}$ wherein $R^{27}$ is halogen, cyano, nitro, a group $NR^{28}R^{29}$ wherein $R^{28}$ and $R^{29}$ are independently selected from hydrogen and $C_{1-6}$-alkyl or $R^{28}$ and $R^{29}$ together with the N-atom to which they are linked, form a pyrrolidinyl, piperidinyl, perhydroazepinyl or morpholinyl group, $C_{1-6}$-alkylcarbonyl, aminocarbonyl, $C_{1-6}$-alkylaminocarbonyl, di-($C_{1-6}$-alkyl)aminocarbonyl, $C_{1-6}$-alkoxy, hydroxy, trifluoromethyl, difluoromethyl, fluoromethyl, trifluoromethylsulfonyl or $C_{1-6}$-alkylsulfonyl.

In another preferred embodiment, the present invention relates to such compounds wherein $A^1$, $A^2$, $A^3$ and $A^4$ are independently selected from $CR^{27}$ wherein $R^{27}$ is as defined above.

In a more preferred embodiment, the present invention relates to such compounds wherein bicyclic structure described above is selected from the group comprising:

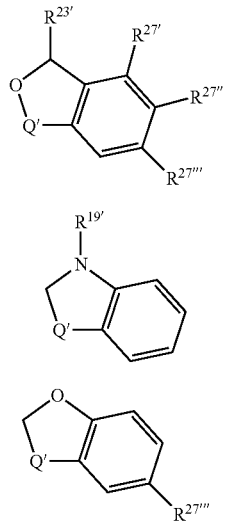

a)

b)

c)

wherein $R^{19'}$ is acetyl or methylsulfonyl, $R^{23'}$ is hydrogen or methyl, $R^{27'}$ is hydrogen or fluoro, $R^{27''}$ is hydrogen, fluoro, methyl or isopropyl, $R^{27'''}$ is hydrogen, fluoro or trifluoromethyl.

In another embodiment, the present invention relates to such compounds wherein $R^9$ and $R^{10}$ together with the carbon to which they are attached form a cyclic structure selected from the group comprising:

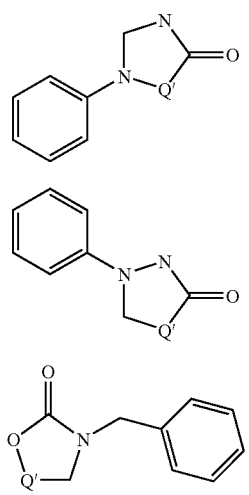

2)

3)

4)

wherein Q' is the carbon shared with the piperidine ring, so that said cyclic structure together with said piperidine ring form a spiro structure In yet another embodiment, the present invention relates to such compounds wherein $R^9$ is benzyl, benzoyl, 2,3-dihydrobenzofuran-7-yl or mono- or bicyclic aryl or heteroaryl wherein each benzyl, benzoyl, aryl or heteroaryl optionally is substituted with one or more substituents selected from halogen, cyano, nitro, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, amino, $C_{1-6}$-alkylamino, di-($C_{1-6}$-alkyl)amino, $C_{1-6}$-alkylcarbonyl, aminocarbonyl, $C_{1-6}$-alkylaminocarbonyl, di-($C_{1-6}$- alkyl)aminocarbonyl, $C_{1-6}$-alkoxy, $C_{1-6}$-alkylthio, hydroxy, trifluoromethyl, difluoromethyl, fluoromethyl and trifluoromethylsulfonyl.

In yet another embodiment, the present invention relates to such compounds wherein $R^9$ is 2,3-dihydrobenzofuran-7-yl, benzyl or benzoyl wherein said benzyl or benzoyl is unsubstituted or substituted with one or more halogens in the phenyl groups, or $R^9$ is mono- or bicyclic aryl or heteroaryl selected from the group comprising phenyl, indolyl, pyridyl, thiophenyl and benzisoxazolyl, wherein each aryl or heteroaryl optionally is substituted with one or more substituents selected from halogen, cyano, nitro, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$- alkyl, amino, $C_{1-6}$-alkylamino, di-($C_{1-6}$alkyl)amino, $C_{1-6}$-alkylcarbonyl, aminocarbonyl, $C_{1-6}$-alkylaminocarbonyl, di-($C_{1-6}$-alkyl)aminocarbonyl, $C_{1-6}$-alkoxy, $C_{1-6}$-alkylthio, hydroxy, trifluoromethyl, difluoromethyl, fluoromethyl and trifluoromethylsulfonyl.

In a preferred embodiment, the present invention relates to such compounds wherein said mono- or bicyclic aryl or heteroaryl is selected from the group comprising phenyl, indol-3-yl and benzisoxazol-3-yl wherein said phenyl, indol-3-yl or benzisoxazol-3-yl optionally is substituted with one or more substituents selected from halogen, cyano, nitro, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, amino, $C_{1-6}$-alkylamino, di-($C_{1-6}$- alkyl)amino, $C_{1-6}$-alkylcarbonyl, aminocarbonyl, $C_{1-6}$-alkylaminocarbonyl, di-($C1_{-6}$-alkyl)aminocarbonyl, $C_{1-6}$-alkoxy, $C_{1-6}$-alkylthio, hydroxy, trifluoromethyl, difluoromethyl, fluoromethyl and trifluoromethylsulfonyl.

In an even more preferred embodiment, the present invention relates to such compounds wherein said optional substituents are selected from the group comprising halogen, phenyl and methyl.

In yet another embodiment, the present invention relates to such compounds wherein Q is $CR^{10}$ wherein $R^{10}$ is selected from hydrogen, $C_{1-6}$-alkylcarbonyl, hydroxy, a group —$NR^{30}COR^{31}$ wherein $R^{30}$ is hydrogen or $C_{1-6}$-alkyl and $R^{31}$ is $C_{1-6}$-alkyl, a group —$COOR^{16}$ wherein $R^{16}$ is $C_{1-6}$-alkyl, or a group —$CONR^{17}R^{18}$ wherein $R^{17}$ and $R^{18}$ together with the nitrogen to which they are attached form a piperidinyl, piperazinyl or morpholinyl, wherein said piperidinyl, piperazinyl and morpholinyl are unsubstituted or substituted with a $C_{1-6}$-alkyl.

In a preferred embodiment, the present invention relates to such compounds wherein $R^{10}$ is selected from hydrogen, acetyl, hydroxy, a group —$NR^{30}COR^{31}$ wherein $R^{30}$ is hydrogen and $R^{31}$ is methyl, a group —$COOR^{16}$ wherein $R^{16}$ is ethyl, or a group —$CONR^{17}R^{18}$ wherein $R^{17}$ and $R^{18}$ together with the nitrogen to which they are attached form a piperidinyl or a 4-methylpiperazinyl.

In another preferred embodiment, the present invention relates to such compounds wherein m is 2, 3 or 4, more preferred m is 2.

In yet another embodiment, the present invention relates to such compounds wherein $R^1$ is a group $R^{11}CO$—, $R^{11}OCO$— wherein $R^{11}$ is $C_{3-6}$-alkyl, $C_{3-8}$-cycloalkyl, $C_{3-8}$-cycloalkyl-$C_{1-6}$-alkyl, phenyl, phenyl-$C_{1-6}$-alkyl, pyridyl, furanyl, benzo[1,2,5]oxadiazolyl, quinoxalinyl, benzo[b]thiophenyl or naphthalenyl wherein each of said $C_{3-6}$-alkyl, phenyl, pyridyl and furanyl groups independently are unsubstituted or substituted with one or more substituents selected from the group comprising halogen, $C_{1-6}$-alkyl, $C_{1-6}$-alkoxy, phenyl and phenoxy wherein said phenyl and phenoxy independently are unsubstituted or substituted with one halogen; or $R^1$ is a group $R^{14}R^{15}NCO—$, wherein $R^{14}$ and $R^{15}$ are independently hydrogen, $C_{1-6}$-alkyl, aryl, or aryl-$C_{1-6}$- alkyl, wherein each of said $C_{1-6}$-alkyl and aryl groups independently are unsubstituted or substituted with one substituent selected from the group comprising halogen and $C_{1-6}$-alkoxy.

In yet another embodiment, the present invention relates to such compounds wherein $R^2$ is hydrogen.

In yet another embodiment, the present invention relates to such compounds wherein $R^3$ is hydrogen.

In yet another embodiment, the present invention relates to such compounds wherein $R^4$ is hydrogen or methoxy.

In yet another embodiment, the present invention relates to such compounds wherein $R^5$ is hydrogen or methoxy.

In yet another embodiment, the present invention relates to such compounds wherein $R^6$ is hydrogen.

In yet another embodiment, the present invention relates to such compounds wherein $R^{7a}$ and $R^{7b}$ is hydrogen.

In yet another embodiment, the present invention relates to such compounds wherein $R^{8a}$ and $R^{8b}$ is hydrogen.

Preferred compounds of the invention are compounds number 1-209 as disclosed in the experimental section as well as the compounds in the following list:

1-(1-{2-[4-(5-Fluoro-1H-indol-3-yl)-piperidin-1-yl]-ethyl}-5-chloro-3,4-dihydro-1H-isoquinolin-2-yl)-1-(4-fluorophenyl)methanone, 1-cyclopentyl-1-(1-{2-[4-(5-fluoro-1H-indol-3-yl)-piperidin-1-yl]-ethyl}-5-chloro-3,4-dihydro-1H-isoquinolin-2-yl)methanone, 1-cyclopentyl-1-(1-{2-[6-fluorospiro[isobenzofuran-1(3H),4'-piperidine-1'-yl]-ethyl}-5-chloro-3,4-dihydro-1H-isoquinolin-2-yl)methanone, 1-(4-fluorophenyl)-1-(1-{2-[6-fluorospiro[isobenzofuran-1(3H),4'-piperidine-1'-yl]-ethyl}-5-chloro-3,4-dihydro-1H-isoquinolin-2-yl)methanone, 1-cyclopentyl-1-(1-{2-[6-trifluoromethylspiro[isobenzofuran-1(3H),4'-piperidine-1'-yl]-ethyl}-5-chloro-3,4-dihydro-1H-isoquinolin-2-yl)methanone, 1-(4-fluorophenyl)-1-(1-{2-[6-trifluoromethylspiro[isobenzofuran-1(3H),4'-piperidine-1'-yl]-ethyl}-5-chloro-3,4-dihydro-1H-isoquinolin-2-yl)methanone, N-[1-{2-[2-(1-cyclopentyl-methanoyl)-1,2,3,4-tetrahydro-isoquinolin-1-yl]-ethyl}-4-(3-fluorophenyl)-piperidin-4-yl]acetamide, N-[1-{2-[2-(1-(4-fluorophenyl)-methanoyl)-1,2,3,4-tetrahydro-isoquinolin-1-yl]-ethyl}-4-(3-fluorophenyl)-piperidin-4-yl]acetamide, N-[1-{2-[2-(1-cyclopentyl-methanoyl)-1,2,3,4-tetrahydro-isoquinolin-1-yl]-ethyl}-4-phenylpiperidin-4-yl]acetamide, N-[1-{2-[2-(1-(4-fluorophenyl)-methanoyl)-1,2,3,4-tetrahydro-isoquinolin-1-yl]-ethyl}-4-phenylpiperidin-4-yl]acetamide, 1-cyclopentyl-1-{1-[1-acetyl-spiro[2,3-dihydro-1H-indol-3,4'-piperidin-1'-yl]ethyl]-5-chloro-3,4-dihydro-1H-isoquinolin-2-yl}methanone, 1-(4-fluorophenyl)-1-{1-[1-acetyl-spiro[2,3-dihydro-1H-indol-3,4'-piperidin-1'-yl]ethyl]-5-chloro-3,4-dihydro-1H-isoquinolin-2-yl}methanone, 1-cyclopentyl-1-{1-[1-acetyl-spiro[2,3-dihydro-5-fluoro-1H-indol-3,4'-piperidin-1'-yl]-ethyl]-5-chloro-3,4-dihydro-1H-isoquinolin-2-yl}methanone, 1-(4-fluorophenyl)-1-{1-[1-acetyl-spiro[2,3-dihydro-5-fluoro-1H-indol-3,4'-piperidin-1'-yl]-ethyl]-5-chloro-3,4-dihydro-1H-isoquinolin-2-yl}methanone, 1-cyclopentyl-1-(1-{2-[4-(3-trifluoromethylphenyl)-piperidin-1-yl]-ethyl}-5-chloro-3,4-dihydro-1H-isoquinolin-2-yl)methanone, 1-(4-fluorophenyl)-1-(1-{2-[4-(3-trifluoromethylphenyl)-piperidin-1-yl]-ethyl}-5-chloro-3,4-dihydro-1H-isoquinolin-2-yl)methanone, 1-(1-{2-[4-(6-fluorobenzo[d]isoxazol-3-yl)-piperidin-1-yl]-ethyl}-5-chloro-3,4-dihydro-1H-isoquinolin-2-yl)-1-(4-fluorophenyl)methanone, 1-(1-{2-[4-(6-fluorobenzo[d]isoxazol-3-yl)-piperidin-1-yl]-ethyl}-5-chloro-3,4-dihydro-1H-isoquinolin-2-yl)-1-(cyclopentyl)methanone, 1-(4-fluorophenyl)-1-(1-{2-[5,6-difluorospiro[benzofuran-1(3H),4'-piperidine-1'-yl]-ethyl}-5-chloro-3,4-dihydro-1H-isoquinolin-2-yl)-methanone, 1-(4-fluorophenyl)-1-({2-[6-fluorospiro[benzofuran-1(3H),4'-piperidine-1'-yl]-ethyl}-5-chloro-3,4-dihydro-1H-isoquinolin-2-yl)methanone, 1-cyclopentyl-1-(1-{2-[5,6-difluorospiro[benzofuran-1(3H),4'-piperidine-1'-yl]-ethyl}-5-chloro-3,4-dihydro-1H-isoquinolin-2-yl)-methanone, 1-cyclopentyl-1-({2-[6-fluorospiro[benzofuran-1(3H),4'-piperidine-1'-yl]-ethyl}-5-chloro-3,4-dihydro-1H-isoquinolin-2-yl)methanone, 1-(1-{2-[4-(5-fluoro-1H-indol-3-yl)-piperidin-1-yl]-ethyl}-3,4-dihydro-5-fluoro-1H-isoquinolin-2-yl)-1-(4-fluorophenyl)methanone, 1-cyclopentyl-1-(1-{2-[4-(5-fluoro-1H-indol-3-yl)-piperidin-1-yl]-ethyl}-3,4-dihydro-5-fluoro-1H-isoquinolin-2-yl)methanone, 1-cyclopentyl-1-(1-{2-[6-fluorospiro[isobenzofuran-1(3H),4'-piperidine-1'-yl]-ethyl}-3,4-dihydro-5-fluoro-1H-isoquinolin-2-yl)methanone, 1-(4-fluorophenyl)-1-(1-{2-[6-fluorospiro[isobenzofuran-1(3H),4'-piperidine-1'-yl]-ethyl}-3,4-dihydro-5-fluoro-1H-isoquinolin-2-yl)methanone, 1-cyclopentyl-1-(1-{2-[6-trifluoromethylspiro[isobenzofuran-1(3H),4'-piperidine-1'-yl]-ethyl}-3,4-dihydro-5-fluoro-1H-isoquinolin-2-yl)methanone, 1-(4-fluorophenyl)-1-(1-{2-[6-trifluoromethylspiro[isobenzofuran-1(3H),4'-piperidine-1'-yl]ethyl}-3,4-dihydro-5-fluoro-1H-isoquinolin-2-yl)methanone, N-[1-{2-[2-(1-cyclopentyl-methanoyl)-1,2,3,4-tetrahydro-isoquinolin-1-yl]-ethyl}-4-(3-fluorophenyl)-piperidin-4-yl]acetamide, N-[1-{2-[2-(1-(4-fluorophenyl)-methanoyl)-1,2,3,4-tetrahydro-isoquinolin-1-yl]-ethyl}-4-(3-fluorophenyl)-piperidin-4-yl]acetamide, N-[1-{2-[2-(1-cyclopentyl-methanoyl)-1,2,3,4-tetrahydro-isoquinolin-1-yl]-ethyl}-4-phenylpiperidin-4-yl]acetamide, N-[1-{2-[2-(1-(4-fluorophenyl)-methanoyl)-1,2,3,4-tetrahydro-isoquinolin-1-yl]-ethyl}-4-phenylpiperidin-4-yl]acetamide, 1-cyclopentyl-1-{1-[1-acetyl-spiro[2,3-dihydro-1H-indol-3,4'-piperidin-1'-yl]ethyl]-3,4-dihydro-5-fluoro-1H-isoquinolin-2-yl}methanone, 1-(4-fluorophenyl)-1-{1-[1-acetyl-spiro[2,3-dihydro-1H-indol-3,4'-piperidin-1'-yl]ethyl]-3,4-dihydro-5-fluoro-1H-isoquinolin-2-yl}methanone, 1-cyclopentyl-1-{1-[1-acetyl-spiro[2,3-dihydro-5-fluoro-1H-indol-3,4'-piperidin-1'-yl]-ethyl]-3,4-dihydro-5-fluoro-1H-isoquinolin-2-yl}methanone, 1-(4-fluorophenyl)-1-{1-[1-acetyl-spiro[2,3-dihydro-5-fluoro-1H-indol-3,4'-piperidin-1'-yl]-ethyl]-3,4-dihydro-5-fluoro-1H-isoquinolin-2-yl}methanone, 1-cyclopentyl-1-(1-{2-[4-(3-trifluoromethylphenyl)-piperidin-1-yl]-ethyl}-3,4-dihydro-5-fluoro-1H-isoquinolin-2-yl)methanone, 1-(4-fluorophenyl)-1-(1-{2-[4-(3-trifluoromethylphenyl)-piperidin-1-yl]-ethyl}-3,4-dihydro-5-fluoro-1H-isoquinolin-2-yl)methanone, 1-(1-{2-[4-(6-fluorobenzo[d]isoxazol-3-yl)-piperidin-1-yl]-ethyl}-3,4-dihydro-5-fluoro-1H-isoquinolin-2-yl)-1-(4-fluorophenyl)methanone, 1-(1-{2-[4-(6-fluorobenzo[d]isoxazol-3-yl)-piperidin-1-yl]-ethyl}-3,4-dihydro-5-fluoro-1H-isoquinolin-2-yl)-1-(cyclopentyl)methanone, 1-(4-fluorophenyl)-1-(1-{2-[5,6-difluorospiro[benzofuran-1(3H),4'-piperidine-1'-yl]-ethyl}-3,4-dihydro-5-fluoro-1H-isoquinolin-2-yl)-methanone, 1-(4-fluorophenyl)-1-({2-[6-fluorospiro[benzofuran-1(3H),4'-piperidine-1'-yl]-ethyl}-3,4-dihydro-5-fluoro-1H-isoquinolin-2-yl)methanone, 1-cyclopentyl-1-(1-{2-[5,6-difluorospiro[benzofuran-1(3H),4'-piperidine-1'-yl]-ethyl}-3,4-dihydro-5-fluoro-1H-isoquinolin-2-yl)-methanone, 1-cyclopentyl-1-({2-[6-fluorospiro[benzofuran(3H),4'-piperidine-1'-yl]-ethyl}-3,4-dihydro-5-fluoro-1H-isoquinolin-2-yl)methanone, 1-(1-{2-[4-(5-fluoro-1H-indol-3-yl)-piperidin-1-yl]-ethyl}-5,6-dichloro-3,4-dihydro-1H-isoquinolin-2-yl)-1-(4-fluoro-phenyl)methanone, 1-cyclopentyl-1-(1-{2-[4-(5-fluoro-1H-indol-3-yl)-piperidin-1-yl]-ethyl}-5,6-dichloro-3,4-dihydro-1H-isoquinolin-2-yl)methanone, 1-cyclopentyl-1-(1-{2-[6-fluorospiro[isobenzofuran-1(3H),4'-piperidine-1'-yl]-ethyl}-5,6-dichloro-3,4-dihydro-1H-isoquinolin-2-yl)methanone, 1-(4-fluorophenyl)-1-(1-{2-[6-fluorospiro[isobenzofuran-1(3H),4'-piperidine-1'-yl]-ethyl}-5,6-dichloro-3,4-dihydro-1H-isoquinolin-2-yl)methanone, 1-cyclopentyl-1-(1-{2-[6-trifluoromethylspiro[isobenzofuran-1(3H),4'-piperidine-1'-yl]-ethyl)-5,6-dichloro-3,4-dihydro-1H-isoquinolin-2-yl)methanone, 1-(4-fluorophenyl)-1-(1-{2-[6-trifluoromethylspiro[isobenzofuran-1(3H),4'-piperidine-1'-yl]ethyl)-5,6-dichloro-3,4-dihydro-1H-isoquinolin-2-yl)methanone, N-[1-{2-[2-(1-cyclopentyl-methanoyl)-1,2,3,4-tetrahydro-isoquinolin-1-yl]-ethyl}-4-(3-fluorophenyl)-piperidin-4-yl]acetamide, N-[1-{2-[2-(1-(4-fluorophenyl)-methanoyl)-1,2,3,4-tetrahydro-isoquinolin-1-yl]-ethyl)-4-(3-fluorophenyl)-piperidin-4-yl]acetamide, N-[1-{2-[2-(1-cyclopentyl-methanoyl)-1,2,3,4-tetrahydro-isoquinolin-1-yl]-ethyl}-4-phenylpiperidin-4-yl]acetamide, N-[1-{2-[2-(1-(4-fluorophenyl)-methanoyl)-1,2,3,4-tetrahydro-isoquinolin-1-yl]-ethyl}-4-phenylpiperidin-4-yl]acetamide, 1-cyclopentyl-1-{1-[1-acetyl-spiro[2,3-dihydro-1H-indol-3,4'-piperidin-1'-yl]ethyl]-5,6-dichloro-3,4-dihydro-1H-isoquinolin-2-yl}methanone, 1-(4-fluorophenyl)-1-{1-[1-acetyl-spiro[2,3-dihydro-1H-indol-3,4'-piperidin-1'-yl]ethyl]-5,6-dichloro-3,4-dihydro-1H-isoquinolin-2-yl}methanone, 1-cyclopentyl-1-{1-[1-acetyl-spiro[2,3-dihydro-5-fluoro-1H-indol-3,4'-piperidin-1'-yl]-ethyl]-5,6-dichloro-3,4-dihydro-1H-isoquinolin-2-yl}methanone, 1-(4-fluorophenyl)-1-{1-[1-acetyl-spiro[2,3-dihydro-5-fluoro-1H-indol-3,4'-piperidin-1'-yl]-ethyl]-5,6-dichloro-3,4-dihydro-1H-isoquinolin-2-yl}methanone, 1-cyclopentyl-1-(1-{2-[4-(3-trifluoromethylphenyl)-piperidin-1-yl]-ethyl}-5,6-dichloro-3,4-dihydro-1H-isoquinolin-2-yl)methanone, 1-(4-fluorophenyl)-1-(1-{2-[4-(3-trifluoromethylphenyl)-piperidin-1-yl]-ethyl}-5,6-dichloro-3,4-dihydro-1H-isoquinolin-2-yl)methanone, 1-(1-{2-[4-(6-fluorobenzo[d]isoxazol-3-yl)-piperidin-1-yl]-ethyl}-5,6-dichloro-3,4-dihydro-1H-isoquinolin-2-yl)-1-(4-fluorophenyl)methanone, 1-(1-{2-[4-(6-fluorobenzo[d]isoxazol-3-yl)-piperidin-1-yl]-ethyl}-5,6-dichloro-3,4-dihydro-1H-isoquinolin-2-yl)-1-cyclopentyl)methanone, 1-(4-fluorophenyl)-1-(1-{2-[5,6-difluorospiro[benzofuran-1(3H),4'-piperidine-1'-yl]-ethyl}-5,6-dichloro-3,4-dihydro-1H-isoquinolin-2-yl)-methanone, 1-(4-fluorophenyl)-1-({2-[6-fluorospiro[benzofuran-1(3H),4'-piperidine-1'-yl]-ethyl}-5,6-dichloro-3,4-dihydro-1H-isoquinolin-2-yl)methanone, 1-cyclopentyl-1-(1-{2-[5,6-difluorospiro[benzofuran-1(3H),4'-piperidine-1'-yl]-ethyl}-5,6-dichloro-3,4-dihydro-1H-isoquinolin-2-yl)-methanone, 1-cyclopentyl-1-({2-[6-fluorospiro[benzofuran(3H),4'-piperidine-1'-yl]-ethyl}-5,6-dichloro-3,4-dihydro-1H-isoquinolin-2-yl)methanone, 1-(1-{2-[4-(5-fluoro-1H-indol-3-yl)-piperidin-1-yl]-ethyl}-5,6-difluoro-3,4-dihydro-1H-isoquinolin-2-yl)-1-(4-fluoro-phenyl)methanone, 1-cyclopentyl-1-(1-(2-[4-(5-fluoro-1H-indol-3-yl)-piperidin-1-yl]-ethyl}-5,6-difluoro-3,4-dihydro-1H-isoquinolin-2-yl)methanone, 1-cyclopentyl-1-(1-{2-[6-fluorospiro[isobenzofuran-1(3H),4'-piperidine-1'-yl]-ethyl}-5,6-difluoro-3,4-dihydro-1H-isoquinolin-2-yl)methanone, 1-(4-fluorophenyl)-1-(1-{2-[6-fluorospiro[isobenzofuran-1(3H),4'-piperidine-1'-yl]-ethyl}-5,6-difluoro-3,4-dihydro-1H-isoquinolin-2-yl)methanone, 1-cyclopentyl-1-(1-{2-[6-trifluoromethylspiro[isobenzofuran-1(3H),4'-piperidine-1'-yl]-ethyl)-5,6-difluoro-3,4-dihydro-1H-isoquinolin-2-yl)methanone, 1-(4-fluorophenyl)-1-(1-{2-[6-trifluoromethylspiro[isobenzofuran-1(3H),4'-piperidine-1'-yl]ethyl)-5,6-difluoro-3,4-dihydro-1H-isoquinolin-2-yl)methanone, N-[1-{2-[2-(1-cyclopentyl-methanoyl)-1,2,3,4-tetrahydro-isoquinolin-1-yl]-ethyl}-4-(3-fluorophenyl)-piperidin-4-yl]acetamide, N-[1-{2-[2-(1-(4-fluorophenyl)-methanoyl)-1,2,3,4-tetrahydro-isoquinolin-1-yl]-ethyl)-4-(3-fluorophenyl)-piperidin-4-yl]acetamide, N-[1-{2-[2-(1-cyclopentyl-methanoyl)-1,2,3,4-tetrahydro-isoquinolin-1-yl]-ethyl}-4-phenylpiperidin-4-yl]acetamide, N-[1-{2-[2-(1-(4-fluorophenyl)-methanoyl)-1,2,3,4-tetrahydro-isoquinolin-1-yl]-ethyl}-4-phenylpiperidin-4-yl]acetamide, 1-cyclopentyl-1-{1-[1-acetyl-spiro[2,3-dihydro-1H-indol-3,4'-piperidin-1'-yl]ethyl]-5,6-difluoro-3,4-dihydro-1H-isoquinolin-2-yl}methanone, 1-(4-fluorophenyl)-1-{1-[1-acetyl-spiro[2,3-dihydro-1H-indol-3,4'-piperidin-1'-yl]ethyl]-5,6-difluoro-3,4-dihydro-1H-isoquinolin-2-yl}methanone, 1-cyclopentyl-1-(1-[1-acetyl-spiro[2,3-dihydro-5-fluoro-1H-indol-3,4'-piperidin-1'-yl]-ethyl]-5,6-difluoro-3,4-dihydro-1H-isoquinolin-2-yl)methanone, 1-(4-fluorophenyl)-1-(1-[1-acetyl-spiro[2,3-dihydro-5-fluoro-1H-indol-3,4'-piperidin-1'-yl]-ethyl]-5,6-difluoro-3,4-dihydro-1H-isoquinolin-2-yl}methanone, 1-cyclopentyl-1-(1-{2-[4-(3-trifluoromethylphenyl)-piperidin-1-yl]-ethyl}-5,6-difluoro-3,4-dihydro-1H-isoquinolin-2-yl)methanone, 1-(4-fluorophenyl)-1-(1-{2-[4-(3-trifluoromethylphenyl)-piperidin-1-yl]-ethyl}-5,6-difluoro-3,4-dihydro-1H-isoquinolin-2-yl)methanone, 1-(1-{2-[4-(6-fluorobenzo[d]isoxazol-3-yl)-piperidin-1-yl]-ethyl}-5,6-difluoro-3,4-dihydro-1H-isoquinolin-2-yl)-1-(4-fluorophenyl)methanone, 1-(1-{2-[4-(6-fluorobenzo[d]isoxazol-3-yl)-piperidin-1-yl]-ethyl}-5,6-difluoro-3,4-dihydro-1H-isoquinolin-2-yl)-1-(cyclopentyl)methanone, 1-(4-fluorophenyl)-1-(1-{2-[5,6-difluorospiro[benzofuran-1(3H),4'-piperidine-1'-yl]-ethyl}-5,6-difluoro-3,4-dihydro-1H-isoquinolin-2-yl)-methanone, 1-(4-fluorophenyl)-1-({2-[6-fluorospiro[benzofuran-1(3H),4'-piperidine-1'-yl]-ethyl}-5,6-difluoro-3,4-dihydro-1H-isoquinolin-2-yl)methanone, 1-cyclopentyl-1-(1-{2-[5,6-difluorospiro[benzofuran-1(3H),4'-piperidine-1'-yl]-ethyl}-5,6-difluoro-3,4-dihydro-1H-isoquinolin-2-yl)-methanone, and 1-cyclopentyl-1-({2-[6-fluorospiro[benzofuran-1(3H),4'-piperidine-1'-yl]-ethyl}-5,6-difluoro-3,4-dihydro-1H-isoquinolin-2-yl)methanone.

The compounds of the invention are $NK_2$ receptors antagonists having a human $NK_2$ binding affinity (IC50) of 5 µM or less, typically of 1 µM or less, preferably of 200 nM or less, more preferred of 50 nM or less and most preferred of 10 µM or less.

Accordingly, the compounds of the invention are considered useful in treating a variety of CNS diseases such as depression, manic depression, bipolar disorder, dysthymia, mixed anxiety depression, generalised anxiety disorder, social anxiety disorder, panic anxiety disorder, post traumatic stress disorder, obsessive compulsive disorder, acute stress disorder, phobia, pre-menstrual dysphoric disorder, psychosis and Huntington's disease as well as Parkinson's dementia, adjustment disorders, pain, emesis, migraine, epilepsia, obesity and cerebrovascular disease.

In particular, the compounds of the invention are considered useful in the treatment of depression, manic depression, bipolar disorder, dysthymia, mixed anxiety depression, generalised anxiety disorder, social anxiety disorder, panic anxiety disorder, post traumatic stress disorder, obsessive compulsive disorder, acute stress disorder, phobia, pre-menstrual dysphoric disorder and psychosis.

Thus, in another aspect, the present invention provides a pharmaceutical composition comprising at least one compound of formula I as defined above or a pharmaceutically acceptable acid addition salt thereof in a therapeutically effective amount and in combination with one or more pharmaceutically acceptable carriers or diluents.

In a further aspect, the present invention provides the use of a compound of formula I as defined above or an acid addition salt thereof for the manufacture of a pharmaceutical preparation for the treatment of the above mentioned disorders.

The compounds of the general formula I may exist as optical isomers thereof and such optical isomers are also embraced by the invention. Throughout the specification and claims, reference to specific compounds refers to the racemates unless otherwise indicated.

The term $C_{1-6}$-alkyl refers to a branched or unbranched alkyl group having from one to six carbon atoms inclusive, such as methyl, ethyl, 1-propyl, 2-propyl, 1-butyl, 2-butyl, 2-methyl-2-propyl, and 2-methyl-1-propyl. The terms $C_{1-8}$-alkyl, $C_{1-10}$-alkyl and $C_{1-12}$-alkyl, respectively, refer similarly to branched or unbranched alkyl group having from one to eight, ten or twelve carbon atoms inclusive, respectively.

Similarly, $C_{2-6}$-alkenyl and $C_{2-6}$-alkynyl, respectively, designate such groups having from two to six carbon atoms, including one double bond and one triple bond, respectively, such as ethenyl, propenyl, butenyl, ethynyl, propynyl and butynyl.

The term $C_{3-8}$-cycloalkyl designates a monocyclic or bicyclic carbocycle having three to eight C-atoms, such as cyclopropyl, cyclopentyl, cyclohexyl, etc.

Halogen means fluoro, chloro, bromo or iodo.

As used herein, the term acyl refers to a formyl, $C_{1-6}$-alkylcarbonyl, arylcarbonyl, aryl-$C_{1-6}$-alkylcarbonyl, $C_{3-8}$-cycloalkylcarbonyl or a $C_{3-8}$-cycloalkyl-$C_{1-6}$-alkyl-carbonyl group, and the term thioacyl is the corresponding acyl group, in which the carbonyl group is replaced with a thiocarbonyl group.

The terms $C_{1-6}$-alkoxy, $C_{3-8}$-cycloalkyl-$C_{1-6}$-alkyl, $C_{1-6}$-alkylsulfonyl, $C_{1-6}$-alkylamino, $C_{1-6}$-alkylcarbonyl, and the like, designate such groups in which the $C_{1-6}$-alkyl and the $C_{3-8}$-cycloalkyl group are as defined above.

The term aryl refers to a carbocyclic aromatic group, such as phenyl or naphthyl, in particular phenyl.

The term heteroaryl refers to 5-membered monocyclic rings such as 1H-tetrazolyl, 3H-1,2,3-oxathiazolyl, 3H-1,2,4-oxathiazolyl, 3H-1,2,5-oxathiazolyl, 1,3,2-oxathiazolyl, 1,3,4-oxathiazolyl, 1,4,2-oxathiazolyl, 3H-1,2,4-dioxazolyl, 1,3,2-dioxazolyl, 1,4,2-dioxazolyl, 3H-1,2,3-dithiazolyl, 3H-1,2,4-dithiazolyl, 1,3,2-dithiazolyl, 1,4,2-dithiazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, 1H-1,2,3-triazolyl, 1H-1,2,4-triazolyl, isoxazolyl, oxazolyl, isothiazolyl, thiazolyl, 1H-imidazolyl, 1H-pyrazolyl, 1H-pyrrolyl, furanyl, thienyl, 1H-pentazole; 6-membered monocyclic rings such as 1,2,3-oxathiazinyl, 1,2,4-oxathiazinyl, 1,2,5-oxathiazinyl, 4H-1,3,5-oxathiazinyl, 1,4,2-oxathiazinyl, 1,4,3-oxathiazinyl, 1,2,3-dioxazinyl, 1,2,4-dioxazinyl, 4H-1,3,2-dioxazinyl, 4H-1,3,5-dioxazinyl, 1,4,2-dioxazinyl, 2H-1,5,2-dioxazinyl, 1,2,3-dithiazinyl, 1,2,4-dithiazinyl, 4H-1,3,2-dithiazinyl, 4H-1,3,5-dithiazinyl, 1,4,2-dithiazinyl, 2H-1,5,2-dithiazinyl, 2H-1,2,3-oxadiazinyl, 2H-1,2,4-oxadiazinyl, 2H-1,2,5-oxadiazinyl, 2H-1,2,6-oxadiazinyl, 2H-1,3,4-oxadiazinyl, 2H-1,3,5-oxadiazinyl, 2H-1,2,3-thiadiazinyl, 2H-1,2,4-thiadiazinyl, 2H-1,2,5-thiadiazinyl, 2H-1,2,6-thiadiazinyl, 2H-1,3,4-thiadiazinyl, 2H-1,3,5-thiadiazinyl, 1,2,3-triazinyl, 1,2,4-triazinyl, 1,3,5-triazinyl, 2H-1,2-oxazinyl, 2H-1,3-oxazinyl, 2H-1,4-oxazinyl, 2H-1,2-thiazinyl, 2H-1,3-thiazinyl, 2H-1,4-thiazinyl, pyrazinyl, pyridazinyl, pyrimidyl, pyridyl, 2H-pyranyl, 2H-thiinyl; and to bicyclic rings such as 3H-1,2,3-benzoxathiazolyl, 1,3,2-benzodioxazolyl, 3H-1,2,3-benzodithiazolyl, 1,3,2-benzodithiazolyl, benzfurazanyl, 1,2,3-benzoxadiazolyl, 1,2,3-benzothiadiazolyl, 2,1,3-benzothiadiazolyl, 1H-benzotriazolyl, 1,2-benzisoxazolyl, 2,1-benzisoxazolyl, benzoxazolyl, 1,2-benzisothiazolyl, 2,1-benzisothiazolyl, benzothiazolyl, 1H-benzimidazolyl, 1H-indazolyl, 3H-1,2-benzoxathiolyl, 1,3-benzoxathiolyl, 3H-2,1-benzoxathiolyl, 3H-1,2-benzodioxolyl, 1,3-benzodioxolyl 3H-1,2-benzodithiolyl, 1,3-benzodithiolyl, 1H-indolyl, 2H-isoindolyl, benzofuranyl, isobenzofuranyl, 1-benzothienyl, 2-benzothienyl, 1H-2,1-benzoxazinyl, 1H-2,3-benzoxazinyl, 2H-1,2-benzoxazinyl, 2H-1,3-benzoxazinyl, 2H-1,4-benzoxazinyl, 2H-3,1-benzoxazinyl, 1H-2,1-benzothiazinyl, 1H-2,3-benzothiazinyl, 2H-1,2-benzothiazinyl, 2H-1,3-benzothiazinyl, 2H-1,4-benzothiazinyl, 2H-3,1-benzothiazinyl, cinnolinyl, phtalazinyl, quinazolinyl, quinoxalinyl, isoquinolyl, quinolyl, 1H-2-benzopyranyl, 2H-1-benzopyranyl, 1H-2-benzothiopyranyl or 2H-1-benzothiopyranyl.

The acid addition salts of the compounds of the invention are pharmaceutically acceptable salts formed with non-toxic acids. Exemplary of such organic salts are those with maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic and theophylline acetic acids, as well as the 8-halotheophyllines, for example 8-bromotheophylline. Exemplary of such inorganic salts are those with hydrochloric, hydrobromic, sulfuric, sulfamic, phosphoric and nitric acids.

The pharmaceutical compositions of this invention, or those which are manufactured in accordance with this invention, may be administered by any suitable route, for example orally in the form of tablets, capsules, powders, syrups, etc., or parenterally in the form of solutions for injection. For preparing such compositions, methods well known in the art may be used, and any pharmaceutically acceptable carriers, diluents, excipients or other additives normally used in the art may be used.

Conveniently, the compounds of the invention are administered in unit dosage form containing said compounds in an amount of about 0.01 to 100 mg.

The total daily dose is usually in the range of about 0.05-500 mg, and most preferably about 0.1 to 50 mg of the active compound of the invention.

The compounds of the invention may be prepared as follows:

1) Alkylating a piperazine, piperidine or tetrahydropyridine of formula III with an alkylating derivative of formula II:

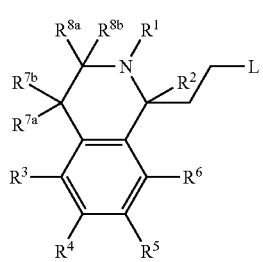

(II)

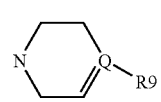

(III)

wherein $R^1$-$R^9$ and Q are as previously defined and L is a leaving group such as e.g. halogen, mesylate or tosylate;

2) Reductive alkylation of an amine of formula III with a reagent of formula IV:

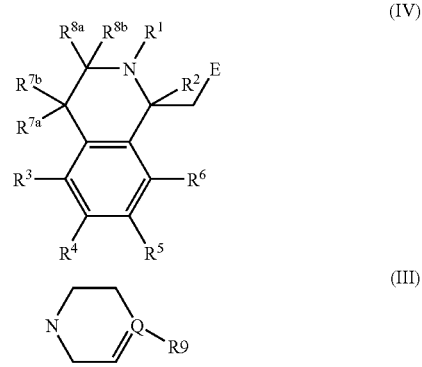

(IV)

(III)

wherein $R^1$-$R^9$ and Q are as previously defined and E is an aldehyde or an activated carboxylic acid;

3) Acylating an amine of formula V by the use of a carboxylic acid and a coupling reagent, an activated ester, an acid chloride, an isocyanate, carbamoyl chloride or by a two-step procedure by treatment with phosgene followed by addition of an amine:

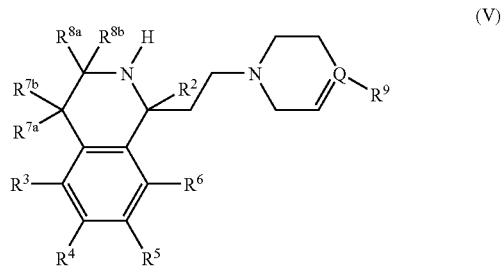

(V)

wherein $R^1$-$R^9$ and Q are as previously defined, whereupon the compound of formula I is isolated as the free base or a pharmaceutically acceptable acid addition salt thereof.

The alkylation according to method 1) is conveniently performed in an organic solvent such as a suitably boiling alcohol or ketone, preferably in the presence of an organic or inorganic base (potassium carbonate, diisopropylethylamine or triethylamine) at reflux temperature. Alternatively, the alkylation can be performed at a fixed temperature, which is different from the boiling point, in one of the above-mentioned solvents or in dimethyl formamide (DMF), dimethylsulfoxide (DMSO), or N-methylpyrrolidin-2-one (NMP), preferably in the presence of a base. The alkylating agents of formula II can be prepared by methods analogues to those described in the examples or can be synthesised by applying methods described in standard works such as Houben-Weyl, Methoden der organischen Chemie (Methods of Organic Chemistry), Georg-Thieme-Verlag, Stuttgart; Organic Reactions, John Wiley & Sons, Inc. New York, namely under reaction conditions such as those which are known and suitable for such reactions. The amines of formula III are either commercially available or have been described in the literature or can be prepared by methods analogues to those described in the literature e.g. Marxer et al. *J. Org. Chem.* 1975, 40, 1427, by Parham et al. *J. Org. Chem.* 1976, 41, 2628 and by Bauer et al. *J. Med.*

Chem. 1976, 19, 1315, Maligres et al. *Tetrahedron* 1997, 53, 10983, and by Cheng et al. *Tet. Lett.* 1997, 38, 1497, Chen, Meng-Hsin; Abraham, John A. *Tetrahedron Lett.* 1996, 37, 5233-5234 and Slade, P. D. et al. *J. Med. Chem.* 1998, 41, 1218-1235, or can be synthesised by methods described in standard works such as Houben-Weyl, Methoden der organischen Chemie (Methods of Organic Chemistry), Georg-Thieme-Verlag, Stuttgart; Organic Reactions, John Wiley & Sons, Inc. New York, namely under reaction conditions such as those which are known and suitable for such reactions.

The reductive alkylation according to method 2) is performed by standard literature methods or as described in standard works such as Houben-Weyl, Methoden der organischen Chemie (Methods of Organic Chemistry), Georg-Thieme-Verlag, Stuttgart; Organic Reactions, John Wiley & Sons, Inc. New York, namely under reaction conditions such as those which are known and suitable for such reactions. The reaction can be performed in two steps, e.g. coupling of amines of formula III with a reagent of formula IV by standard methods via the carboxylic acid chloride, activated esters or by the use of carboxylic acids in combination with a coupling reagents such as e.g. dicyclohexyl carbodiimide, followed by reduction of the resulting amide with lithium aluminium hydride or alane. The carboxylic acids of formula IV are either commercially available or can be prepared by methods analogues to those described in the literature (e.g. *Tet. Lett.* 37, 1996, pp. 5453-5456; *Tet. Lett.* 35, 1994, pp. 6567-6570; *J. Med. Chem.* 25, 1982, pp. 1235-1240; *Synthesis* 1987, pp. 474-477).

The acylation according to method 3) is conveniently performed by standard methods via the carboxylic acid chloride, activated esters or by the use of carboxylic acids in combination with coupling reagents such as e.g. dicyclohexyl carbodiimide. When the acylating reagent is carbamoyl chlorides or isocyanates, the acylation produces urea derivatives. The urea derivatives can also be prepared by a two-step procedure consisting of treatment with phosgene followed by addition of an amine.

The intermediate compounds of formula V are prepared as described in methods 1) and 2), wherein $R^2$-$R^9$, Q, L and E are as previously defined, and $R^1$ is a protection group. This protection group may be chosen from those protection group generally used for protection of amino groups. Those skilled in the art will know to select appropriate protection groups and how to protect and deprotect the amines with these protection groups.

Experimental Section

Melting points were determined on a Büchi SMP-20 apparatus and are uncorrected. Analytical LC-MS data were obtained on a PE Sciex API 150EX instrument equipped with IonSpray source and Shimadzu LC-8A/SLC-10A LC system. The LC conditions (C18 column 4.6×30 mm with a particle size of 3.5 μm) were linear gradient elution with water/acetonitrile/trifluoroacetic acid (90:10:0.05) to water/acetonitrile/trifluoroacetic acid (10:90:0.03) in 4 min at 2 mL/min. Purity was determined by integration of the UV trace (254 nm). The retention times, $R_t$, are expressed in minutes.

Mass spectra were obtained by an alternating scan method to give molecular weight information. The molecular ion, MH+, was obtained at low orifice voltage (5-20V) and fragmentation at high orifice voltage (100-200V).

Preparative LC-MS-separation was performed on the same instrument. The LC conditions (C18 column 20×50 mm with a particle size of 5 μm) were linear gradient elution with water/acetonitrile/trifluoroacetic acid (80:20:0.05) to water/acetonitrile/trifluoroacetic acid (5:95:0.03) in 7 min at 22.7 mL/min. Fraction collection was performed by split-flow MS detection.

$^1$H NMR spectra were recorded at 500.13 MHz on a Bruker Avance DRX500 instrument or at 250.13 MHz on a Bruker AC 250 instrument. Deuterated chloroform (99.8% D) or dimethyl sulfoxide (99.9% D) were used as solvents. TMS was used as internal reference standard. Chemical shift values are expressed in ppm-values. The following abbreviations are used for multiplicity of NMR signals: s=singlet, d=doublet, tt=triplet, q=quartet, qui=quintet, h=heptet, dd=double doublet, dt=double triplet, dq=double quartet, tt=triplet of triplets, m=multiplet. NMR signals corresponding to acidic protons are generally omitted. For column chromatography silica gel of type Kieselgel 60, 230-400 mesh ASTM was used. For ion-exchange chromatography (SCX, 1 g, Varian Mega Bond Elut®, Chrompack cat. No. 220776) was used. Prior use of the SCX-columns was pre-conditioned with 10% solution of acetic acid in methanol (3 mL).

Preparation of Intermediates

Alkylating Reagents of the Formula II 1. (RS)-1-(2-Bromo-ethyl)-3,4-dihydro-1H-isoquinoline-2-carboxylic acid-tert-butyl ester Tetrahydrosioquinolinic acid (10 g) was suspended in tetrahydrofuran THF (100 mL). Triethyl amine (9.1 mL) and di-tert-butyl dicarbonate (14.3 g) was added and the mixture stirred at room temperature for 16 h. The mixture was concentrated in vacuo, redissolved in ethyl acetate (250 mL) and washed twice with and aqueous 0.5 M $KHSO_4$-solution (200 mL), dried over magnesium sulphate and evaporated in vacuo to give 1-carboxymethyl-3,4-dihydro-1H-isoquinoline-2-carboxylic acid tert-butyl ester in quantitative yield as a clear oil which crystallised upon standing. The protected amino acid was dissolved in dry tetrahydrofuran under nitrogen, cooled to 0° C. and 1M borane in tetrahydrofuran (41.5 mL) was added slowly under nitrogen during 15 min. The mixture was warmed to room temperature and stirred for 1 h. Excess borane was carefully destroyed by slow addition of 50 mL of a 1:1 mixture of water/tetrahydrofuran. The mixture was made alkaline to pH=12 by addition of saturated potassium carbonate and extracted with diethylether (2×50 mL). The combined organic phase were dried (magnesium sulphate) and evaporated in vacuo to give 1-(2-Hydroxy-ethyl)-3,4-dihydro-1H-isoquinoline-2-carboxylic acid tert-butyl ester as a clear oil (8.4 g). The protected aminoalcohol was dissolved in dry tetrahydrofuran (150 mL) together with triethylamine (5.6 mL) and cooled to 0° C. under nitrogen. Methanosulfonyl chloride (2.64 mL) in dry THF (30 mL) was added dropwise during 15 min and the mixture was warmed to room temperature and stirred for 30 min. After filtration and concentration in vacuo the clear oily residue was dissolved in acetone (300 mL), lithium bromide (14.6 g) was added and the mixture was heated to reflux for 1 h. The mixture was filtered, evaporated in vacuo and the product purified by column chromatography on silicagel using as eluent ethyl acetate/heptane (1:1) and fractions containing the product was pooled and evaporated in vacuo to give (RS)-1-(2-Bromo-ethyl)-3,4-dihydro-1H-isoquinoline-2-carboxylic acid-tert-butyl ester as a clear oil (8 g) which crystallised upon standing.

The following compound was prepared in a similar way:
(RS)-1-(2-Bromo-ethyl)-6,7-dimethoxy-3,4-dihydro-1H-isoquinoline-2-carboxylic acid-tert-butyl ester Piperidines of the Formula III The piperidine-derivatives of formula III, wherein X is oxygen, Z is $CR^9R^{10}$, Y is a bond, $A^1$, $A^2$ and $A^4$ are CH, $A^3$ is $CR^{11}$, i.e. spiro[isobenzofuran-1(3H),4'-piperidines] are prepared according to the methods described by Marxer et al. *J. Org. Chem.* 1975, 40, 1427, by Parham et al. *J. Org. Chem.* 1976, 41, 2628 and by Bauer et al. *J. Med. Chem.* 1976, 19, 1315.

The following compounds were prepared in a similar way:
6-Fluorospiro[isobenzofuran-1(3H),4'-piperidine],
6-trifluoromethylspiro[isobenzofuran-1(3H),4'-piperidine],
6-fluoro-3-methylspiro[isobenzofuran-1(3H),4'-piperidine],
6-trifluoromethyl-3-methylspiro[isobenzofuran-1(3H),4'-piperidine],
5-methylspiro[isobenzofuran-1(3H),4'-piperidine],
6-fluoro-3-isobutylspiro[isobenzofuran-1(3H),4'-piperidine],
6-fluoro-3-cyclohexylspiro[isobenzofuran-1(3H),4'-piperidine] and
6-fluoro-3-(4-fluorophenyl)spiro[isobenzofuran-1(3H),4'-piperidine]

The piperidine-derivatives of formula III, wherein X is $CR^9R^{10}$, Z is $NR^8$, Y is a bond, $A^1$, $A^2$ and $A^4$ are CH, $A^3$ is $CR^{11}$ and $R^{11}$ is fluoro or trifluoromethyl, are prepared according to the methods described by Maligres et al. *Tetrahedron* 1997, 53, 10983, and by Cheng et al. *Tet. Lett.* 1997, 38, 1497.

The following compound was prepared in a similar way:
1-Acetyl-5-fluoro-spiro[2,3-dihydro-1H-indol-3,4'-piperidine].

The piperidine-derivatives of formula III, wherein the X is $CR^9R^{10}$, Z is oxygen, Y is a bond, $A^1$, $A^2$ and $A^4$ are CH, $A^3$ is $CR^{11}$, i.e. 2,3-dihydro-spiro(benzofuran-3,4'-piperidines), are prepared according to the methods described by Chen, Meng-Hsin; Abraham, John A. *Tetrahedron Lett.* 1996, 37, 5233-5234 and Slade, P. D. et al. *J. Med. Chem.* 1998, 41, 1218-1235.

The following compounds were prepared in a similar way:
2,3-Dihydro-5-fluorospiro[benzofuran-3,4'-piperidine] and
2,3-dihydro-5,6-difluorospiro[benzofuran-3,4'-piperidine]

The substituents $R^8$-$R^{11}$ are introduced by applying suitably substituted starting compounds to methods analogous to the above mentioned.

Amines of the Formula V

An amine of formula V was prepared by the following procedure:
A mixture of an amine of formula III (1 mmol), (RS)-1-(2-Bromo-ethyl)-3,4-dihydro-1H-isoquinoline-2-carboxylic acid-tert-butyl ester (1.3 mmol) and potassium carbonate (1.3 mmol) in acetonitrile (20 mL) were heated to 85° C. for 6 h. The mixture was cooled to room temperature and evaporated in vacuo to give an yellow oily residue. The product was redissolved in dichloromethane (10 mL) and anisole (0.26 mL) and trifluoroacetic acid (10 mL) were added and the mixture stirred at room temperature for 90 min. The mixture was evaporated in vacuo. The product was either purified by chromatography or used directly in the next step without purification.

The following compounds were purified by chromatography before further use:
(RS)-1-{2-[4-(5-Fluoro-1H-indol-3-yl)-piperidin-1-yl]-ethyl}-1,2,3,4-tetrahydro-isoquinoline
(RS)-1-{2-[6-fluorospiro[isobenzofuran-1(3H),4'-piperidine-1'-yl]-ethyl}-1,2,3,4-tetrahydroisoquinoline Enantiomeric Forms of Amines of the Formula V Enantiomer 1 and enantiomer 2 of N-(4-(3-Fluoro-phenyl)-1-[2-(1,2,3,4-tetrahydro-isoquinolin-1-yl)-ethyl]-piperidin-4-yl}acetamide Racemic N-{4-(3-fluoro-phenyl)-1-[2-(1,2,3,4-tetrahydro-isoquinolin-1-yl)-ethyl]-piperidin-4-yl}acetamide was subjected to resolution by chiral HPLC using a Gilson SF3 supercritical fluid chromatography system equipped with chiralcelOD columns (4.6 mm×25 cm for analytical and 10 mm×25 cm for preparative runs). The particle size in the columns was 10 μm. A solution of the racemic compound N-{4-(3-fluoro-phenyl)-1-[2-(1,2,3,4-tetrahydro-isoquinolin-1-yl)-ethyl]-piperidin-4-yl)acetamide (1 g) in methanol (1 mL) was injected in 40 μL portions on a preparative column. The column was eluted with carbondioxide-modifier (75:25). The modifier was 2-propanol with diethylamine (0.5%) and trifluoracetic acid (0.5%). The flow was 18.9 mL/min at 20 Mpa. Fraction collection was triggered by UV-detection (210 nM). The fractions containing the separate products were pooled and evaporated in vacuo which gave the enantiomers. The first eluted enantiomer is called Enantiomer 1 and the second eluted is called Enantiomer 2 of N-{4-(3-fluoro-phenyl)-1-[2-(1,2,3,4-tetrahydro-isoquinolin-1-yl)-ethyl]-piperidin-4-yl}acetamide. The enantiomers were measured by HPLC to have an enantiomeric excess higher than 95%.

The following enantiomers were prepared in a similar way:
Enantiomer 1 and enantiomer 2 of N-(4-(phenyl)-1-[2-(1,2,3,4-tetrahydro-isoquinolin-1-yl)-ethyl]-piperidin-4-yl}acetamide

EXAMPLES

Preparation of the Compounds of the Invention

The compounds of the present invention were prepared by one of two general methods:

Method A: Alkylating a Piperidine of Formula III with an Alkylating Derivative of Formula II:

A mixture of a piperidine of formula III (1 mmol), (RS)-1-(2-Bromo-ethyl)-3,4-dihydro-1H-isoquinoline-2-carboxylic acid-tert-butyl ester (1.3 mmol) and potassium carbonate (1.3 mmol) in acetonitrile (20 mL) were heated to 85° C. for 6 h. The mixture was cooled to room temperature and evaporated in vacuo. The product was purified by chromatography either on silicagel using as eluent ethylacetate/triethylamine (99:1) or by purified by HPLC. Fractions containing the product were pooled and evaporated in vacuo.

Method B: Acylating an Amine of Formula V by the Use of a Carboxylic Acid and a Coupling Reagent, an Activated Ester, an Acid Chloride or an Isocyanate:

An amine of formula V (prepared as described above; 1 mmol) and triethylamine (5 mmol) were dissolved in anhydrous acetonitrile (10 mL). An appropriately substituted acid chloride (5 mmol) was added and the reaction mixture stirred at room temperature for 30 min. Methanol (0.5 mL) was added to the reaction mixture followed by evaporation in vacuo. The product was purified by chromatography either on silicagel using ethylacetate/triethylamine (99:1) as eluent or by HPLC. Fractions containing the product were pooled and evaporated in vacuo and characterised by HPLC-UV-ELSD-MS. The measured HPLC-retention time, the measured molecular mass and UV- and ELSD-purities are shown in table 1.

The following compounds were made by the methods indicated in table 1. Analytical data are shown in table 1.

Compound
1. 1-(1-{2-[4-(5-Fluoro-1H-indol-3-yl)-piperidin-1-yl]-ethyl}-3,4-dihydro-1H-isoquinolin-2-yl)-1-(4-fluoro-phenyl)methanone
2. 1-Cyclopentyl-1-(1-{2-[4-(5-fluoro-1H-indol-3-yl)-piperidin-1-yl]-ethyl}-3,4-dihydro-1H-isoquinolin-2-yl)methanone
3. 1-(2-[4-(5-Fluoro-1H-indol-3-yl)-piperidin-1-yl]-ethyl}-3,4-dihydro-1H-isoquinoline-2-carboxylic acid phenethyl-amide
4. 1-(1-{2-[4-(5-Fluoro-1H-indol-3-yl)-piperidin-1-yl]-ethyl}-3,4-dihydro-1H-isoquinolin-2-yl)-1-phenylmethanone
5. 1-(1-{2-[4-(5-Fluoro-1H-indol-3-yl)-piperidin-1-yl]-ethyl}-3,4-dihydro-1H-isoquinolin-2-yl)-1-(2-fluoro-phenyl)methanone
6. 1-(1-{2-[4-(5-Fluoro-1H-indol-3-yl)-piperidin-1-yl]-ethyl}-3,4-dihydro-1H-isoquinolin-2-yl)-3-phenyl-propan-1-one
7. 1-{2-[4-(5-Fluoro-1H-indol-3-yl)-piperidin-1-yl]-ethyl}-3,4-dihydro-1H-isoquinoline-2-carboxylic acid (3-chloro-propyl)amide
8. 1-{2-[4-(5-Fluoro-1H-indol-3-yl)-piperidin-1-yl]-ethyl}-3,4-dihydro-1H-isoquinoline-2-carboxylic acid (2-methoxy-phenyl)amide
9. 1-{2-[4-(5-Fluoro-1H-indol-3-yl)-piperidin-1-yl]-ethyl}-3,4-dihydro-1H-isoquinoline-2-carboxylic acid tert-butyl ester
10. 3-Chloro-1-(1-{2-[4-(5-fluoro-1H-indol-3-yl)-piperidin-1-yl]-ethyl}-3,4-dihydro-1H-isoquinolin-2-yl)-2,2-dimethyl-propan-1-one
12. 1-Cyclopentyl-1-(1-{2-[6-fluorospiro[isobenzofuran-1(3H),4'-piperidine-1'-yl]-ethyl}-3,4-dihydro-1H-isoquinolin-2-yl)methanone
13. 1-[2-(4-Chloro-phenoxy)-pyridin-3-yl]-1-(1-{2-[6-fluorospiro[isobenzofuran-1(3H),4'-piperidine-1'-yl]-ethyl}-3,4-dihydro-1H-isoquinolin-2-yl)methano
14. 1-{2-[6-Fluorospiro[isobenzofuran-1(3H),4'-piperidine-1'-yl]-ethyl}-3,4-dihydro-1H-isoquinoline-2-carboxylic acid tert-butyl ester
15. 1-(1-{2-[6-Fluorospiro[isobenzofuran-1(3H),4'-piperidine-1'-yl]-ethyl}-3,4-dihydro-1H-isoquinolin-2-yl)-1-phenylmethanone
16. 1-(1-{2-[6-Fluorospiro[isobenzofuran-1(3H),4'-piperidine-1'-yl]-ethyl}-3,4-dihydro-1H-isoquinolin-2-yl)-1-p-tolylmethanone
17. 1-(1-{2-[6-Fluorospiro[isobenzofuran-1(3H),4'-piperidine-1'-yl]-ethyl}-3,4-dihydro-1H-isoquinolin-2-yl)-1-(2-methoxy-phenyl)methanone
18. 1-Cycloheptyl-1-(1-{2-[6-fluorospiro[isobenzofuran-1(3H),4'-piperidine-1'-yl]-ethyl}-3,4-dihydro-1H-isoquinolin-2-yl)methanone
19. 1-(2-Fluoro-phenyl)-1-(1-{2-[6-fluorospiro[isobenzofuran-1(3H),4'-piperidine-1'-yl]-ethyl}-3,4-dihydro-1H-isoquinolin-2-yl)methanone
20. 1-(2-Chloro-phenyl)-1-(1-{2-[6-fluorospiro[isobenzofuran-1(3H),4'-piperidine-1'-yl]-ethyl}-3,4-dihydro-1H-isoquinolin-2-yl)methanone
21. 1-(4-Fluoro-phenyl)-1-(1-{2-[6-fluorospiro[isobenzofuran-1(3H),4'-piperidine-1'-yl]-ethyl}-3,4-dihydro-1H-isoquinolin-2-yl)methanone
22. 1-(4-Chloro-phenyl)-1-(1-{2-[6-fluorospiro[isobenzofuran-1(3H),4'-piperidine-1'-yl]-ethyl}-3,4-dihydro-1H-isoquinolin-2-yl)methanone
23. 1-{2-[6-Fluorospiro[isobenzofuran-1(3H),4'-piperidine-1'-yl]-ethyl}-3,4-dihydro-1H-isoquinoline-2-carboxylic acid phenethyl amide
24. 1-(1-{2-[6-Fluorospiro[isobenzofuran-1(3H),4'-piperidine-1'-yl]-ethyl}-3,4-dihydro-1H-isoquinolin-2-yl)-1-(4-methoxy-phenyl)methanone
25. 1-(1-{2-[6-Fluorospiro[isobenzofuran-1(3H),4'-piperidine-1'-yl]-ethyl}-3,4-dihydro-1H-isoquinolin-2-yl)-3-phenyl-propan-1-one
26. 2-Ethyl-1-(1-{2-[6-fluorospiro[isobenzofuran-1(3H),4'-piperidine-1'-yl]-ethyl}-3,4-dihydro-1H-isoquinolin-2-yl)-butan-1-one
27. 1-(1-{2-[6-Fluorospiro[isobenzofuran-1(3H),4'-piperidine-1'-yl]-ethyl}-3,4-dihydro-1H-isoquinolin-2-yl)-1-(3-methoxy-phenyl)methanone
28. 1-(1-{2-[6-Fluorospiro[isobenzofuran-1(3H),4'-piperidine-1'-yl]-ethyl}-3,4-dihydro-1H-isoquinolin-2-yl)-2-phenylethanone
29. 3-Cyclohexyl-1-(1-{2-[6-fluorospiro[isobenzofuran-1(3H),4'-piperidine-1'-yl]-ethyl}-3,4-dihydro-1H-isoquinolin-2-yl)-propan-1-one
30. 2-(4-Fluoro-phenyl)-1-(1-{2-[6-fluorospiro[isobenzofuran-1(3H),4'-piperidine-1'-yl]-ethyl}-3,4-dihydro-1H-isoquinolin-2-yl)ethanone
31. 1-{2-[6-Fluorospiro[isobenzofuran-1(3H),4'-piperidine-1'-yl]-ethyl}-3,4-dihydro-1H-isoquinoline-2-carboxylic acid (3,4-dichloro-phenyl)amide
32. 1-Cyclopropyl-1-(1-{2-[6-fluorospiro[isobenzofuran-1(3H),4'-piperidine-1'-yl]-ethyl}-3,4-dihydro-1H-isoquinolin-2-yl)methanone
33. 1-(1-{2-[6-Fluorospiro[isobenzofuran-1 (3H),4'-piperidine-1'-yl]-ethyl}-3,4-dihydro-1H-isoquinolin-2-yl)-1-pyridin-3-yl-methanone
34. 1-[5-(4-Chloro-phenyl)-2-methyl-furan-3-yl]-1-(1-{2-[6-fluorospiro[isobenzofuran-1(3H),4'-piperidine-1'-yl]-ethyl}-3,4-dihydro-1H-isoquinolin-2-yl)methano
35. 2-(4-Chloro-phenyl)-1-(1-{2-[6-fluorospiro[isobenzofuran-1(3H),4'-piperidine-1'-yl]-ethyl}-3,4-dihydro-1H-isoquinolin-2-yl)ethanone
36. 1-(1-{2-[6-Fluorospiro[isobenzofuran-1(3H),4'-piperidine-1'-yl]-ethyl}-3,4-dihydro-1H-isoquinolin-2-yl)-2-methyl-propan-1-one
37. 1-{2-[6-Fluorospiro[isobenzofuran-1(3H),4'-piperidine-1'-yl]-ethyl}-3,4-dihydro-1H-isoquinoline-2-carboxylic acid (2-ethyl-phenyl)amide
38. N-[1-{2-[2-(1-Cycloheptyl-methanoyl)-1,2,3,4-tetrahydro-isoquinolin-1-yl]-ethyl}-4-(3-fluorophenyl)-piperidin-4-yl]acetamide
39. 1-Cyclopentyl-1-(1-{2-[6-fluoro-3-methylspiro[isobenzofuran-1(3H),4'-piperidin-1'-yl]]-ethyl}-3,4-dihydro-1H-isoquinolin-2-yl)methanone
40. 1-Cycloheptyl-1-{1-[1-acetyl-spiro[2,3-dihydro-1H-indol-3,4'-piperidin-1'-yl]ethyl]-3,4-dihydro-1H-isoquinolin-2-yl}methanone
41. N-(1-{2-[2-(1-Cycloheptyl-methanoyl)-1,2,3,4-tetrahydro-isoquinolin-1-yl]-ethyl}-4-phenylpiperidin-4-yl)acetamide 42. 1-Cycloheptyl-1-(1-{2-[6-fluorospiro[isobenzofuran-1(3H),4'-piperidine-1'-yl]-ethyl}-3,4-dihydro-6,7-dimethoxy-1H-isoquinolin-2-yl)methanone
43. 1-(4-Fluorophenyl)-1-(1-{2-[6-fluoro-3-methylspiro[isobenzofuran-1(3H),4'-piperidine-1'-yl]-ethyl}-3,4-dihydro-1H-isoquinolin-2-yl)methanone
44. 1-Cycloheptyl-1-(1-{2-[5-fluoro-1-methansulfonyl-spiro[2,3-dihydro-1H-indol-3,4'-piperidin-1'-yl]-ethyl}-3,4-dihydro-1H-isoquinolin-2-yl)methanone
45. 1-(1-{2-[2-(1-Cycloheptyl-methanoyl)-1,2,3,4-tetrahydro-isoquinolin-1-yl]-ethyl}-4-phenyl-piperidin-4-yl)-1-piperidin-1-ylmethanone
46. 1-(4-Fluorophenyl)-1-(1-{2-[5-fluoro-1-methansulfonyl-spiro[2,3-dihydro-1H-indol-3,4'-piperidin-1'-yl]-ethyl}-3,4-dihydro-1H-isoquinolin-2-yl)methanone
47. 1-Cycloheptyl-1-(1-{2-[4-(2-methyl-1H-indol-3-yl)-piperidin-1-yl]-ethyl}-3,4-dihydro-1H-isoquinolin-2-yl)methanone
48. 1-Cycloheptyl-1-(1-{2-[4-(3-trifluoromethyl-phenyl)-piperidin-1-yl]-ethyl}-3,4-dihydro-1H-isoquinolin-2-yl)methanone
49. 1-Cyclopentyl-1-(1-{2-[6-fluoro-3-methylspiro[isobenzofuran-1(3H),4'-piperidine-1'-yl]-ethyl}-3,4-dihydro-6,7-dimethoxy-1H-isoquinolin-2-yl)methanone
50. 1-Cyclopentyl-1-{1-[spiro[2,3-dihydro-1H-indol-3,4'-piperidin-1'-yl]ethyl]-3,4-dihydro-1H-isoquinolin-2-yl}methanone
51. 1-Cyclopentyl-1-(1-{2-[5-fluoro-1-methansulfonyl-spiro[2,3-dihydro-1H-indol-3,4'-piperidin-1'-yl]-ethyl}-3,4-dihydro-1H-isoquinolin-2-yl)methanone
52. 1-(4-Fluorophenyl)-1-(1-{2-[6-fluoro-3-methylspiro[isobenzofuran-1(3H),4'-piperidine-1'-yl]-ethyl}-3,4-dihydro-6,7-dimethoxy-1H-isoquinolin-2-yl)methanone
53. 1-(2-Fluorophenyl)-1-(1-{2-[6-fluorospiro[isobenzofuran-1(3H),4'-piperidine-1'-yl]-ethyl}-3,4-dihydro-1H-isoquinolin-2-yl)methanone
54. 1-Cycloheptyl-1-(1-{2-[spiro[isobenzofuran-1(3H),4'-piperidine-1'-yl]-ethyl}-3,4-dihydro-1H-isoquinolin-2-yl)methanone
55. 1-Cycloheptyl-1-(1-{2-[6-fluoro-3-methylspiro[isobenzofuran-1(3H),4'-piperidine-1'-yl]-ethyl}-3,4-dihydro-6,7-dimethoxy-1H-isoquinolin-2-yl)methanone
56. 1-(1-{2-[4-(4-Chloro-phenyl)-piperidin-1-yl]-ethyl}-3,4-dihydro-1H-isoquinolin-2-yl)-1-cycloheptylmethanone
57. 1-Cyclopentyl-1-(1-{2-[5-isopropylspiro[isobenzofuran-1(3H),4'-piperidine-1'-yl]-ethyl}-3,4-dihydro-1H-isoquinolin-2-yl)methanone
58. N-[1-{2-[2-(1-Cyclopentyl-methanoyl)-1,2,3,4-tetrahydro-isoquinolin-1-yl]-ethyl}-4-(3-fluorophenyl)-piperidin-4-yl]acetamide
59. 1-Cycloheptyl-1-{1-[2-(4-phenylpiperidin-1-yl)-ethyl]-3,4-dihydro-1H-isoquinolin-2-yl}methanone
60. 1-Cycloheptyl-1-(1-{2-[6-fluoro-3-methylspiro[isobenzofuran-1(3H),4'-piperidine-1'-yl]-ethyl}-3,4-dihydro-1H-isoquinolin-2-yl)methanone
61. 1-Cyclopentyl-1-(1-{2-[4-(3-trifluoromethylphenyl)piperidin-1-yl]-ethyl}-3,4-dihydro-1H-isoquinolin-2-yl)methanone
62. 1-Cyclopentyl-1-(1-{2-[6-fluorospiro[isobenzofuran-1(3H),4'-piperidine-1'-yl]-ethyl}-3,4-dihydro-6,7-dimethoxy-1H-isoquinolin-2-yl)methanone
63. 1-(4-Fluorophenyl)-1-(1-{2-[6-fluorospiro[isobenzofuran-1(3H),4'-piperidine-1'-yl]-ethyl}-3,4-dihydro-6,7-dimethoxy-1H-isoquinolin-2-yl)methanone
64. 1-(1-{2-[4-(6-Fluorobenzo[d]isoxazol-3-yl)-piperidin-1-yl]-ethyl}-3,4-dihydro-1H-isoquinolin-2-yl)-1-(4-fluorophenyl)methanone
65. 1-[1-(2-{2-[1-(4-Fluorophenyl)-methanoyl]-1,2,3,4-tetrahydro-isoquinolin-1-yl]-ethyl)-4-phenylpiperidin-4-yl]-1-piperidin-1-yl-methanone
66. 1-Cyclopentyl-1-(1-{2-[4-(3-fluoro-phenyl)-piperidin-1-yl]-ethyl}-3,4-dihydro-1H-isoquinolin-2-yl)methanone
67. 8-{2-[2-(1-Cycloheptyl-methanoyl)-1,2,3,4-tetrahydro-isoquinolin-1-yl]-ethyl}-1-phenyl-1,3,8-triaza-spiro[4.5]decan-4-one
68. 1-Cycloheptyl-1-(1-{2-[6-trifluoromethylspiro[isobenzofuran-1(3H),4'-piperidine-1'-yl]-ethyl}-3,4-dihydro-6,7-dimethoxy-1H-isoquinolin-2-yl)methanone
69. 1-[1-(2-{2-[1-(2-Fluoro-phenyl)-methanoyl]-1,2,3,4-tetrahydro-isoquinolin-1-yl]-ethyl)-4-phenyl-piperidin-4-yl]-1-(4-methyl-piperazin-1-yl)methanone
70. 1-{2-[2-(1-Cycloheptyl-methanoyl)-1,2,3,4-tetrahydro-isoquinolin-1-yl]-ethyl}-4-phenyl-piperidine-4-carboxylic acid ethyl ester
71. 1-(1-{2-[2-(1-Cycloheptyl-methanoyl)-1,2,3,4-tetrahydro-isoquinolin-1-yl]-ethyl}-4-phenyl-piperidin-4-yl)-ethanone
72. 1-Cyclopentyl-1-(1-{2-[6-trifluoromethylspiro[isobenzofuran-1(3H),4'-piperidine-1'-yl]-ethyl}-3,4-dihydro-6,7-dimethoxy-1H-isoquinolin-2-yl)methanone
73. 1-Cyclopentyl-1-(1-{2-[4-(2-methyl-1H-indol-3-yl)-piperidin-1-yl]-ethyl}-3,4-dihydro-1H-isoquinolin-2-yl)methanone
74. 1-(1-{2-[2-(1-Cyclopentyl-methanoyl)-1,2,3,4-tetrahydro-isoquinolin-1-yl]-ethyl}-4-phenyl-piperidin-4-yl)ethanone
75. 1-(4-Fluorophenyl)-1-(1-{2-[6-trifluoromethylspiro[isobenzofuran-1(3H),4'-piperidine-1'-yl]-ethyl}-3,4-dihydro-6,7-dimethoxy-1H-isoquinolin-2-yl)methanone
76. 1-(1-{2-[4-(4-Chloro-phenyl)-piperidin-1-yl]-ethyl}-3,4-dihydro-1H-isoquinolin-2-yl)-1-(4-fluoro-phenyl)methanone
77. 1-(1-{2-[2-(1-Cycloheptyl-methanoyl)-1,2,3,4-tetrahydro-isoquinolin-1-yl]-ethyl}-piperidin-4-yl)-1-(4-fluoro-phenyl)methanone
78. 1-(1-{2-[2-(1-Cycloheptyl-methanoyl)-6,7-dimethoxy-1,2,3,4-tetrahydro-isoquinolin-1-yl]-ethyl}-4-phenyl-piperidin-4-yl)-1-(4-methyl-piperazin-1-yl)methanone
79. 1-(1-{2-[4-(4-Chloro-phenyl)-piperidin-1-yl]-ethyl}-3,4-dihydro-1H-isoquinolin-2-yl)-1-cyclopentylmethanone
80. 1-(4-Fluoro-phenyl)-1-(1-{2-[4-(3-trifluoromethyl-phenyl)-piperidin-1-yl]-ethyl}-3,4-dihydro-1H-isoquinolin-2-yl)methanone
81. 1-(4-Fluorophenyl)-1-(1-{2-[piro[isobenzofuran-1(3H),4'-piperidine-1'-yl]-ethyl}-3,4-dihydro-1H-isoquinolin-2-yl)methanone
82. 1-Cyclopentyl-1-(1-{2-[4-fluorospiro[isobenzofuran-1(3H),4'-piperidine-1'-yl]-ethyl}-3,4-dihydro-1H-isoquinolin-2-yl)methanone
83. 1-(2-Fluorophenyl)-1-(1-{2-[6-fluoro-3-methylspiro[isobenzofuran-1(3H),4'-piperidine-1'-yl]-ethyl}-3,4-dihydro-6,7-dimethoxy-1H-isoquinolin-2-yl)methanone
84. N-[4-(3-Fluoro-phenyl)-1-(2-{2-[1-(4-fluoro-phenyl)-methanoyl]-1,2,3,4-tetrahydro-isoquinolin-1-yl}-ethyl)-piperidin-4-yl]-acetamide
85. 1-(2-Fluorophenyl)-1-{1-[spiro[2,3-dihydro-1H-indol-3,4'-piperidin-1'-yl]ethyl]-3,4-dihydro-1H-isoquinolin-2-yl}methanone
86. 1-Cycloheptyl-1-(1-{2-[5-fluoro-1-methansulfonyl-spiro[2,3-dihydro-H-indol-3,4'-piperidin-1'-yl]-ethyl}-3,4-dihydro-6,7-dimethoxy-1H-isoquinolin-2-yl)methanone 87. 1-(1-{2-[2-(1-Cycloheptyl-methanoyl)-6,7-dimethoxy-1,2,3,4-tetrahydro-isoquinolin-1-yl]-ethyl}-4-phenyl-piperidin-4-yl)-1-piperidin-1-ylmethanone
88. 1-{1-[2-(4-Benzyl-piperidin-1-yl)-ethyl-3,4-dihydro-H-isoquinolin-2-yl}-1-cycloheptylmethanone
89. 1-(2-Fluorophenyl)-1-(1-{2-[6-trifluoromethylspiro[isobenzofuran-1(3H),4'-piperidine-1'-yl]-ethyl}-3,4-dihydro-6,7-dimethoxy-1H-isoquinolin-2-yl)methanone
90. 1-(1-{2-[(Chloro-trifluoromethyl-phenyl)-hydroxy-piperidin-1-yl]-ethyl}-6,7-dimethoxy-3,4-dihydro-1H-isoquinolin-2-yl)-1-cycloheptylmethanone
91. 1-(1-{2-[4-(4-Chloro-phenyl)-4-hydroxy-piperidin-1-yl]-ethyl}-6,7-dimethoxy-3,4-dihydro-1H-isoquinolin-2-yl)-1-cycloheptylmethanone
92. 1-Cycloheptyl-1-(1-{2-[4-(2-isopropoxy-phenyl)-piperidin-1-yl]-ethyl}-3,4-dihydro-1H-isoquinolin-2-yl)methanone
93. 1-(1-{2-[4-(7-Chloro-1H-indol-3-yl)-piperidin-1-yl]-ethyl}-3,4-dihydro-1H-isoquinolin-2-yl)-1-cyclopentyl-methanone
94. 1-Cyclopentyl-1-(1-{2-[4-(2,3-dihydro-benzofuran-7-yl)-piperidin-1-yl]-ethyl}-3,4-dihydro-1H-isoquinolin-2-yl)methanone
95. 1-(1-{2-[4-(2,3-Dihydro-benzofuran-7-yl)-piperidin-1-yl]-ethyl}-3,4-dihydro-1H-isoquinolin-2-yl)-1-(4-fluoro-phenyl)methanone
96. N-[1-{2-[2-(1-Cycloheptyl-methanoyl)-6,7-dimethoxy-1,2,3,4-tetrahydro-isoquinolin-1-yl]-ethyl}-4-(3-fluoro-phenyl)-piperidin-4-yl]-acetamide
97. 1-(4-Fluoro-phenyl)-1-{1-[2-(4-phenyl-piperidin-1-yl)-ethyl]-3,4-dihydro-1H-isoquinolin-2-yl}methanone
98. 1-(1-{2-[4-(6-Chloro-1H-indol-3-yl)-piperidin-1-yl]-ethyl}-3,4-dihydro-1H-isoquinolin-2-yl)-1-(4-fluoro-phenyl)methanone
99. 1-(4-Fluoro-phenyl)-1-(1-{2-[4-(3-fluoro-phenyl)-piperidin-1-yl]-ethyl}-3,4-dihydro-1H-isoquinolin-2-yl)methanone
100. 1-Cycloheptyl-1-{1-[spiro[2,3-dihydro-1H-indol-3,4'-piperidin-1'-yl]ethyl]-3,4-dihydro-6,7-dimethoxy-1H-isoquinolin-2-yl}methanone
101. N-(1-{2-[2-(1-Cyclopentyl-methanoyl)-1,2,3,4-tetrahydro-isoquinolin-1-yl]-ethyl}-4-phenyl-piperidin-4-yl)acetamide
102. 1-(1-{2-[4-(6-Fluoro-benzo[d]isoxazol-3-yl)-piperidin-1-yl]-ethyl}-3,4-dihydro-1H-isoquinolin-2-yl)-1-(2-fluoro-phenyl)methanone
103. 1-cycloheptyl-1-(1-{2-[spiro[isobenzofuran-1(3H),4'-piperidine-1'-yl]-ethyl}-3,4-dihydro-6,7-dimethoxy-1H-isoquinolin-2-yl)methanone
104. 1-{2-[2-(1-Cyclopentyl-methanoyl)-1,2,3,4-tetrahydro-isoquinolin-1-yl]-ethyl}-4-phenyl-piperidine-4-carboxylic acid ethyl ester
105. 1-(1-{2-[4-(4-Dimethylamino-phenyl)-piperidin-1-yl]-ethyl}-3,4-dihydro-1H-isoquinolin-2-yl)-1-(4-fluoro-phenyl)methanone
106. 1-Cyclopentyl-1-(1-{2-[4-(4-isopropyl-phenyl)-piperidin-1-yl]-ethyl}-3,4-dihydro-1H-isoquinolin-2-yl)methanone
107. 1-[1-(2-{2-[1-(4-Fluoro-phenyl)-methanoyl]-1,2,3,4-tetrahydro-isoquiinolin-1-yl}-ethyl)-4-phenyl-piperidin-4-yl]ethanone
108. 1-[1-(2-{2-[1-(2-Fluoro-phenyl)-methanoyl]-1,2,3,4-tetrahydro-isoquinolin-1-yl}-ethyl)-4-phenyl-piperidin-4-yl]ethanone
109. 1-[1-(2-{2-[1-(2-Fluoro-phenyl)-methanoyl]-1,2,3,4-tetrahydro-isoquinolin-1-yl}-ethyl)-4-phenyl-piperidin-4-yl]-1-piperidin-1-yl-methanone
110. 1-Cyclopentyl-1-{1-[2-(4-phenyl-piperidin-1-yl)-ethyl]-3,4-dihydro-1H-isoquinolin-2-yl}methanone
111. 1-(2-Fluorophenyl)-1-(1-{2-[6-fluorospiro[isobenzofuran-1(3H),4'-piperidine-1'-yl]-ethyl}-3,4-dihydro-6,7-dimethoxy-1H-isoquinolin-2-yl)methanone
112. 1-(4-Fluoro-phenyl)-1-(1-{2-[5,6-difluorospiro[benzofuran-1(3H),4'-piperidine-1'-yl]-ethyl}-3,4-dihydro-1H-isoquinolin-2-yl)-methanone
113. 1-(4-Fluorophenyl)-1-({2-[6-fluorospiro[benzofuran-1(3H),4'-piperidine-1'-yl]-ethyl}-3,4-dihydro-1H-isoquinolin-2-yl)methanone
114. 3,3-Dimethyl-[1-{2-[spiro(5-fluoro-benzofuran-2H-3,4'-piperidine-1'-yl)-]ethyl}-3,4-dihydro-1H-isoquinoline-2-yl]-butan-1-one
115. Cyclohexyl-[1-{2-[spiro(5-fluoro-benzofuran-2H-3,4'-piperidine-1'-yl)-]ethyl}-3,4-dihydro-1H-isoquinoline-2-yl]-methanone
116. Cyclohexyl-(1-{2-[spiro(5-methyl-isobenzofuran-3H-1,4'-piperidine-1'-yl)-]ethyl}-3,4-dihydro-1H-isoquinolin-2-yl)-methanone
117. Cyclohexyl-[1-{2-[spiro(benzofuran-3H-1,4'-piperidine-1'-yl)-]ethyl}-3,4-dihydro-1H-isoquinoline-2-yl]-methanone
118. Cyclohexyl-(1-{2-[4-(2-methyl-1H-indol-3-yl)-piperidin-1-yl]-ethyl}-3,4-dihydro-1H-isoquinolin-2-yl)-methanone
119. N-{1-[2-(2-Cyclohexanecarbonyl-1,2,3,4-tetrahydro-isoquinolin-1-yl)-ethyl]-4-phenyl-piperidin-4-yl}-acetamide
120. 3,3-Dimethyl-1-(1-{2-[4-(3-trifluoromethyl-phenyl)-piperidin-1-yl]-ethyl}-3,4-dihydro-1H-isoquinolin-2-yl)-butan-1-one
121. Cyclohexyl-(1-{2-[4-(3-trifluoromethyl-phenyl)-piperidin-1-yl]-ethyl}-3,4-dihydro-1H-isoquinolin-2-yl)-methanone
122. Cyclohexyl-(1-{2-[4-(4-dimethylamino-phenyl)-piperidin-1-yl]-ethyl}-3,4-dihydro-1H-isoquinolin-2-yl)-methanone
123. 3-Phenyl-[1-{2-[spiro(5-fluor-benzofuran-2H-3,4'-piperidine-1'-yl)-]ethyl}-3,4-dihydro-1H-isoquinoline-2-yl]-propanone
124. (1-{2-[4-(4-Chloro-3-trifluoromethyl-phenyl)-4-hydroxy-piperidin-1-yl]-ethyl}-6,7-dimethoxy-3,4-dihydro-1H-isoquinolin-2-yl)-cyclohexyl-methanone
125. 2-Phenoxy-[1-{2-[spiro(5-fluor-benzofuran-2H-3,4'-piperidine-1'-yl)-]ethyl}-3,4-dihydro-1H-isoquinoline-2-yl]-ethan-1-one
126. Benzo[1,2,5]oxadiazol-5-yl-(1-{2-[spiro(5-methyl-isobenzofuran-3H-1,4'-piperidine-1'-yl)-]ethyl}-3,4-dihydro-1H-isoquinolin-2-yl)-methanone
127. Cyclohexyl-(1-{2-[4-(4-isopropyl-phenyl)-piperidin-1-yl]-ethyl}-3,4-dihydro-1H-isoquinolin-2-yl)-methanone
128. 2-Propyl-[1-{2-[spiro(5-fluor-benzofuran-2H-3,4'-piperidine-1'-yl)-]ethyl}-3,4-dihydro-1H-isoquinoline-2-yl]-pentan-1-one
129. 2,2-Dimethyl-3-chlor-[1-{2-[spiro(5-fluor-benzofuran-2H-3,4'-piperidine-1'-yl)-]ethyl}-3,4-dihydro-1H-isoquinoline-2-yl]-propan-1-one
130. Cyclohexyl-(1-{2-[4-(2,3-dihydro-benzofuran-7-yl)-piperidin-1-yl]-ethyl}-3,4-dihydro-1H-isoquinolin-2-yl)-methanone
131. 3,3-Dimethyl-(1-{2-[spiro(5-methyl-isobenzofuran-3H-1,4'-piperidine-1'-yl)-]ethyl}-3,4-dihydro-1H-isoquinolin-2-yl)-butan-1-one
132. Benzo[1,2,5]oxadiazol-5-yl-(1-{2-[4-(3-trifluoromethyl-phenyl)-piperidin-1-yl]-ethyl}-3,4-dihydro-1H-isoquinolin-2-yl)-methanone 133. 2-Ethyl-1-(1-{2-[4-(3-trifluoromethyl-phenyl)-piperidin-1-yl]-ethyl}-3,4-dihydro-1H-isoquinolin-2-yl)-butan-1-one
134. 2-Benzyloxy-(1-{2-[spiro(5-methyl-isobenzofuran-3H-1,4'-piperidine-1'-yl)-]ethyl}-3,4-dihydro-1H-isoquinolin-2-yl)-ethan-1-one
135. Benzo[1,2,5]oxadiazol-5-yl-[1-{2-[spiro(5-fluor-benzofuran-2H-3,4'-piperidine-1'-yl)-]ethyl}-3,4-dihydro-1H-isoquinoline-2-yl]-methanone
136. (1-{2-[4-(4-Chloro-phenyl)-piperidin-1-yl]-ethyl}-3,4-dihydro-1H-isoquinolin-2-yl)-cyclohexyl-methanone
137. 1-(1-{2-[4-(4-Chloro-phenyl)-piperidin-1-yl]-ethyl}-3,4-dihydro-1H-isoquinolin-2-yl)-3,3-dimethyl-butan-1-one
138. 3,5,5-Trimethyl-[1-{2-[spiro(5-fluor-benzofuran-2H-3,4'-piperidine-1'-yl)-]ethyl}-3,4-dihydro-1H-isoquinoline-2-yl]-hexan-1-one
139. 3,5,5-Trimethyl-(1-{2-[spiro(5-methyl-isobenzofuran-3H-1,4'-piperidine-1'-yl)-]ethyl}-3,4-dihydro-1H-isoquinolin-2-yl)-hexan-1-one
140. 2-Phenoxy-(1-{2-[spiro(5-methyl-isobenzofuran-3H-1,4'-piperidine-1'-yl)-]ethyl}-3,4-dihydro-1H-isoquinolin-2-yl)-ethan-1-one
141. (1-{2-[4-(4-Chloro-phenyl)-piperidin-1-yl]-ethyl}-3,4-dihydro-1H-isoquinolin-2-yl)-(2,2-dichloro-cyclopropyl)-methanone
142. 2-Benzyloxy-[1-{2-[spiro(5-fluor-benzofuran-2H-3,4'-piperidine-1'-yl)-]ethyl}-3,4-dihydro-1H-isoquinoline-2-yl]-ethan-1-one
143. 1-(1-{2-[4-(4-Chloro-3-trifluoromethyl-phenyl)-4-hydroxy-piperidin-1-yl]-ethyl}-6,7-dimethoxy-3,4-dihydro-1H-isoquinolin-2-yl)-3,3-dimethyl-butan-1-one
144. 1-(1-{2-[4-(2,3-Dihydro-benzofuran-7-yl)-piperidin-1-yl]-ethyl}-3,4-dihydro-1H-isoquinolin-2-yl)-3,3-dimethyl-butan-1-one
145. 3,5,5-Trimethyl-1-(1-{2-[4-(3-trifluoromethyl-phenyl)-piperidin-1-yl]-ethyl}-3,4-dihydro-1H-isoquinolin-2-yl)-hexan-1-one
146. 2,2-Dimethyl-[1-{2-[spiro(5-fluor-benzofuran-2H-3,4'-piperidine-1'-yl)-]ethyl}-3,4-dihydro-1H-isoquinoline-2-yl]-propan-1-one
147. 3-Cyclohexyl-1-(1-{2-[4-(3-trifluoromethyl-phenyl)-piperidin-1-yl]-ethyl}-3,4-dihydro-1H-isoquinolin-2-yl)-propan-1-one
148. Furan-2-yl-[1-{2-[spiro(5-fluor-benzofuran-2H-3,4'-piperidine-1'-yl)-]ethyl}-3,4-dihydro-1H-isoquinoline-2-yl]-methanone
149. N-(4-Phenyl-1-{2-[2-(3,5,5-trimethyl-hexanoyl)-1,2,3,4-tetrahydro-isoquinolin-1-yl]-ethyl}-piperidin-4-yl)-acetamide
150. Quinoxalin-2-yl-[1-{2-[spiro(5-fluor-benzofuran-2H-3,4'-piperidine-1'-yl)-]ethyl}-3,4-dihydro-1H-isoquinoline-2-yl]-methanone
151. 3-Cyclohexyl-[1-{2-[spiro(5-fluor-benzofuran-2H-3,4'-piperidine-1'-yl)-]ethyl}-3,4-dihydro-1H-isoquinoline-2-yl]-propan-1-one
152. Benzo[1,2,5]oxadiazol-5-yl-(1-{2-[4-(2,3-dihydro-benzofuran-7-yl)-piperidin-1-yl]-ethyl}-3,4-dihydro-1H-isoquinolin-2-yl)-methanone
153. Benzo[1,2,5]oxadiazol-5-yl-(1-{2-[4-(2-methyl-1H-indol-3-yl)-piperidin-1-yl]-ethyl}-3,4-dihydro-1H-isoquinolin-2-yl)-methanone
154. (Tetrahydro-pyran-4-yl)-(1-{2-[4-(3-trifluoromethyl-phenyl)-piperidin-1-yl]-ethyl}-3,4-dihydro-1H-isoquinolin-2-yl)-methanone
155. 2-Propyl-1-(1-{2-[4-(3-trifluoromethyl-phenyl)-piperidin-1-yl]-ethyl}-3,4-dihydro-1H-isoquinolin-2-yl)-pentan-1-one
156. 2-Ethyl-[1-{2-[spiro(5-fluor-benzofuran-2H-3,4'-piperidine-1'-yl)-]ethyl}-3,4-dihydro-1H-isoquinoline-2-yl]-butan-1-one
157. 3-Phenyl-1-(1-{2-[4-(3-trifluoromethyl-phenyl)-piperidin-1-yl]-ethyl}-3,4-dihydro-1H-isoquinolin-2-yl)-propan-1-one
158. 3,3-Dimethyl-1-(1-{2-[4-(2-methyl-1H-indol-3-yl)-piperidin-1-yl]-ethyl}-3,4-dihydro-1H-isoquinolin-2-yl)-butan-1-one
159. (1-{2-[4-(4-Chloro-3-trifluoromethyl-phenyl)-4-hydroxy-piperidin-1-yl]-ethyl}-6,7-dimethoxy-3,4-dihydro-1H-isoquinolin-2-yl)-(2,2-dichloro-cyclopropyl)-methanone
160. 1,2,3,4-tetrahydro-naphthalene-2-yl-(1-{2-[spiro(5-methyl-isobenzofuran-3H-1,4'-piperidine-1'-yl)-]ethyl}-3,4-dihydro-1H-isoquinolin-2-yl)-methanone
161. (4-Methylsulfanyl-phenyl)-(1-{2-[4-(3-trifluoromethyl-phenyl)-piperidin-1-yl]-ethyl}-3,4-dihydro-1H-isoquinolin-2-yl)-methanone
162. 3,5,5-Trimethyl-1(1-{2-[4-(2-methyl-1H-indol-3-yl)-piperidin-1-yl]-ethyl}-3,4-dihydro-1H-isoquinolin-2-yl)-hexan-1-one
163. 3-Phenyl-(1-{2-[spiro(5-methyl-isobenzofuran-3H-1,4'-piperidine-1'-yl)-]ethyl}-3,4-dihydro-1H-isoquinolin-2-yl)-propan-1-one
164. Furan-2-yl-(1-{2-[4-(3-trifluoromethyl-phenyl)-piperidin-1-yl]-ethyl}-3,4-dihydro-1H-isoquinolin-2-yl)-methanone
165. 2-Benzyloxy-1-(1-{2-[4-(2-methyl-1H-indol-3-yl)-piperidin-1-yl]-ethyl}-3,4-dihydro-1H-isoquinolin-2-yl)-ethanone
166. 1-(1-{2-[4-(4-Chloro-phenyl)-piperidin-1-yl]-ethyl}-3,4-dihydro-1H-isoquinolin-2-yl)-2-phenoxy-ethanone
167. Quinoxalin-2-yl-(1-{2-[spiro(5-methyl-isobenzofuran-3H-1,4'-piperidine-1'-yl)-]ethyl}-3,4-dihydro-1H-isoquinolin-2-yl)-methanone
168. 2,2-Dimethyl-1-(1-{2-[4-(3-trifluoromethyl-phenyl)-piperidin-1-yl]-ethyl}-3,4-dihydro-1H-isoquinolin-2-yl)-propan-1-one
169. (2,2-Dichloro-cyclopropyl)-(1-{2-[4-(3-trifluoromethyl-phenyl)-piperidin-1-yl]-ethyl}-3,4-dihydro-1H-isoquinolin-2-yl)-methanone
170. 4-Methylsulfanyl-phenyl-(1-{2-[spiro(5-methyl-isobenzofuran-3H-1,4'-piperidine-1'-yl)-]ethyl}-3,4-dihydro-1H-isoquinolin-2-yl)-methanone
171. (2,2-Dichloro-cyclopropyl)-(1-{2-[4-(2,3-dihydro-benzofuran-7-yl)-piperidin-1-yl]-ethyl}-3,4-dihydro-1H-isoquinolin-2-yl)-methanone
172. 1-(1-{2-[4-(4-Isopropyl-phenyl)-piperidin-1-yl]-ethyl}-3,4-dihydro-1H-isoquinolin-2-yl)-3,5,5-trimethyl-hexan-1-one
173. 2,2-Dichloro-cyclopropyl-(1-{2-[spiro(isobenzofuran-3H-1,4'-piperidine-1'-yl)-]ethyl}-3,4-dihydro-1H-isoquinolin-2-yl)-methanone
174. N-(4-Phenyl-1-{2-[2-(1,2,3,4-tetrahydro-naphthalene-2-carbonyl)-1,2,3,4-tetrahydro-isoquinolin-1-yl]-ethyl}-piperidin-4-yl)-acetamide
175. Benzo[1,2,5]oxadiazol-5-yl-(1-{2-[4-(4-chloro-phenyl)-piperidin-1-yl]-ethyl}-3,4-dihydro-1H-isoquinolin-2-yl)-methanone
176. N-(1-{2-[2-(3,3-Dimethyl-butyryl)-1,2,3,4-tetrahydro-isoquinolin-1-yl]-ethyl}-4-phenyl-piperidin-4-yl)-acetamide 177. 3-Chloro-2,2-dimethyl-1-(1-{2-[4-(3-trifluoromethyl-phenyl)-piperidin-1-yl]-ethyl}-3,4-dihydro-1H-isoquinolin-2-yl)-propan-1-one
178. Tetrahydro-pyran-4-yl-[1-{2-[spiro(5-fluor-benzofuran-2H-3,4'-piperidine-1'-yl)-]ethyl}-3,4-dihydro-1H-isoquinoline-2-yl]-butan-1-one The following compounds were made as enantiomers by method B starting from Enantiomer 2 of the corresponding amines of formula V. Analytical data are shown in table 1.

Compound

179. N-(4-(3-Fluoro-phenyl)-1-{2-[2-(2-methoxy-benzoyl)-1,2,3,4-tetrahydro-isoquinolin-1-yl]-ethyl}-piperidin-4-yl)acetamide (Enantiomer)
180. N-(4-(3-Fluoro-phenyl)-1-{2-[2-(2-methoxy-benzoyl)-1,2,3,4-tetrahydro-isoquinolin-1-yl]-ethyl}-piperidin-4-yl)acetamide (Enantiomer)
181. N-[1-{2-[2-(4-Chloro-benzoyl)-1,2,3,4-tetrahydro-isoquinolin-1-yl]-ethyl}-4-(3-fluoro-phenyl)-piperidin-4-yl]-acetamide (Enantiomer)
182. N-[1-{2-[2-(4-Bromo-benzoyl)-1,2,3,4-tetrahydro-isoquinolin-1-yl]-ethyl}-4-(3-fluoro-phenyl)-piperidin-4-yl]-acetamide (Enantiomer)
183. N-[1-{2-[2-(4-Fluoro-benzoyl)-1,2,3,4-tetrahydro-isoquinolin-1-yl]-ethyl}-4-(3-fluoro-phenyl)-piperidin-4-yl]-acetamide (Enantiomer)
184. N-(4-(3-Fluoro-phenyl)-1-{2-[2-(4-isopropyl-benzoyl)-1,2,3,4-tetrahydro-isoquinolin-1-yl]-ethyl}-piperidin-4-yl)acetamide (Enantiomer)
185. N-(4-(3-Fluoro-phenyl)-1-{2-[2-(4-methyl-benzoyl)-1,2,3,4-tetrahydro-isoquinolin-1-yl]-ethyl}-piperidin-4-yl)acetamide (Enantiomer)
186. N-[1-{2-[2-(3-Chloro-benzoyl)-1,2,3,4-tetrahydro-isoquinolin-1-yl]-ethyl}-4-(3-fluoro-phenyl)-piperidin-4-yl]-acetamide (Enantiomer)
187. N-[1-{2-[2-(2-Bromo-benzoyl)-1,2,3,4-tetrahydro-isoquinolin-1-yl]-ethyl}-4-(3-fluoro-phenyl)-piperidin-4-yl]-acetamide (Enantiomer)
188. N-(1-{2-[2-(4-Bromo-benzoyl)-1,2,3,4-tetrahydro-isoquinolin-1-yl]-ethyl}-4-phenyl-piperidin-4-yl)acetamide (Enantiomer)
189. N-(1-{2-[2-(2,4-Dichloro-benzoyl)-1,2,3,4-tetrahydro-isoquinolin-1-yl]-ethyl}-4-phenyl-piperidin-4-yl)acetamide (Enantiomer)
190. N-[1-{2-[2-(2,4-Dichloro-benzoyl)-1,2,3,4-tetrahydro-isoquinolin-1-yl]-ethyl}-4-(3-fluoro-phenyl)-piperidin-4-yl]-acetamide (Enantiomer)
191. N-[1-{2-[2-(Benzo[1,2,5]oxadiazole-5-carbonyl)-1,2,3,4-tetrahydro-isoquinolin-1-yl]-ethyl}-4-(3-fluoro-phenyl)-piperidin-4-yl]-acetamide (Enantiomer)
192. N-(4-(3-Fluoro-phenyl)-1-{2-[2-(naphthalene-1-carbonyl)-1,2,3,4-tetrahydro-isoquinolin-1-yl]-ethyl}-piperidin-4-yl)acetamide (Enantiomer)
193. N-[1-[2-(2-Cyclopentanecarbonyl-1,2,3,4-tetrahydro-isoquinolin-1-yl)-ethyl]-4-(3-fluoro-phenyl)-piperidin-4-yl]-acetamide (Enantiomer)
194. N-(1-{2-[2-(4-Chloro-benzoyl)-1,2,3,4-tetrahydro-isoquinolin-1-yl]-ethyl}-4-phenyl-piperidin-4-yl)acetamide (Enantiomer)
195. N-[1-{2-[2-(Benzo[b]thiophene-3-carbonyl)-1,2,3,4-tetrahydro-isoquinolin-1-yl]-ethyl}-4-(3-fluoro-phenyl)-piperidin-4-yl]-acetamide (Enantiomer)
196. N-[1-{2-[2-(6-Fluoro-4H-benzo[1,3]dioxine-8-carbonyl)-1,2,3,4-tetrahydro-isoquinolin-1-yl]-ethyl}-4-(3-fluoro-phenyl)-piperidin-4-yl]-acetamide (Enantiomer)
197. N-[1-{2-[2-(3-Bromo-benzoyl)-1,2,3,4-tetrahydro-isoquinolin-1-yl]-ethyl}-4-(3-fluoro-phenyl)-piperidin-4-yl]-acetamide (Enantiomer)
198. N-[1-{2-[2-(2-Fluoro-benzoyl)-1,2,3,4-tetrahydro-isoquinolin-1-yl]-ethyl}-4-(3-fluoro-phenyl)-piperidin-4-yl]-acetamide (Enantiomer)
199. N-(1-{2-[2-(4-Methyl-benzoyl)-1,2,3,4-tetrahydro-isoquinolin-1-yl]-ethyl}-4-phenyl-piperidin-4-yl)acetamide (Enantiomer)
200. N-[1-{2-[2-(2-Chloro-benzoyl)-1,2,3,4-tetrahydro-isoquinolin-1-yl]-ethyl}-4-(3-fluoro-phenyl)-piperidin-4-yl]-acetamide (Enantiomer)
201. N-(4-(3-Fluoro-phenyl)-1-{2-[2-(4-methoxy-benzoyl)-1,2,3,4-tetrahydro-isoquinolin-1-yl]-ethyl}-piperidin-4-yl)acetamide (Enantiomer)
202. N-(1-{2-[2-(3-Chloro-benzoyl)-1,2,3,4-tetrahydro-isoquinolin-1-yl]-ethyl}-4-phenyl-piperidin-4-yl)acetamide (Enantiomer)
203. N-(1-{2-[2-(4-Fluoro-benzoyl)-1,2,3,4-tetrahydro-isoquinolin-1-yl]-ethyl}-4-phenyl-piperidin-4-yl)acetamide (Enantiomer)
204. N-{1-[2-(2-Cycloheptanecarbonyl-1,2,3,4-tetrahydro-isoquinolin-1-yl)-ethyl]-4-phenyl-piperidin-4-yl}-acetamide (Enantiomer)
205. N-(1-{2-[2-(3-Bromo-benzoyl)-1,2,3,4-tetrahydro-isoquinolin-1-yl]-ethyl}-4-phenyl-piperidin-4-yl)acetamide (Enantiomer)
206. 2-N-(4-(3-Fluoro-phenyl)-1-{2-[2-(3-methoxy-benzoyl)-1,2,3,4-tetrahydro-isoquinolin-1-yl]-ethyl}-piperidin-4-yl)acetamide (Enantiomer)
207. N-(4-(3-Fluoro-phenyl)-1-{2-[2-(thiophene-3-carbonyl)-1,2,3,4-tetrahydro-isoquinolin-1-yl]-ethyl}-piperidin-4-yl)acetamide (Enantiomer)
208. N-(4-(3-Fluoro-phenyl)-1-{2-[2-(4-pyrazol-1-yl-benzoyl)-1,2,3,4-tetrahydro-isoquinolin-1-yl]-ethyl}-piperidin-4-yl)acetamide (Enantiomer)
209. N-(1-{2-[2-(Naphthalene-1-carbonyl)-1,2,3,4-tetrahydro-isoquinolin-1-yl]-ethyl}-4-phenyl-piperidin-4-yl)acetamide (Enantiomer)

TABLE 1

Measured molecular mass (M + H+), measured HPLC-retention time (RT, min) and UV- and ELSD-purities (%) and synthesis method.

| compound | M + H+ | RT min. | UV-purity (%) | ELSD-purity (%) | Synthesis method |
|---|---|---|---|---|---|
| 1 | 500.3 | 2.34 | 84.41 | 100 | B |
| 2 | 474.4 | 2.38 | 83.5 | 100 | B |
| 3 | 496.3 | 2.45 | 75.89 | 100 | B |
| 4 | 481.9 | 2.29 | 83.81 | 100 | B |
| 5 | 500.2 | 2.29 | 83.54 | 100 | B |
| 6 | 510 | 2.46 | 84.14 | 100 | B |
| 7 | 497.4 | 2.29 | 100 | 100 | B |
| 8 | 525.4 | 2.40 | 89.67 | 100 | B |
| 9 | 478.2 | 2.20 | 75.37 | 99.26 | A |
| 10 | 497.1 | 2.36 | 75.37 | 99.26 | B |
| 12 | 463 | 2.31 | 100 | 100 | B |
| 13 | 598.1 | 2.45 | 93.85 | 100 | B |
| 14 | 467 | 2.43 | 73.81 | 96.61 | B |
| 15 | 471.2 | 2.21 | 93.09 | 100 | B |
| 16 | 485 | 2.34 | 86.3 | 100 | B |
| 17 | 501.2 | 2.27 | 94.08 | 100 | B |
| 18 | 491.1 | 2.54 | 100 | 100 | B |
| 19 | 488.9 | 2.22 | 84.77 | 100 | B |
| 20 | 504.9 | 2.27 | 77.86 | 100 | B |
| 21 | 489.2 | 2.25 | 80.99 | 100 | B |
| 22 | 505.1 | 2.39 | 85.64 | 100 | B |
| 23 | 514.2 | 2.42 | 79.04 | 100 | B |
| 24 | 501.3 | 2.25 | 83.93 | 99.53 | B |

TABLE 1-continued

Measured molecular mass (M + H$^+$), measured HPLC-retention time (RT, min) and UV- and ELSD-purities (%) and synthesis method.

| compound | M + H$^+$ | RT min. | UV-purity (%) | ELSD-purity (%) | Synthesis method |
|---|---|---|---|---|---|
| 25 | 499.1 | 2.42 | 91.88 | 100 | B |
| 26 | 465.1 | 2.34 | 97.12 | 100 | B |
| 27 | 501.1 | 2.25 | 82.81 | 100 | B |
| 28 | 485.2 | 2.27 | 72.97 | 100 | B |
| 29 | 505.2 | 2.73 | 71.89 | 100 | B |
| 30 | 502.8 | 2.31 | 74.17 | 100 | B |
| 31 | 554.2 | 2.60 | 95.47 | 100 | B |
| 32 | 435.2 | 2.06 | 86.69 | 100 | B |
| 33 | 472 | 1.80 | 95.32 | 100 | B |
| 34 | 585 | 2.81 | 96.53 | 100 | B |
| 35 | 519 | 2.44 | 89.59 | 100 | B |
| 36 | 437.3 | 2.13 | 91.14 | 100 | B |
| 37 | 514.2 | 2.40 | 85.04 | 100 | B |
| 38 | 520.3 | 2.29 | 71.77 | 76.11 | B |
| 39 | 477.4 | 2.43 | 91.78 | 100 | B |
| 40 | 514.3 | 2.33 | 91.25 | 99.32 | B |
| 41 | 502.3 | 2.35 | 70.93 | 83.59 | B |
| 42 | 551.3 | 2.44 | 90.64 | 100 | B |
| 43 | 503.1 | 2.37 | 74.38 | 100 | B |
| 44 | 550.1 | 2.50 | 73.67 | 95.11 | B |
| 45 | 528.3 | 2.44 | 93.37 | 79.93 | B |
| 46 | 548.2 | 2.22 | 94.88 | 100 | B |
| 47 | 498.3 | 2.66 | 74.25 | 96.35 | B |
| 48 | 513.3 | 2.77 | 100 | 97.34 | B |
| 49 | 537.1 | 2.33 | 89.23 | 100 | B |
| 50 | 486.4 | 2.12 | 99.47 | 100 | B |
| 51 | 522.3 | 2.29 | 100 | 100 | B |
| 52 | 563.1 | 2.27 | 72.61 | 100 | B |
| 53 | 489.2 | 2.23 | 76.61 | 100 | B |
| 54 | 473.6 | 2.51 | 70.49 | 82.63 | B |
| 55 | 565.3 | 2.55 | 72.19 | 100 | B |
| 56 | 479.2 | 2.74 | 74.67 | 83.39 | B |
| 57 | 487.3 | 2.66 | 82.69 | 99.27 | B |
| 58 | 492.2 | 2.08 | 85.05 | 100 | B |
| 59 | 445.5 | 2.58 | 70.23 | 73.14 | B |
| 60 | 505.2 | 2.65 | 71.04 | 76.63 | B |
| 61 | 485.1 | 2.57 | 88.72 | 100 | B |
| 62 | 523.4 | 2.23 | 100 | 100 | B |
| 63 | 549.3 | 2.19 | 93.44 | 100 | B |
| 64 | 502.4 | 2.29 | 91.44 | 100 | B |
| 65 | 554.3 | 2.38 | 93.61 | 100 | B |
| 66 | 435.2 | 2.38 | 72.75 | 93.86 | B |
| 67 | 515.3 | 2.51 | 77.67 | 78.14 | B |
| 68 | 601.3 | 2.63 | 81.38 | 97.64 | B |
| 69 | 569.3 | 1.65 | 76.77 | 88.30 | B |
| 70 | 517.3 | 2.67 | 79.03 | 86.76 | B |
| 71 | 487.4 | 2.50 | 72.35 | 95.17 | B |
| 72 | 573.5 | 2.42 | 90.45 | 100 | B |
| 73 | 470.4 | 2.45 | 83.20 | 100 | B |
| 74 | 459.4 | 2.27 | 92.31 | 100 | B |
| 75 | 599.3 | 2.36 | 96.26 | 98.55 | B |
| 76 | 477.2 | 2.40 | 100 | 93.03 | B |
| 77 | 491.3 | 2.51 | 86.66 | 73.72 | B |
| 78 | 631.5 | 1.84 | 75.78 | 100 | B |
| 79 | 451.1 | 2.50 | 86.14 | 100 | B |
| 80 | 511.1 | 2.48 | 100 | 100 | B |
| 81 | 471.3 | 2.23 | 92.66 | 100 | B |
| 82 | 463.3 | 2.36 | 100 | 100 | B |
| 83 | 563.1 | 2.24 | 90.29 | 100 | B |
| 84 | 518.2 | 2.03 | 95.48 | 100 | B |
| 85 | 512.2 | 2.02 | 94.94 | 88.11 | B |
| 86 | 610.5 | 2.41 | 94.60 | 98.31 | B |
| 87 | 616.2 | 2.56 | 89.81 | 100 | B |
| 88 | 459.3 | 2.69 | 71.44 | 73.94 | B |
| 89 | 599.2 | 2.33 | 91.53 | 100 | B |
| 90 | 623.4 | 2.65 | 87.37 | 98.35 | B |
| 91 | 555.3 | 2.44 | 89.31 | 100 | B |
| 92 | 503.2 | 2.90 | 71.70 | 70.84 | B |
| 93 | 490.2 | 2.48 | 100 | 100 | B |
| 94 | 459.2 | 2.42 | 83.29 | 100 | B |
| 95 | 485.3 | 2.33 | 94.29 | 100 | B |
| 96 | 580.5 | 2.22 | 96.44 | 100 | B |
| 97 | 443.2 | 2.25 | 98.80 | 100 | B |
| 98 | 516 | 2.42 | 90.05 | 100 | B |
| 99 | 461.2 | 2.29 | 100 | 100 | B |
| 100 | 574.4 | 2.26 | 99.42 | 100 | B |
| 101 | 474.4 | 2.02 | 100 | 100 | B |
| 102 | 502.3 | 2.23 | 94.60 | 100 | B |
| 103 | 533.1 | 2.41 | 87.36 | 97.35 | B |
| 104 | 489.4 | 2.46 | 79.39 | 100 | B |
| 105 | 486.4 | 1.65 | 88.94 | 100 | B |
| 106 | 459.5 | 2.74 | 81.14 | 100 | B |
| 107 | 485.4 | 2.21 | 94.86 | 100 | B |
| 108 | 485 | 2.16 | 70.08 | 70.13 | B |
| 109 | 554.4 | 2.34 | 70.00 | 74.91 | B |
| 110 | 417.2 | 2.35 | 92.41 | 100 | B |
| 111 | 549.4 | 2.14 | 95.35 | 100 | B |
| 112 | 507.5 | 2.45 | 88.27 | 98.43 | B |
| 113 | 489.6 | 2.33 | 89.20 | 97.90 | B |
| 114 | 464.6 | 2.39 | 97.56 | 100 | B |
| 115 | 476.6 | 2.44 | 97.18 | 100 | B |
| 116 | 472.7 | 2.53 | 98.22 | 100 | B |
| 117 | 458.6 | 2.40 | 86.63 | 100 | B |
| 118 | 483.7 | 2.53 | 99.38 | 100 | B |
| 119 | 487.7 | 2.13 | 95.52 | 100 | B |
| 120 | 486.6 | 2.62 | 94.23 | 100 | B |
| 121 | 498.6 | 2.66 | 98.51 | 100 | B |
| 122 | 473.7 | 1.75 | 94.26 | 100 | B |
| 123 | 498.6 | 2.44 | 97.66 | 100 | A |
| 124 | 609.1 | 2.54 | 97.77 | 100 | B |
| 125 | 500.6 | 2.32 | 93.9 | 98.82 | B |
| 126 | 508.6 | 2.37 | 98.82 | 100 | B |
| 127 | 472.7 | 2.83 | 95.08 | 100 | B |
| 128 | 492.7 | 2.63 | 97.33 | 100 | B |
| 129 | 485 | 2.29 | 94.23 | 99.4 | B |
| 130 | 472.7 | 2.52 | 95.96 | 100 | B |
| 131 | 460.7 | 2.49 | 96.36 | 100 | B |
| 132 | 534.6 | 2.48 | 94.21 | 99.15 | B |
| 133 | 486.6 | 2.58 | 86.65 | 100 | B |
| 134 | 510.7 | 2.41 | 75.55 | 96.08 | B |
| 135 | 512.6 | 2.29 | 98.04 | 100 | B |
| 136 | 465.1 | 2.58 | 96.36 | 100 | B |
| 137 | 453.1 | 2.54 | 97.52 | 100 | B |
| 138 | 506.7 | 2.78 | 98.11 | 100 | B |
| 139 | 502.7 | 2.88 | 77.28 | 94.4 | B |
| 140 | 496.6 | 2.39 | 97.44 | 100 | B |
| 141 | 491.9 | 2.44 | 99.44 | 99.2 | B |
| 142 | 514.6 | 2.34 | 91.48 | 98.85 | B |
| 143 | 597.1 | 2.49 | 97.94 | 100 | B |
| 144 | 460.7 | 2.49 | 95.22 | 100 | B |
| 145 | 528.7 | 2.98 | 98.91 | 100 | B |
| 146 | 450.6 | 2.28 | 100 | 100 | B |
| 147 | 526.7 | 2.92 | 96.57 | 99.25 | B |
| 148 | 460.5 | 2.10 | 96.13 | 99.34 | B |
| 149 | 517.8 | 2.50 | 99.13 | 100 | B |
| 150 | 522.6 | 2.26 | 92.92 | 99.26 | B |
| 151 | 504.7 | 2.73 | 97.79 | 100 | B |
| 152 | 508.6 | 2.33 | 99.37 | 100 | B |
| 153 | 519.6 | 2.33 | 99.06 | 100 | B |
| 154 | 500.6 | 2.19 | 96 | 99.4 | B |
| 155 | 514.7 | 2.85 | 93.87 | 100 | B |
| 156 | 464.6 | 2.36 | 91.14 | 100 | B |
| 157 | 520.6 | 2.64 | 94.34 | 99.05 | B |
| 158 | 471.7 | 2.51 | 97.9 | 100 | B |
| 159 | 635.9 | 2.39 | 96.68 | 98.58 | B |
| 160 | 520.7 | 2.69 | 92.98 | 99.42 | B |
| 161 | 538.7 | 2.62 | 97.24 | 98.81 | B |
| 162 | 513.8 | 2.88 | 95.64 | 100 | B |
| 163 | 494.7 | 2.52 | 98.25 | 100 | B |
| 164 | 482.5 | 2.32 | 91.14 | 100 | B |
| 165 | 521.7 | 2.41 | 93.78 | 100 | B |
| 166 | 489.1 | 2.45 | 97.97 | 100 | B |
| 167 | 518.7 | 2.34 | 87.58 | 97.31 | B |
| 168 | 472.6 | 2.50 | 94.41 | 99.01 | B |

TABLE 1-continued

Measured molecular mass (M + H⁺),
measured HPLC-retention time (RT, min) and
UV- and ELSD-purities (%) and synthesis method.

| compound | M + H⁺ | RT min. | UV-purity (%) | ELSD-purity (%) | Synthesis method |
|---|---|---|---|---|---|
| 169 | 525.4 | 2.52 | 98.4 | 98.78 | B |
| 170 | 512.7 | 2.50 | 98.1 | 99.2 | B |
| 171 | 499.5 | 2.37 | 98.66 | 99.01 | B |
| 172 | 502.8 | 3.15 | 96.92 | 100 | B |
| 173 | 485.5 | 2.28 | 86.08 | 99.43 | B |
| 174 | 535.7 | 2.32 | 89.96 | 99.01 | B |
| 175 | 501 | 2.42 | 98.67 | 100 | B |
| 176 | 475.7 | 2.09 | 97.47 | 100 | B |
| 177 | 507 | 2.52 | 90.73 | 100 | B |
| 178 | 478.6 | 1.94 | 91.92 | 100 | B |
| 179 | 530.3 | 2.01 | 89.59 | 99.31 | B |
| 180 | 550.2 | 2.32 | 96.42 | 98.14 | B |
| 181 | 534.2 | 2.15 | 99.1 | 100 | B |
| 182 | 578.2 | 2.18 | 99.05 | 100 | B |
| 183 | 518.2 | 2.00 | 98.42 | 99.38 | B |
| 184 | 542.4 | 2.34 | 93.23 | 99.9 | B |
| 185 | 514.4 | 2.09 | 99.41 | 100 | B |
| 186 | 534.2 | 2.11 | 98.69 | 100 | B |
| 187 | 578.3 | 2.04 | 71.31 | 100 | B |
| 188 | 562.2 | 2.13 | 95.59 | 100 | A |
| 189 | 550.2 | 2.22 | 88.21 | 95.21 | B |
| 190 | 568.4 | 2.22 | 86.21 | 98.71 | B |
| 191 | 542.4 | 2.03 | 99.09 | 100 | B |
| 192 | 550.2 | 2.17 | 97.37 | 100 | B |
| 193 | 492.3 | 2.07 | 81.75 | 100 | B |
| 194 | 516.3 | 2.09 | 96.4 | 100 | B |
| 195 | 556.3 | 2.15 | 99.36 | 99.89 | B |
| 196 | 576.3 | 2.03 | 96.774 | 100 | B |
| 197 | 580.4 | 2.14 | 98.59 | 100 | B |
| 198 | 518.2 | 1.95 | 82.81 | 99.74 | B |
| 199 | 496.2 | 2.15 | 91.36 | 99.03 | B |
| 200 | 534.2 | 2.01 | 79.14 | 99.08 | B |
| 201 | 530.3 | 2.01 | 99.08 | 100 | B |
| 202 | 516.3 | 2.16 | 94.57 | 98.33 | B |
| 203 | 500.5 | 1.97 | 96.4 | 100 | B |
| 204 | 502.4 | 2.25 | 88.94 | 100 | B |
| 205 | 562.1 | 2.20 | 93.75 | 96.46 | B |
| 206 | 530.3 | 2.00 | 98.7 | 100 | B |
| 207 | 506.2 | 1.92 | 98.2 | 100 | B |
| 208 | 566.4 | 1.99 | 98.45 | 100 | B |
| 209 | 532.2 | 2.21 | 93.74 | 98.44 | B |

Pharmacological Testing

The compounds of the invention were tested in a well-recognised and reliable test. The test was as follows:

Inhibition of Binding of $^{125}$I-NKA to Human NK2 Receptors

The compounds of the invention have been found to potently inhibit the binding of $^{125}$I-NKA to the human NK2 receptor.

By this method, the inhibition by drugs of the binding of $^{125}$I-NKA to membranes of human cloned NK2 receptors expressed in CHO-cells is determined in vitro.

Briefly, the affinity of the compounds was measured by their ability to displace $^{125}$I-NKA, by incubating hNK2 expressing CHO membranes with compound and radioligand at room temperature for 60 minutes. Incubation was terminated by rapid filtration through GF/C filters, and filters were counted in a Wallac Trilux Scintillation Counter. The IC50 values for the compounds No. 1-209, exemplified above, was determined to be 200 nM or less. For the majority of the compounds the IC50 values were 50 nM or less, and for a large group of the compounds the IC50 values were 10 nM or less.

FORMULATION EXAMPLES

The pharmaceutical formulations of the invention may be prepared by conventional methods in the art.

For example: Tablets may be prepared by mixing the active ingredient with ordinary adjuvants and/or diluents and subsequently compressing the mixture in a conventional tabletting machine. Examples of adjuvants or diluents comprise: Corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

Solutions for injections may be prepared by dissolving the active ingredient and possible additives in a part of the solvent for injection, preferably sterile water, adjusting the solution to the desired volume, sterilising the solution and filling it in suitable ampoules or vials. Any suitable additive conventionally used in the art may be added, such as tonicity agents, preservatives, antioxidants, etc.

Typical examples of recipes for the formulation of the invention are as follows:

1) Tablets containing 5.0 mg of a compound of the invention calculated as the free base:

| | |
|---|---|
| Compound 1a or 1b | 5.0 mg |
| Lactose | 60 mg |
| Maize starch | 30 mg |
| Hydroxypropylcellulose | 2.4 mg |
| Microcrystalline cellulose | 19.2 mg |
| Croscarmellose Sodium Type A | 2.4 mg |
| Magnesium stearate | 0.84 mg |

2) Tablets containing 0.5 mg of a compound of the invention calculated as the free base:

| | |
|---|---|
| Compound 1a or 1b | 0.5 mg |
| Lactose | 46.9 mg |
| Maize starch | 23.5 mg |
| Povidone | 1.8 mg |
| Microcrystalline cellulose | 14.4 mg |
| Croscarmellose Sodium Type A | 1.8 mg |
| Magnesium stearate | 0.63 mg |

3) Syrup containing per millilitre:

| | |
|---|---|
| Compound 1a or 1b | 25 mg |
| Sorbitol | 500 mg |
| Hydroxypropylcellulose | 15 mg |
| Glycerol | 50 mg |
| Methyl-paraben | 1 mg |
| Propyl-paraben | 0.1 mg |
| Ethanol | 0.005 mL |
| Flavour | 0.05 mg |
| Saccharin sodium | 0.5 mg |
| Water | ad 1 mL |

4) Solution for injection containing per millilitre:

| | |
|---|---|
| Compound 1a or 1b | 0.5 mg |
| Sorbitol | 5.1 mg |
| Acetic Acid | 0.05 mg |

| | |
|---|---|
| Saccharin sodium | 0.5 mg |
| Water | ad 1 mL |

The invention claimed is:

1. A compound of formula I

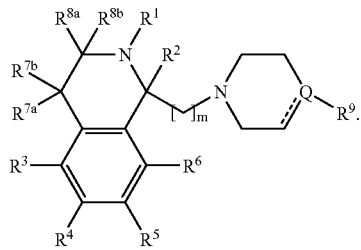

wherein $R^1$ is $R^{11}CO-$, $R^{11}CS-$, $R^{11}SO_2-$, $R^{11}OCO-$, $R^{11}SCO-$ or $R^{11}CO-CR^{12}R^{13}-$ wherein $R^{11}$ is $C_{1-12}$-alkyl, $C_{2-6}$-alkenyl, $C_{2-6}$-alkynyl, $C_{3-8}$-cycloalkyl, $C_{3-8}$-cycloalkyl-$C_{1-6}$alkyl, aryl, aryl-$C_{1-6}$-alkyl, heteroaryl, heteroaryl-$C_{1-6}$-alkyl, tetrahydropyranyl, 1,2,3,4-tetrahydronaphtalenyl, or 4H-benzo[1,3]dioxinyl optionally substituted with halogen, wherein each of said $C_{1-6}$-alkyl, aryl, heteroaryl and $C_{3-8}$-cycloalkyl groups independently are unsubstituted or substituted with one or more substituents selected from the group consisting of halogen, $C_{1-6}$-alkyl, $C_{1-6}$-alkoxy, aryl-$C_{1-6}$-alkoxy, $C_{1-6}$-alkylsulfanyl, aryl and aryloxy, wherein said aryl and aryloxy independently are unsubstituted or substituted with one or more halogen; and $R^{12}$ and $R^{13}$ independently are hydrogen or $C_{1-6}$-alkyl; or $R^1$ is $R^{14}R^{15}NCO-$ or $R^{14}R^{15}NCS-$, wherein $R^{14}$ and $R^{15}$ each are independently hydrogen, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, aryl or aryl-$C_{1-6}$-alkyl, wherein each of said $C_{1-6}$-alkyl, aryl and $C_{3-8}$-cycloalkyl groups independently are unsubstituted or substituted with one or more substituents selected from the group consisting of halogen, $C_{1-6}$-alkyl and $C_{1-6}$-alkoxy; or $R^{14}$ and $R^{15}$, taken together with the N-atom to which they are linked, form a pyrrolidinyl, piperidinyl or perhydroazepinyl group;

$R^2$ is hydrogen, trifluoromethyl or $C_{1-6}$-alkyl;

$R^3$-$R^6$, $R^{7a}$, $R^{7b}$, $R^{8a}$ and $R^{8b}$ each are independently hydrogen, halogen, cyano, nitro, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, amino, $C_{1-6}$-alkylamino, di-($C_{1-6}$-alkyl)amino, $C_{1-6}$-alkylcarbonyl, aminocarbonyl, $C_{1-6}$-alkylaminocarbonyl, di-($C_{1-6}$-alkyl)aminocarbonyl, $C_{1-6}$-alkoxy, $C_{1-6}$-alkylthio, hydroxy, trifluoromethyl, trifluoromethylsulfonyl or $C_{1-6}$-alkylsulfonyl;

m is 2-6;

$R^9$ is benzyl, benzoyl, 2,3-dihydrobenzofuranyl, mono- or bicyclic aryl, or heteroaryl wherein each benzyl, benzoyl, aryl or heteroaryl optionally is substituted with one or more substituents selected from halogen, cyano, nitro, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, amino, $C_{1-6}$-alkylamino, di-($C_{1-6}$-alkyl)amino, $C_{1-6}$-alkylcarbonyl, aminocarbonyl, $C_{1-6}$-alkylaminocarbonyl, di-($C_{1-6}$-alkyl) aminocarbonyl, $C_{1-6}$-alkoxy, $C_{1-6}$-alkylthio, hydroxy, trifluoromethyl, difluoromethyl, fluoromethyl and trifluoromethylsulfonyl;

Q is C, N or $CR^{10}$;

wherein $R^{10}$ is hydrogen, halogen, cyano, nitro, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, amino, $C_{1-6}$-alkylamino, di-($C_{1-6}$-alkyl)amino, $C_{1-6}$-alkylcarbonyl, aminocarbonyl, $C_{1-6}$-alkylaminocarbonyl, di-($C_{1-6}$-alkyl)aminocarbonyl, $C_{1-6}$-alkoxy, $C_{1-6}$-alkylthio, hydroxy, trifluoromethyl, difluoromethyl, fluoromethyl, trifluoromethylsulfonyl, $-NR^{30}COR^{31}$ wherein $R^{30}$ is hydrogen or $C_{1-6}$-alkyl and $R^{31}$ is $C_{1-6}$-alkyl, $-COOR^{16}$ wherein $R^{16}$ is hydrogen or $C_{1-6}$-alkyl, or $-CONR^{17}R^{18}$, wherein $R^{17}$ and $R^{18}$ each are independently hydrogen or $C_{1-6}$-alkyl; or $R^{17}$ and $R^{18}$, taken together with the nitrogen to which they are attached, form a piperidinyl, piperazinyl or morpholinyl group, wherein said piperidinyl, piperazinyl and morpholinyl group is unsubstituted or substituted with a $C_{1-6}$-alkyl;

or when Q is $CR^{10}$, $R^9$ and $R^{10}$, taken together with a carbon to which they are attached, form a cyclic structure selected from the group consisting of:

1)

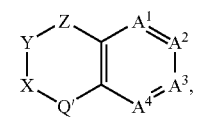

2)

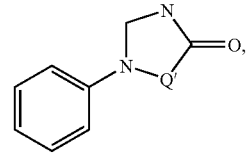

3)

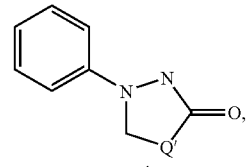

and

4)

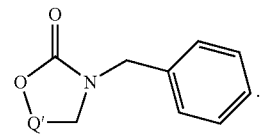

wherein Q' is a carbon shared with a piperidine ring whereby said cyclic structure together with said piperidine ring forms a spiro structure; and X, Y, and Z each are independently O, $NR^{19}$, $CR^{23}R^{24}$, $S(O)_n$ or a bond, wherein: $R^{19}$ is hydrogen, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, trifluoromethyl, acyl, thioacyl or trifluoromethylsulfonyl; $R^{19}$ is $R^{20}SO_2-$, $R^{20}OCO-$ or $R^{20}SCO-$, wherein $R^{20}$ is $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl or aryl; or $R^{19}$ is $R^{21}R^{22}NCO-$ or $R^{21}R^{22}NCS-$, wherein $R^{21}$ and $R^{22}$ each are independently hydrogen, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, or aryl, wherein said aryl is unsubstituted or substituted with one or more substituents selected from $C_{1-6}$-alkyl or halogen; or $R^{21}$ and $R^{22}$, taken together with the N-atom to which they are linked, form a pyrrolidinyl, piperidinyl or perhydroazepinyl group; and $R^{23}$ and $R^{24}$ each are independently hydrogen, halogen, cyano, nitro, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, aryl or heteroaryl, wherein said aryl is unsubstituted or substituted with one or more substituents selected from $C_{1-6}$-alkyl, halogen, amino, $C_{1-6}$-alkylamino, or $NR^{25}R^{26}$, wherein $R^{25}$ and $R^{26}$ each are independently $C_{1-6}$-alkyl, $C_{1-6}$-alkylcarbonyl, aminocarbonyl, $C_{1-6}$-alkylaminocarbonyl, di-($C_{1-6}$-alkyl)aminocarbonyl, $C_{1-6}$-alkoxy, $C_{1-6}$-alkylthio, hydroxy, trifluoromethyl, trifluoromethylsulfonyl or $C_{1-6}$-alkylsulfonyl; or $R^{25}$ and $R^{26}$, taken together with the N-atom to which they are linked, form a pyrrolidinyl, piperidinyl, perhydroazepinyl or morpholinyl group; or $R^{23}$ and $R^{24}$, taken together, form an oxo group; and n is 0, 1 or 2; provided that no more than one of X, Y and Z may be a bond, and provided that two adjacent X, Y or Z groups may not at the same time be O and S; and $A^1$, $A^2$, $A^3$ and $A^4$ each are independently N or $CR^{27}$, wherein $R^{27}$ is hydrogen, halogen, cyano, nitro, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, $C_{1-6}$-alkylcarbonyl, aminocarbonyl, $C_{1-6}$-alkylaminocarbonyl, di-($C_{1-6}$-alkyl)aminocarbonyl, $C_{1-6}$-alkoxy, $C_{1-6}$-alkylthio, hydroxy, trifluoromethyl, difluoromethyl, fluoromethyl, trifluoromethylsulfonyl, $C_{1-6}$-alkylsulfonyl, amino, or $NR^{28}R^{29}$, wherein $R^{28}$ and $R^{29}$ each are independently hydrogen or $C_{1-6}$-alkyl; or $R^{28}$ and $R^{29}$, taken together with the N-atom to which they are linked, form a pyrrolidinyl, piperidinyl, perhydroazepinyl or morpholinyl group; provided that only one of $A^1$, $A^2$, $A^3$ and $A^4$ may be N; and provided that a dotted line emanating from Q is a bond when Q is C, and no bond when Q is $CR^{10}$ or N;

or a pharmaceutically acceptable acid addition salt thereof.

2. A compound according to claim 1, wherein Q is $CR^{10}$, and $R^9$ and $R^{10}$, taken together with the carbon to which they are attached, form a bicyclic structure as shown in formula 1):

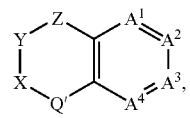

wherein Q' is a carbon shared with a piperidine ring whereby said bicyclic structure together with said piperidine ring form a spiro structure; and X, Y and Z each are independently O, $NR^{19}$, $CR^{23}R^{24}$, $S(O)_n$ or a bond, wherein $R^{19}$ is hydrogen, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, trifluoromethyl, acyl, thioacyl or trifluoromethylsulfonyl; $R^{19}$ is $R^{20}SO_2$—, $R^{20}OCO$— or $R^{20}SCO$—, wherein $R^{20}$ is $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, or aryl; or $R^{19}$ is $R^{21}R^{22}NCO$— or $R^{21}R^{22}NCS$—, wherein $R^{21}$ and $R^{22}$ each are independently hydrogen, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, or aryl, wherein said aryl is unsubstituted or substituted with one or more substituents selected from $C_{1-6}$-alkyl or halogen; or $R^{21}$ and $R^{22}$, taken together with the N-atom to which they are linked, form a pyrrolidinyl, piperidinyl, or perhydroazepinyl group; and $R^{23}$ and $R^{24}$ each are independently hydrogen, halogen, cyano, nitro, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, aryl, or heteroaryl, wherein said aryl is unsubstituted or substituted with one or more substituents selected from $C_{1-6}$-alkyl, halogen, amino, $C_{1-6}$-alkylamino, or $NR^{25}R^{26}$, wherein $R^{25}$ and $R^{26}$ each are independently $C_{1-6}$-alkyl, $C_{1-6}$-alkylcarbonyl, aminocarbonyl, $C_{1-6}$-alkylaminocarbonyl, di-($C_{1-6}$-alkyl)aminocarbonyl, $C_{1-6}$-alkoxy, $C_{1-6}$-alkylthio, hydroxy, trifluoromethyl, trifluoromethylsulfonyl or $C_{1-6}$-alkylsulfonyl; or $R^{25}$ and $R^{26}$, taken together with the N-atom to which they are linked, form a pyrrolidinyl, piperidinyl, perhydroazepinyl, or morpholinyl group; or $R^{23}$ and $R^{24}$, taken together form an oxo group; and n is 0, 1 or 2; provided that no more than one of X, Y and Z may be a bond, and provided that two adjacent X, Y or Z groups may not at the same time be O and S; and $A^1$, $A^2$, $A^3$ and $A^4$ each are independently N $CR^{27}$, wherein $R^{27}$ is hydrogen, halogen, cyano, nitro, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, $C_{1-6}$-alkylcarbonyl, aminocarbonyl, $C_{1-6}$-alkylaminocarbonyl, di- ($C_{1-6}$-alkyl)aminocarbonyl, $C_{1-6}$-alkoxy, $C_{1-6}$-alkythio, hydroxy, trifluoromethyl, difluoromethyl, fluoromethyl, trifluoromethylsulfonyl, $C_{1-6}$-alkylsulfonyl, amino, or $NR^{28}R^{29}$, wherein $^{28}$ and $R^{29}$ each are independently hydrogen or $C_{1-6}$-alkyl; or $R^{28}$ and $R^{29}$, taken together with the N-atom to which they are linked, form a pyrrolidinyl, piperidinyl, perhydroazepinyl or morpholinyl group provided that only one of $A^1$, $A^2$, $A^3$ and $A^4$ may be N.

3. A compound according to claim 2, wherein X, Y and Z are one of the following combinations: X is oxygen, Y is a bond and Z is $CR^{23}R^{24}$; X is $CR^{23}R^{24}$, Y is a bond and Z is oxygen; X is $NR^{19}$, Y is a bond and Z is $CR^{23}R^{24}$; X is $CR^{23}R^{24}$, Y is a bond and Z is $NR^{19}$; X is CO, Y is a bond and Z is $NR^{19}$; X is $SO_2$, Y is a bond and Z is $NR^{19}$; X is SO, Y is a bond and Z is $NR^{19}$; X is $CR^{23}R^{24}$, Y is a bond and Z is S; X is $CR^{23}R^{24}$, Y is a bond and Z is SO; or X is $CR^{23}R^{24}$, Y is a bond and Z is $SO_2$, wherein $R^{19}$ is hydrogen, acetyl or methylsulfonyl; and $R^{23}$ and $R^{24}$ each are independently hydrogen, methyl, isobutyl, cyclohexyl or 4-fluorophenyl.

4. A compound according to claim 2, wherein X, Y, and Z, taken together form a group selected from: —O—$CR^{23}R^{24}$—, —$CR^{23}R^{24}$—O—, —$NR^{19}$—$CR^{23}R^{24}$—, —$CR^{23}R^{24}$—$NR^{19}$—, —CO—$NR^{19}$—, —$SO_2$—$NR^{19}$—, —SO—$NR^{19}$—, —$CR^{23}R^{24}$—S—, —$CR^{23}R^{24}$—SO—, and —$CR^{23}R^{24}$—$SO_2$—, wherein $R^{19}$ is hydrogen, acetyl or methylsulfonyl; and $R^{23}$ and $R^{24}$ each are independently hydrogen, methyl, isobutyl, cyclohexyl or 4-fluorophenyl.

5. A compound according to claim 2 wherein $A^3$ is N or $CR^{27}$, wherein $R^{27}$ is halogen, cyano, nitro, $C_{1-6}$-alkylcarbonyl, aminocarbonyl, $C_{1-6}$-alkylaminocarbonyl, di-($C_{1-6}$-alkyl)aminocarbonyl, $C_{1-6}$-alkoxy, hydroxy, trifluoromethyl, difluoromethyl, fluoromethyl, trifluoromethylsulfonyl, $C_{1-6}$-alkylsulfonyl, or $NR^{28}R^{29}$, wherein $R^{28}$ and $R^{29}$ each are independently hydrogen or $C_{1-6}$-alkyl; or $R^{28}$ and $R^{29}$, taken together with the N-atom to which they are linked, form a pyrrolidinyl, piperidinyl, perhydroazepinyl or morpholinyl group.

6. A compound according to claim 2, wherein $A^1$, $A^2$, $A^3$ and $A^4$ are each independently $CR^{27}$, wherein $R^{27}$ is hydrogen, halogen, cyano, nitro, $C_{1-6}$-alkyl, $C_{2-6}$-alkenyl, $C_{2-6}$-alkynyl, $C_{3-8}$-cycloalkyl, $C_{3-8}$-cycloalky-$C_{1-6}$-alkyl, $C_{1-6}$-alkylthio, amino, $C_{1-6}$-alkylcarbonyl, aminocarbonyl, $C_6$-alkylaminocarbonyl, di-($C_{1-6}$-alkyl)aminocarbonyl, $C_{1-6}$-alkoxy, $C_{1-6}$-alkylthio, hydroxy, trifluoromethyl, difluoromethyl, fluoromethyl, trifluoromethylsulfonyl, $C_{1-6}$-alkylsulfonyl, amino, or $NR^{28}R^{29}$, wherein $R^{28}$ and $R^{29}$ each are independently hydrogen or $C_{1-6}$-alkyl; or $R^{28}$ and $R^{29}$, taken together with the N-atom to which they are linked, form a pvrrolidinyl, piperidinyl, perhydroazepinyl or morpholinyl group; provided that only one of $A^1$, $A^2$, $A^3$ and $A^4$ may be N.

7. A compound according to claim 2, wherein said bicyclic structure is selected from the group consisting of:

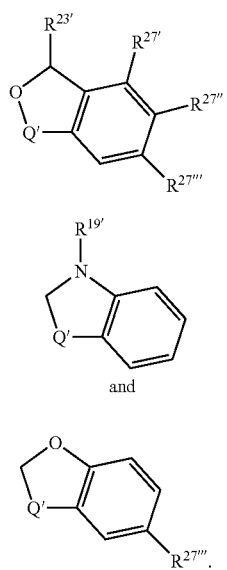

wherein $R^{19'}$ is acetyl or methylsulfonyl; $R^{23'}$ is hydrogen or methyl; $R^{27'}$ is hydrogen or fluoro; $R^{27''}$ is hydrogen, fluoro, methyl or isopropyl; and $R^{27'''}$ is hydrogen, fluoro or trifluoromethyl.

8. A compound according to claim 1 wherein $R^9$ and $R^{10}$, taken together with a carbon to which they are attached, form a cyclic structure selected from the group consisting of:

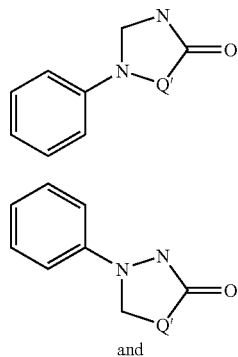

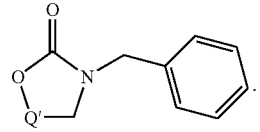

wherein Q' is a carbon shared with a piperidine ring whereby said cyclic structure together with said piperidine ring form a spiro structure.

9. A compound according to claim 1, wherein $R^9$ is benzyl, benzoyl, 2,3-dihydrobenzofuran-7-yl, mono- or bicyclic aryl, or heteroaryl, wherein each benzyl, benzoyl, aryl or heteroaryl optionally is substituted with one or more substituents selected from halogen, cyano, nitro, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, amino, $C_{1-6}$-alkylamino, di-($C_{1-6}$-alkyl)amino, $C_{1-6}$-alkylcarbonyl, aminocarbonyl, $C_{1-6}$-alkylaminocarbonyl, di-($C_{1-6}$-alkyl)aminocarbonyl, $C_{1-6}$-alkoxy, $C_{1-6}$-alkylthio, hydroxy, trifluoromethyl, difluoromethyl, fluoromethyl and trifluoromethylsulfonyl.

10. A compound according to claim 9, wherein $R^9$ is 2,3-dihydrobenzofuran-7-yl, benzyl or benzoyl, wherein said benzyl or benzoyl is unsubstituted or substituted with one or more halogens; or $R^9$ is mono- or bicyclic aryl or heteroaryl selected from the group consisting of phenyl, indolyl, pyridyl, thiophenyl and benzisoxazolyl, wherein each aryl or heteroaryl optionally is substituted with one or more substituents selected from halogen, cyano, nitro, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, amino, C p6-alkylamino, di-($C_{1-6}$-alkyl)amino, $C_{1-6}$-alkylcarbonyl, aminocarbonyl, $C_{1-6}$-alkylaminocarbonyl, di-($C_{1-6}$-alkyl)aminocarbonyl, $C_{1-6}$-alkoxy, $C_{1-6}$-alkylthio, hydroxy, trifluoromethyl, difluoromethyl, fluoromethyl and trifluoromethylsulfonyl.

11. A compound according to claim 10, wherein said mono- or bicyclic aryl or heteroaryl is selected from the group consisting of phenyl, indol-3-yl and benzisoxazol-3-yl, wherein said phenyl, indol-3-yl or benzisoxazol-3-yl optionally is substituted with one or more substituent selected from halogen, cyano, nitro, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, amino, $C_{1-6}$-alkylamino, di-($C_{1-6}$-alkyl)amino, $C_{1-6}$-alkylcarbonyl, aminocarbonyl, $C_{1-6}$-alkylaminocarbonyl, di-($C_{1-6}$-alkyl)aminocarbonyl, $C_{1-6}$-alkoxy, $C_{1-6}$-alkylthio, hydroxy, trifluoromethyl, difluoromethyl, fluoromethyl and trifluoromethylsulfonyl.

12. A compound according to claim 11, wherein said optional one or more substituent is selected from the group consisting of halogen, phenyl and methyl.

13. A compound according to claim 9, wherein Q is $CR^{10}$, wherein $R^{10}$ is hydrogen, $C_{1-6}$-alkylcarbonyl, hydroxy, —$NR^{30}COR^{31}$, wherein $R^{30}$ is hydrogen or $C_{1-6}$-alkyl and $R^{31}$ is $C_{1-6}$-alkyl, —$COOR^{16}$, wherein $R^{16}$ is $C_{1-6}$-alkyl; or —$CONR^{17}R^{18}$, wherein $R^{17}$ and $R^{18}$, taken together with the nitrogen to which they are attached, form a piperidinyl, piperazinyl or morpholinyl group, wherein said piperidinyl, piperazinyl and morpholinyl group is unsubstituted or substituted with a $C_{1-6}$-alkyl.

14. A compound according to claim 13, wherein $R^{10}$ is hydrogen, acetyl, hydroxy, —$NR^{30}COR^{31}$, wherein $R^{30}$ is hydrogen and $R^{31}$ is methyl, —$COOR^{16}$, wherein $R^{16}$ is ethyl; or —$CONR^{17}R^{18}$, wherein $R^{17}$ and $R^{18}$, taken together with the nitrogen to which they are attached, form a piperidinyl or a 4-methylpiperazinyl group.

15. A compound according to claim 1, wherein m is 2, 3 or 4.

16. A compound according to claim 15 wherein m is 2.

17. A compound according claim 1, wherein $R^1$ is $R^{11}CO$— or $R^{11}OCO$—, wherein $R^{11}$ is $C_{3-6}$-alkyl, $C_{3-8}$-cycloalkyl, $C_{3-8}$-cycloalkyl-$C_{1-6}$-alkyl, phenyl, phenyl-$C_{1-6}$-alkyl, pyridyl, furanyl, benzo[1,2,5]oxadiazolyl, quinoxalinyl, benzo[b]thiophenyl or naphthalenyl, wherein each of said $C_{3-6}$-alkyl, phenyl, pyridyl and furanyl groups independently are unsubstituted or substituted with one or more substituents selected from the group consisting of halogen, $C_{1-6}$-alkyl, $C_{1-6}$-alkoxy, phenyl and phenoxy, wherein said phenyl and phenoxy independently are unsubstituted or substituted with one halogen; or $R^1$ is $R^{14}R^{15}NCO$—, wherein $R^{14}$ and $R^{15}$ each are independently hydrogen, $C_{1-6}$-alkyl, aryl or aryl-$C_{1-6}$-alkyl, wherein each of said $C_{1-6}$-alkyl and aryl groups independently are unsubstituted or substituted with one substituent selected from the group consisting of halogen and $C_{1-6}$-alkoxy.

18. A compound according to claim 1, wherein $R^2$ is hydrogen.

19. A compound according to claim 1, wherein $R^3$ is hydrogen.

20. A compound according to claim 1, wherein $R^4$ hydrogen or methoxy.

21. A compound according claim 1, wherein $R^5$ hydrogen or methoxy.

22. A compound according to claim 1, wherein $R^6$ hydrogen.

23. A compound according to claim 1, wherein $R^{7a}$ and $R^{7b}$ are hydrogen.

24. A compound according to claim 1, wherein $R^{8a}$ and $R^{8b}$ are hydrogen.

25. A compound according to claim 1 selected from the group consisting of:
- 1-(1-{2-[4-(5-Fluoro-1H-indol-3-yl)-piperidin-1-yl]-ethyl}-3,4-dihydro-1H-isoquinolin-2-yl)-1-(4-fluoro-phenyl)methanone,
- 1-Cyclopentyl-1-(1-{2-[4-(5-fluoro-1H-indol-3-yl)-piperidin-1-yl]-ethyl}-3,4-dihydro-1H-isoquinolin-2-yl)methanone,
- 1-{2-[4-(5-Fluoro-1H-indol-3-yl)-piperidin-1-yl]-ethyl}-3,4-dihydro-1H-isoquinoline-2-carboxylic acid phenethyl-amide,
- 1-(1-{2-[4-(5-Fluoro-1H-indol-3-yl)-piperidin-1-yl]-ethyl}-3,4-dihydro-1H-isoquinolin-2-yl)-1-phenyl-methanone,
- 1-(1-{2-[4-(5-Fluoro-1H-indol-3-yl)-piperidin-1-yl]-ethyl}-3,4-dihydro-1H-isoquinolin-2-yl)-1-(2-fluoro-phenyl)methanone,
- 1-(1-{2-[4-(5-Fluoro-1H-indol-3-yl)-piperidin-1-yl]-ethyl}-3,4-dihydro-1H-isoquinolin-2-yl)-3-phenyl-propan-1-one,
- 1-{2-[4-(5-Fluoro-1H-indol-3-yl)-piperidin-1-yl]-ethyl}-3,4-dihydro-1H-isoquinoline-2-carboxylic acid (3-chloro-propyl)amide,
- 1-{2-[4-(5-Fluoro-1H-indol-3-yl)-piperidin-1-yl]-ethyl}-3,4-dihydro-1H-isoquinoline-2-carboxylic acid (2-methoxy-phenyl)amide,
- 1-{2-[4-(5-Fluoro-1H-indol-3-yl)-piperidin-1-yl]-ethyl}-3,4-dihydro-1H-isoquinoline-2-carboxylic acid tert-butyl ester,
- 3-Chloro-1-(1-{2-[4-(5-fluoro-1H-indol-3-yl)-piperidin-1-yl]-ethyl}-3,4-dihydro-1H-isoquinolin-2-yl)-2,2-dimethyl-propan-1-one,
- 1-Cyclopentyl-1-(1-{2-[6-fluorospiro[isobenzofuran-1(3H),4'-piperidine-1'-yl]-ethyl}-3,4-dihydro-1H-isoquinolin-2-yl)methanone,
- 1-[2-(4-Chloro-phenoxy)-pyridin-3-yl]-1-(1-{2-[6-fluorospiro[isobenzofuran-1(3H),4'-piperidine-1'-yl]-ethyl}-3,4-dihydro-1H-isoquinolin-2-yl)methanone,
- 1-{2-[6-Fluorospiro[isobenzofuran-1(3H),4'-piperidine-1'-yl]-ethyl}-3,4-dihydro-1H-isoquinoline-2-carboxylic acid tert-butyl ester,
- 1-(1-{2-[6-Fluorospiro[isobenzofuran-1(3H),4'-piperidine-1'-yl]-ethyl}-3,4-dihydro-1H-isoquinolin-2-yl)-1-phenylmethanone,
- 1-(1-{2-[6-Fluorospiro[isobenzofuran-1(3H),4'-piperidine-1'-yl]-ethyl}-3,4-dihydro-1H-isoquinolin-2-yl)-1-p-tolylmethanone,
- 1-(1-{2-[6-Fluorospiro[isobenzofuran-1(3H),4'-piperidine-1'-yl]-ethyl}-3,4-dihydro-1H-isoquinolin-2-yl)-1-(2-methoxy-phenyl)methanone,
- 1-Cycloheptyl-1-(1-{2-[6-fluorospiro[isobenzofuran-1(3H),4'-piperidine-1'-yl]-ethyl}-3,4-dihydro-1H-isoquinolin-2-yl)methanone,
- 1-(2-Fluoro-phenyl)-1-(1-{2-[6-fluorospiro[isobenzofuran-1(3H),4'-piperidine-1'-yl]-ethyl}-3,4-dihydro-1H-isoquinolin-2-yl)methanone,
- 1-(2-Chloro-phenyl)-1-(1-{2-[6-fluorospiro[isobenzofuran-1(3H),4'-piperidine-1'-yl]-ethyl}-3,4-dihydro-1H-isoquinolin-2-yl)methanone,
- 1-(4-Fluoro-phenyl)-1-(1-{2-[6-fluorospiro[isobenzofuran-1(3H),4'-piperidine-1'-yl]-ethyl}-3,4-dihydro-1H-isoquinolin-2-yl)methanone,
- 1-(4-Chloro-phenyl)-1-(1-{2-[6-fluorospiro[isobenzofuran-1(3H),4'-piperidine-1'-yl]-ethyl}-3,4-dihydro-1H-isoquinolin-2-yl)methanone,
- 1-{2-[6-Fluorospiro[isobenzofuran-1(3H),4'-piperidine-1'-yl]-ethyl}-3,4-dihydro-1H-isoquinoline-2-carboxylic acid phenethyl amide,
- 1-(1-{2-[6-Fluorospiro[isobenzofuran-1(3H),4'-piperidine-1'-yl]-ethyl}-3,4-dihydro-1H-isoquinolin-2-yl)-1-(4-methoxy-phenyl)methanone,
- 1-(1-{2-[6-Fluorospiro[isobenzofuran-1(3H),4'-piperidine-1'-yl]-ethyl}-3,4-dihydro-1H-isoquinolin-2-yl)-3-phenyl-propan-1-one,
- 2-Ethyl-1-(1-{2-[6-fluorospiro[isobenzofuran-1(3H),4'-piperidine-1'-yl]-ethyl}-3,4-dihydro-1H-isoquinolin-2-yl)-butan-1-one,
- 1-(1-{2-[6-Fluorospiro[isobenzofuran-1(3H),4'-piperidine-1'-yl]-ethyl}-3,4-dihydro-1H-isoquinolin-2-yl)-1-(3-methoxy-phenyl)methanone,
- 1-(1-{2-[6-Fluorospiro[isobenzofuran-1(3H),4'-piperidine-1'-yl]-ethyl}-3,4-dihydro-1H-isoquinolin-2-yl)-2-phenylethanone,
- 3-Cyclohexyl-1-(1-{2-[6-fluorospiro[isobenzofuran-1(3H),4'-piperidine-1'-yl]-ethyl}-3,4-dihydro-1H-isoquinolin-2-yl)-propan-1-one,
- 2-(4-Fluoro-phenyl)-1-(1-{2-[6-fluorospiro[isobenzofuran-1(3H),4'-piperidine-1'-yl]-ethyl}-3,4-dihydro-1H-isoquinolin-2-yl)ethanone,
- 1-{2-[6-Fluorospiro[isobenzofuran-1(3H),4'-piperidine-1'-yl]-ethyl}-3,4-dihydro-1H-isoquinoline-2-carboxylic acid (3,4-dichloro-phenyl)amide,
- 1-Cyclopropyl-1-(1-{2-[6-fluorospiro[isobenzofuran-1(3H),4'-piperidine-1'-yl]-ethyl}-3,4-dihydro-1H-isoquinolin-2-yl)methanone,
- 1-(1-{2-[6-Fluorospiro[isobenzofuran-1(3H),4'-piperidine-1'-yl]-ethyl}-3,4-dihydro-1H-isoquinolin-2-yl)-1-pyridin-3-yl-methanone, 1-[5-(4-Chloro-phenyl)-2-methyl-furan-3-yl]-1(1-{2-[6-fluorospiro[isobenzofuran-1(3H),4'-piperidine-1'-yl]-ethyl}-3,4-dihydro-1H-isoquinolin-2-yl)methano, 2-(4-Chloro-phenyl)-1-(1-{2-[6-fluorospiro[isobenzofuran-1(3H),4'-piperidine-1'-yl]-ethyl}-3,4-dihydro-1H-isoquinolin-2-yl)ethanone 1-(1-{2-[6-Fluorospiro[isobenzofuran-1(3H),4'-piperidine-1'-yl]-ethyl}-3,4-dihydro-1H-isoquinolin-2-yl)-2-methyl-propan-1-one, 1-{2-[6-Fluorospiro[isobenzofuran-1(3H),4'-piperidine-1'-yl]-ethyl}-3,4-dihydro-1H-isoquinoline-2-carboxylic acid (2-ethyl-phenyl)amide, N-[1-{2-[2-(1-Cycloheptyl-methanoyl)-1,2,3,4-tetrahydro-isoquinolin-1-yl]-ethyl}-4-(3-fluorophenyl)-piperidin-4-yl]acetamide, 1-Cyclopentyl-1-(1-{2-[6-fluoro-3-methylspiro[isobenzofuran-1(3H),4'-piperidin-1'-yl]]-ethyl}-3,4-dihydro-1H-isoquinolin-2-yl)methanone, 1-Cycloheptyl-1-{1-[1-acetyl-spiro[2,3-dihydro-1H-indol-3,4'-piperidin-1'-yl]ethyl]-3,4-dihydro-1H-isoquinolin-2-yl}methanone, N-(1-{2-[2-(1-Cycloheptyl-methanoyl)-1,2,3,4-tetrahydro-isoquinolin-1-yl]-ethyl}-4-phenylpiperidin-4-yl)acetamide, 1-Cycloheptyl-1-(1-{2-[6-fluorospiro[isobenzofuran-1(3H),4'-piperidine-1'-yl]-ethyl}-3,4-dihydro-6,7-dimethoxy-1H-isoquinolin-2-yl)methanone, 1-(4-Fluorophenyl)-1-(1-{2-[6-fluoro-3-methylspiro[isobenzofuran-1(3H),4'-piperidine-1'-yl]-ethyl}-3,4-dihydro-1H-isoquinolin-2-yl)methanone, 1-Cycloheptyl-1-(1-{2-[5-fluoro-1-methansulfonyl-spiro[2,3-dihydro-1H-indol-3,4'-piperidin-1'-yl]-ethyl}-3,4-dihydro-1H-isoquinolin-2-yl)methanone, 1-(1-{2-[2-(1-Cycloheptyl-methanoyl)-1,2,3,4-tetrahydro-isoquinolin-1-yl]-ethyl}-4-phenyl-piperidin-4-yl)-1-piperidin-1-ylmethanone, 1-(4-Fluorophenyl)-1-(1-{2-[5-fluoro-1-methansulfonyl-spiro[2,3-dihydro-1H-indol-3,4'-piperidin-1'-yl]-ethyl}-3,4-dihydro-1H-isoquinolin-2-yl)methanone, 1-Cycloheptyl-1-(1-{2-[4-(2-methyl-1H-indol-3-yl)-piperidin-1-yl]-ethyl}-3,4-dihydro-1H-isoquinolin-2-yl)methanone, 1-Cycloheptyl-1-(1-{2-[4-(3-trifluoromethyl-phenyl)-piperidin-1-yl]-ethyl}-3,4-dihydro-1H-isoquinolin-2-yl)methanone, 1-Cyclopentyl-1-(1-{2-[6-fluoro-3-methylspiro[isobenzofuran-1(3H),4'-piperidine-1'-yl]-ethyl}-3,4-dihydro-6,7-dimethoxy-1H-isoquinolin-2-yl)methanone, 1-Cyclopentyl-1-{1-[spiro[2,3-dihydro-1H-indol-3,4'-piperidin-1'-yl]ethyl]-3,4-dihydro-1H-isoquinolin-2-yl}methanone, 1-Cyclopentyl-1-(1-{2-[5-fluoro-1-methansulfonyl-spiro[2,3-dihydro-1H-indol-3,4'-piperidin-1'-yl]-ethyl}-3,4-dihydro-1H-isoquinolin-2-yl)methanone 1-(4-Fluorophenyl)-1-(1-{2-[6-fluoro-3-methylspiro[isobenzofuran-1(3H),4'-piperidine-1'-yl]-ethyl}-3,4-dihydro-6,7-dimethoxy-1H-isoquinolin-2-yl)methanone, 1-(2-Fluorophenyl)-1-(1-{2-[6-fluorospiro[isobenzofuran-1(3H),4'-piperidine-1'-yl]-ethyl}-3,4-dihydro-1H-isoquinolin-2-yl)methanone, 1-Cycloheptyl-1-(1-{2-[spiro[isobenzofuran-1(3H),4'-piperidine-1'-yl]-ethyl}-3,4-dihydro-1H-isoquinolin-2-yl)methanone, 1-Cycloheptyl-1-(1-{2-[6-fluoro-3-methylspiro[isobenzofuran-1(3H),4'-piperidine-1'-yl]-ethyl}-3,4-dihydro-6,7-dimethoxy-1H-isoquinolin-2-yl)methanone, 1-(1-{2-[4-(4-Chloro-phenyl)-piperidin-1-yl]-ethyl}-3,4-dihydro-1H-isoquinolin-2-yl)-1-cycloheptylmethanone, 1-Cyclopentyl-1-(1-{2-[5-isopropylspiro[isobenzofuran-1(3H),4'-piperidine-1'-yl]-ethyl}-3,4-dihydro-1H-isoquinolin-2-yl)methanone, N-[1-{2-[2-(1-Cyclopentyl-methanoyl)-1,2,3,4-tetrahydro-isoquinolin-1-yl]-ethyl}-4-(3-fluorophenyl)-piperidin-4-yl]acetamide, 1-Cycloheptyl-1-{1-[2-(4-phenylpiperidin-1-yl)-ethyl]-3,4-dihydro-1H-isoquinolin-2-yl}methanone, 1-Cycloheptyl-1-(1-{2-[6-fluoro-3-methylspiro[isobenzofuran-1(3H),4'-piperidine-1'-yl]-ethyl}-3,4-dihydro-1H-isoquinolin-2-yl)methanone, 1-Cyclopentyl-1-(1-{2-[4-(3-trifluoromethylphenyl)piperidin-1-yl]-ethyl}-3,4-dihydro-1H-isoquinolin-2-yl)methanone, 1-Cyclopentyl-1-(1-{2-[6-fluorospiro[isobenzofuran-1(3H),4'-piperidine-1'-yl]-ethyl}-3,4-dihydro-6,7-dimethoxy-1H-isoquinolin-2-yl)methanone, 1-(4-Fluorophenyl)-1-(1-{2-[6-fluorospiro[isobenzofuran-1(3H),4'-piperidine-1'-yl]-ethyl}-3,4-dihydro-6,7-dimethoxy-1H-isoquinolin-2-yl)methanone, 1-(1-{2-[4-(6-Fluorobenzo[d]isoxazol-3-yl)-piperidin-1-yl]-ethyl}-3,4-dihydro-1H-isoquinolin-2-yl)-1-(4-fluorophenyl)methanone, 1-[1-(2-{2-[1-(4-Fluorophenyl)-methanoyl]-1,2,3,4-tetrahydro-isoquinolin-1-yl}-ethyl)-4-phenylpiperidin-4-yl]-1-piperidin-1-yl-methanone, 1-Cyclopentyl-1-(1-{2-[4-(3-fluoro-phenyl)-piperidin-1-yl]-ethyl}-3,4-dihydro-1H-isoquinolin-2-yl)methanone, 8-{2-[2-(1-Cycloheptyl-methanoyl)-1,2,3,4-tetrahydro-isoquinolin-1-yl]-ethyl}-1-phenyl-1,3,8-triaza-spiro[4.5]decan-4-one 1-Cycloheptyl-1-(1-{2-[6-trifluoromethylspiro[isobenzofuran-1(3H),4'-piperidine-1'-yl]-ethyl}-3,4-dihydro-6,7-dimethoxy-1H-isoquinolin-2-yl)methanone, 1-[1-(2-{2-[1-(2-Fluoro-phenyl)-methanoyl]-1,2,3,4-tetrahydro-isoquinolin-1-yl}-ethyl)-4-phenyl-piperidin-4-yl]-1-(4-methyl-piperazin-1-yl)methanone, 1-{2-[2-(1-Cycloheptyl-methanoyl)-1,2,3,4-tetrahydro-isoquinolin-1-yl]-ethyl}-4-phenyl-piperidine-4-carboxylic acid ethyl ester, 1-(1-{2-[2-(1-Cycloheptyl-methanoyl)-1,2,3,4-tetrahydro-isoquinolin-1-yl]-ethyl}-4-phenyl-piperidin-4-yl)-ethanone, 1-Cyclopentyl-1-(1-{2-[6-trifluoromethylspiro[isobenzofuran-1(3H),4'-piperidine-1'-yl]-ethyl}-3,4-dihydro-6,7-dimethoxy-1H-isoquinolin-2-yl)methanone, 1-Cyclopentyl-1-(1-{2-[4-(2-methyl-1H-indol-3-yl)-piperidin-1-yl]-ethyl}-3,4-dihydro-1H-isoquinolin-2-yl)methanone, 1-(1-{2-[2-(1-Cyclopentyl-methanoyl)-1,2,3,4-tetrahydro-isoquinolin-1-yl]-ethyl}-4-phenyl-piperidin-4-yl)ethanone, 1-(4-Fluorophenyl)-1-(1-{2-[6-trifluoromethylspiro[isobenzofuran-1(3H),4'-piperidine-1'-yl]-ethyl}-3,4-dihydro-6,7-dimethoxy-1H-isoquinolin-2-yl)methanone, 1-(1-{2-[4-(4-Chloro-phenyl)-piperidin-1-yl]-ethyl}-3,4-dihydro-1H-isoquinolin-2-yl)-1-(4-fluoro-phenyl)methanone, 1-(1-{2-[2-(1-Cycloheptyl-methanoyl)-1,2,3,4-tetrahydro-isoquinolin-1-yl]-ethyl}-piperidin-4-yl)-1-(4-fluoro-phenyl)methanone, 1-(1-{2-[2-(1-Cycloheptyl-methanoyl)-6,7-dimethoxy-1,2,3,4-tetrahydro-isoquinolin-1-yl]-ethyl}-4-phenyl-piperidin-4-yl)-1-(4-methyl-piperazin-1-yl)methanone, 1-(1-{2-[4-(4-Chloro-phenyl)-piperidin-1-yl]-ethyl}-3,4-dihydro-1H-isoquinolin-2-yl)-1-cyclopentylmethanone, 1-(4-Fluoro-phenyl)-1-(1-{2-[4-(3-trifluoromethyl-phenyl)-piperidin-1-yl]-ethyl}-3,4-dihydro-1-isoquinolin-2-yl)methanone, 1-(4-Fluorophenyl)-1-(1-{2-[piro[isobenzofuran-1(3H),4'-piperidine-1'-yl]-ethyl}-3,4-dihydro-1H-isoquinolin-2-yl)methanone, 1-Cyclopentyl-1-(1-{2-[4-fluorospiro[isobenzofuran-1(3H),4'-piperidine-1'-yl]-ethyl}-3,4-dihydro-1H-isoquinolin-2-yl)methanone, 1-(2-Fluorophenyl)-1-(1-{2-[6-fluoro-3-methylspiro[isobenzofuran-1(3H),4'-piperidine-1'-yl]-ethyl}-3,4-dihydro-6,7-dimethoxy-1H-isoquinolin-2-yl)methanone N-[4-(3-Fluoro-phenyl)-1-(2-{2-[1-(4-fluoro-phenyl)-methanoyl]-1,2,3,4-tetrahydro-isoquinolin-1-yl}-ethyl)-piperidin-4-yl]-acetamide, 1-(2-Fluorophenyl)-1-{1-[spiro[2,3-dihydro-1H-indol-3,4'-piperidin-1'-yl]ethyl]-3,4-dihydro-1H-isoquinolin-2-yl}methanone, 1-Cycloheptyl-1-(1-{2-[5-fluoro-1-methansulfonyl-spiro[2,3-dihydro-1H-indol-3,4'-piperidin-1'-yl]-ethyl}-3,4-dihydro-6,7-dimethoxy-1H-isoquinolin-2-yl)methanone, 1-(1-{2-[2-(1-Cycloheptyl-methanoyl)-6,7-dimethoxy-1,2,3,4-tetrahydro-isoquinolin-1-yl]-ethyl}-4-phenyl-piperidin-4-yl)-1-piperidin-1-ylmethanone, 1-{1-[2-(4-Benzyl-piperidin-1-yl)-ethyl]-3,4-dihydro-1H-isoquinolin-2-yl}-1-cycloheptylmethanone, 1-(2-Fluorophenyl)-1-(1-{2-[6-trifluoromethylspiro[isobenzofuran-1(3H),4'-piperidine-1'-yl]-ethyl}-3,4-dihydro-6,7-dimethoxy-1H-isoquinolin-2-yl)methanone, 1-(1-{2-[(Chloro-trifluoromethyl-phenyl)-hydroxy-piperidin-1-yl]-ethyl}-6,7-dimethoxy-3,4-dihydro-1H-isoquinolin-2-yl)-1-cycloheptylmethanone, 1-(1-{2-[4-(4-Chloro-phenyl)-4-hydroxy-piperidin-1-yl]-ethyl}-6,7-dimethoxy-3,4-dihydro-1H-isoquinolin-2-yl)-1-cycloheptylmethanone, 1-Cycloheptyl-1-(1-{2-[4-(2-isopropoxy-phenyl)-piperidin-1-yl]-ethyl}-3,4-dihydro-1H-isoquinolin-2-yl)methanone, 1-(1-{2-[4-(7-Chloro-1H-indol-3-yl)-piperidin-1-yl]-ethyl}-3,4-dihydro-1H-isoquinolin-2-yl)-1-cyclopentylmethanone, 1-Cyclopentyl-1-(1-{2-[4-(2,3-dihydro-benzofuran-7-yl)-piperidin-1-yl]-ethyl}-3,4-dihydro-1H-isoquinolin-2-yl)methanone, 1-(1-{2-[4-(2,3-Dihydro-benzofuran-7-yl)-piperidin-1-yl]-ethyl}-3,4-dihydro-1H-isoquinolin-2-yl)-1-(4-fluoro-phenyl)methanone, N-[1-{2-[2-(1-Cycloheptyl-methanoyl)-6,7-dimethoxy-1,2,3,4-tetrahydro-isoquinolin-1-yl]-ethyl}-4-(3-fluoro-phenyl)-piperidin-4-yl]-acetamide, 1-(4-Fluoro-phenyl)-1-{1-[2-(4-phenyl-piperidin-1-yl)-ethyl]-3,4-dihydro-1H-isoquinolin-2-yl}methanone, 1-(1-{2-[4-(6-Chloro-1H-indol-3-yl)-piperidin-1-yl]-ethyl}-3,4-dihydro-1H-isoquinolin-2-yl)-1-(4-fluoro-phenyl)methanone, 1-(4-Fluoro-phenyl)-1-(1-{2-[4-(3-fluoro-phenyl)-piperidin-1-yl]-ethyl}-3,4-dihydro-1H-isoquinolin-2-yl)methanone 1-Cycloheptyl-1-{1-[spiro[2,3-dihydro-1H-indol-3,4'-piperidin-1'-yl]ethyl]-3,4-dihydro-6,7-dimethoxy-1H-isoquinolin-2-yl}methanone, N-(1-{2-[2-(1-Cyclopentyl-methanoyl)-1,2,3,4-tetrahydro-isoquinolin-1-yl]-ethyl}-4-phenyl-piperidin-4-yl)acetamide, 1-(1-{2-[4-(6-Fluoro-benzo[d]isoxazol-3-yl)-piperidin-1-yl]-ethyl}-3,4-dihydro-1H-isoquinolin-2-yl)-1-(2-fluoro-phenyl)methanone, 1-cycloheptyl-1-(1-{2-[spiro[isobenzofuran-1(3H),4'-piperidine-1'-yl]-ethyl}-3,4-dihydro-6,7-dimethoxy-1H-isoquinolin-2-yl)methanone, 1-{2-[2-(1-Cyclopentyl-methanoyl)-1,2,3,4-tetrahydro-isoquinolin-1-yl]-ethyl}-4-phenyl-piperidine-4-carboxylic acid ethyl ester, 1-(1-{2-[4-(4-Dimethylamino-phenyl)-piperidin-1-yl]-ethyl}-3,4-dihydro-1H-isoquinolin-2-yl)-1-(4-fluoro-phenyl)methanone, 1-Cyclopentyl-1-(1-{2-[4-(4-isopropyl-phenyl)-piperidin-1-yl]-ethyl}-3,4-dihydro-1H-isoquinolin-2-yl)methanone, 1-[1-(2-{2-[1-(4-Fluoro-phenyl)-methanoyl]-1,2,3,4-tetrahydro-isoquinolin-1-yl}-ethyl)-4-phenyl-piperidin-4-yl]ethanone, 1-[1-(2-{2-[1-(2-Fluoro-phenyl)-methanoyl]-1,2,3,4-tetrahydro-isoquinolin-1-yl}-ethyl)-4-phenyl-piperidin-4-yl]ethanone, 1-[1-(2-{2-[1-(2-Fluoro-phenyl)-methanoyl]-1,2,3,4-tetrahydro-isoquinolin-1-yl}-ethyl)-4-phenyl-piperidin-4-yl]-1-piperidin-1-yl-methanone, 1-Cyclopentyl-1-{1-[2-(4-phenyl-piperidin-1-yl)-ethyl]-3,4-dihydro-1H-isoquinolin-2-yl}methanone, 1-(2-Fluorophenyl)-1-(1-{2-[6-fluorospiro[isobenzofuran-1(3H),4'-piperidine-1'-yl]-ethyl}-3,4-dihydro-6,7-dimethoxy-1H-isoquinolin-2-yl)methanone, 1-(4-Fluoro-phenyl)-1-(1-{2-[5,6-difluorospiro[benzofuran-1(3H),4'-piperidine-1'-yl]-ethyl}-3,4-dihydro-1H-isoquinolin-2-yl)-methanone, 1-(4-Fluorophenyl)-1-({2-[6-fluorospiro[benzofuran-1(3H),4'-piperidine-1'-yl]-ethyl}-3,4-dihydro-1H-isoquinolin-2-yl)methanone 3,3-Dimethyl-[1-{2-[spiro(5-fluor-benzofuran-2H-3,4'-piperidine-1'-yl)-]ethyl}-3,4-dihydro-1H-isoquinoline-2-yl]-butan-1-one, Cyclohexyl-[1-{2-[spiro(5-fluor-benzofuran-2H-3,4'-piperidine-1'-yl)-]ethyl}-3,4-dihydro-1H-isoquinoline-2-yl]-methanone Cyclohexyl-(1-{2-[spiro(5-methyl-isobenzofuran-3H-1,4'-piperidine-1'-yl)-]ethyl}-3,4-dihydro-1H-isoquinolin-2-yl)-methanone, Cyclohexyl-[1-{2-[spiro(benzofuran-3H-1,4'-piperidine-1'-yl)-]ethyl}-3,4-dihydro-1H-isoquinoline-2-yl]-methanone, Cyclohexyl-(1-{2-[4-(2-methyl-1H-indol-3-yl)-piperidin-1-yl]-ethyl}-3,4-dihydro-1H-isoquinolin-2-yl)-methanone, N-{1-[2-(2-Cyclohexanecarbonyl-1,2,3,4-tetrahydro-isoquinolin-1-yl)-ethyl]-4-phenyl-piperidin-4-yl}-acetamide, 3,3-Dimethyl-1-(1-{2-[4-(3-trifluoromethyl-phenyl)-piperidin-1-yl]-ethyl}-3,4-dihydro-1H-isoquinolin-2-yl)-butan-1-one, Cyclohexyl-(1-{2-[4-(3-trifluoromethyl-phenyl)-piperidin-1-yl]-ethyl}-3,4-dihydro-1H-isoquinolin-2-yl)-methanone, Cyclohexyl-(1-{2-[4-(4-dimethylamino-phenyl)-piperidin-1-yl]-ethyl}-3,4-dihydro-1H-isoquinolin-2-yl)-methanone,
3-Phenyl-[1-{2-[spiro(5-fluor-benzofuran-2H-3,4'-piperidine-1'-yl)-]ethyl}-3,4-dihydro-1H-isoquinoline-2-yl]-propanone,
(1-{2-[4-(4-Chloro-3-trifluoromethyl-phenyl)-4-hydroxy-piperidin-1-yl]-ethyl}-6,7-dimethoxy-3,4-dihydro-1H-isoquinolin-2-yl)-cyclohexyl-methanone,
2-Phenoxy-[1-{2-[spiro(5-fluor-benzofuran-2H-3,4'-piperidine-1'-yl)-]ethyl}-3,4-dihydro-1H-isoquinoline-2-yl]-ethan-1-one,
Benzo[1,2,5]oxadiazol-5-yl-(1-{2-[spiro(5-methyl-isobenzofuran-3H-1,4'-piperidine-1'-yl)-]ethyl}-3,4-dihydro-1H-isoquinolin-2-yl)-methanone,
Cyclohexyl-(1-{2-[4-(4-isopropyl-phenyl)-piperidin-1-yl]-ethyl}-3,4-dihydro-1H-isoquinolin-2-yl)-methanone,
2-Propyl-[1-{2-[spiro(5-fluor-benzofuran-2H-3,4'-piperidine-1'-yl)-]ethyl}-3,4-dihydro-1H-isoquinoline-2-yl]-pentan-1-one,
2,2-Dimethyl-3-chlor-[1-{2-[spiro(5-fluor-benzofuran-2H-3,4'-piperidine-1'-yl)-]ethyl}-3,4-dihydro-1H-isoquinoline-2-yl]-propan-1-one,
Cyclohexyl-(1-{2-[4-(2,3-dihydro-benzofuran-7-yl)-piperidin-1-yl]-ethyl}-3,4-dihydro-1H-isoquinolin-2-yl)-methanone,
3,3-Dimethyl-(1-{2-[spiro(5-methyl-isobenzofuran-3H-1,4'-piperidine-1'-yl)-]ethyl}-3,4-dihydro-1H-isoquinolin-2-yl)-butan-1-one,
Benzo[1,2,5]oxadiazol-5-yl-(1-{2-[4-(3-trifluoromethyl-phenyl)-piperidin-1-yl]-ethyl}-3,4-dihydro-1H-isoquinolin-2-yl)-methanone,
2-Ethyl-1-(1-{2-[4-(3-trifluoromethyl-phenyl)-piperidin-1-yl]-ethyl}-3,4-dihydro-1H-isoquinolin-2-yl)-butan-1-one,
2-Benzyloxy-(1-{2-[spiro(5-methyl-isobenzofuran-3H-1,4'-piperidine-1'-yl)-]ethyl}-3,4-dihydro-1H-isoquinolin-2-yl)-ethan-1-one,
Benzo[1,2,5]oxadiazol-5-yl-[1-{2-[spiro(5-fluor-benzofuran-2H-3,4'-piperidine-1'-yl)]-ethyl}-3,4-dihydro-1H-isoquinoline-2-yl]-methanone,
(1-{2-[4-(4-Chloro-phenyl)-piperidin-1-yl]-ethyl}-3,4-dihydro-1H-isoquinolin-2-yl)-cyclohexyl-methanone,
1-(1-{2-[4-(4-Chloro-phenyl)-piperidin-1-yl]-ethyl}-3,4-dihydro-1H-isoquinolin-2-yl)-3,3-dimethyl-butan-1-one,
3,5,5-Trimethyl-[1-{2-[spiro(5-fluor-benzofuran-2H-3,4'-piperidine-1'-yl)-]ethyl}-3,4-dihydro-1H-isoquinoline-2-yl]-hexan-1-one
3,5,5-Trimethyl-(1-{2-[spiro(5-methyl-isobenzofuran-3H-1,4'-piperidine-1'-yl)-]ethyl}-3,4-dihydro-1H-isoquinolin-2-yl)-hexan-1-one,
2-Phenoxy-(1-{2-[spiro(5-methyl-isobenzofuran-3H-1,4'-piperidine-1'-yl)-]ethyl}-3,4-dihydro-1H-isoquinolin-2-yl)-ethan-1-one,
(1-{2-[4-(4-Chloro-phenyl)-piperidin-1-yl]-ethyl}-3,4-dihydro-1H-isoquinolin-2-yl)-(2,2-dichloro-cyclopropyl)-methanone,
2-Benzyloxy-[1-{2-[spiro(5-fluor-benzofuran-2H-3,4'-piperidine-1'-yl)-]ethyl}-3,4-dihydro-1H-isoquinoline-2-yl]-ethan-1-one,
1-(1-{2-[4-(4-Chloro-3-trifluoromethyl-phenyl)-4-hydroxy-piperidin-1-yl]-ethyl}-6,7-dimethoxy-3,4-dihydro-1H-isoquinolin-2-yl)-3,3-dimethyl-butan-1-one,
1-(1-{2-[4-(2,3-Dihydro-benzofuran-7-yl)-piperidin-1-yl]-ethyl}-3,4-dihydro-1H-isoquinolin-2-yl)-3,3-dimethyl-butan-1-one,
3,5,5-Trimethyl-1-(1-{2-[4-(3-trifluoromethyl-phenyl)-piperidin-1-yl]-ethyl}-3,4-dihydro-1H-isoquinolin-2-yl)-hexan-1-one,
2,2-Dimethyl-[1-{2-[spiro(5-fluor-benzofuran-2H-3,4'-piperidine-1'-yl)-]ethyl}-3,4-dihydro-1H-isoquinoline-2-yl]-propan-1-one,
3-Cyclohexyl-1-(1-{2-[4-(3-trifluoromethyl-phenyl)-piperidin-1-yl]-ethyl}-3,4-dihydro-1H-isoquinolin-2-yl)-propan-1-one,
Furan-2-yl-[1-{2-[spiro(5-fluor-benzofuran-2H-3,4'-piperidine-1'-yl)-]ethyl}-3,4-dihydro-1H-isoquinoline-2-yl]-methanone,
N-(4-Phenyl-1-{2-[2-(3,5,5-trimethyl-hexanoyl)-1,2,3,4-tetrahydro-isoquinolin-1-yl]-ethyl}-piperidin-4-yl)-acetamide,
Quinoxalin-2-yl-[1-{2-[spiro(5-fluor-benzofuran-2H-3,4'-piperidine-1'-yl)-]ethyl}-3,4-dihydro-1H-isoquinoline-2-yl]-methanone,
3-Cyclohexyl-[1-{2-[spiro(5-fluor-benzofuran-2H-3,4'-piperidine-1'-yl)-]ethyl}-3,4-dihydro-1H-isoquinoline-2-yl]-propan-1-one,
Benzo[1,2,5]oxadiazol-5-yl-(1-{2-[4-(2,3-dihydro-benzofuran-7-yl)-piperidin-1-yl]-ethyl}-3,4-dihydro-1H-isoquinolin-2-yl)-methanone,
Benzo[1,2,5]oxadiazol-5-yl-(1-{2-[4-(2-methyl-1H-indol-3-yl)-piperidin-1-yl]-ethyl}-3,4-dihydro-1H-isoquinolin-2-yl)-methanone,
(Tetrahydro-pyran-4-yl)-(1-{2-[4-(3-trifluoromethyl-phenyl)-piperidin-1-yl]-ethyl}-3,4-dihydro-1H-isoquinolin-2-yl)-methanone,
2-Propyl-1-(1-{2-[4-(3-trifluoromethyl-phenyl)-piperidin-1-yl]-ethyl}-3,4-dihydro-1H-isoquinolin-2-yl)-pentan-1-one,
2-Ethyl-[1-{2-[spiro(5-fluor-benzofuran-2H-3,4'-piperidine-1'-yl)-]ethyl}-3,4-dihydro-1H-isoquinoline-2-yl]-butan-1-one,
3-Phenyl-1-(1-{2-[4-(3-trifluoromethyl-phenyl)-piperidin-1-yl]-ethyl}-3,4-dihydro-1H-isoquinolin-2-yl)-propan-1-one,
3,3-Dimethyl-1-(1-{2-[4-(2-methyl-1H-indol-3-yl)-piperidin-1-yl]-ethyl}-3,4-dihydro-1H-isoquinolin-2-yl)-butan-1-one,
(1-{2-[4-(4-Chloro-3-trifluoromethyl-phenyl)-4-hydroxy-piperidin-1-yl]-ethyl}-6,7-dimethoxy-3,4-dihydro-1H-isoquinolin-2-yl)-(2,2-dichloro-cyclopropyl)-methanone,
1,2,3,4-tetrahydro-naphthalene-2-yl-(1-{2-[spiro(5-methyl-isobenzofuran-3H-1,4'-piperidine-1'-yl)-]ethyl}-3,4-dihydro-1H-isoquinolin-2-yl)-methanone,
(4-Methylsulfanyl-phenyl)-(1-{2-[4-(3-trifluoromethyl-phenyl)-piperidin-1-yl]-ethyl}-3,4-dihydro-1H-isoquinolin-2-yl)-methanone,
3,5,5-Trimethyl-1-(1-{2-[4-(2-methyl-1H-indol-3-yl)-piperidin-1-yl]-ethyl}-3,4-dihydro-1H-isoquinolin-2-yl)-hexan-1-one,
3-Phenyl-(1-{2-[spiro(5-methyl-isobenzofuran-3H-1,4'-piperidine-1'-yl)-]ethyl}-3,4-dihydro-1H-isoquinolin-2-yl)-propan-1-one,
Furan-2-yl-(1-{2-[4-(3-trifluoromethyl-phenyl)-piperidin-1-yl]-ethyl}-3,4-dihydro-1H-isoquinolin-2-yl)-methanone,
2-Benzyloxy-1-(1-{2-[4-(2-methyl-1H-indol-3-yl)-piperidin-1-yl]-ethyl}-3,4-dihydro-1H-isoquinolin-2-yl)-ethanone, 1-(1-{2-[4-(4-Chloro-phenyl)-piperidin-1-yl]-ethyl}-3,4-dihydro-1H-isoquinolin-2-yl)-2-phenoxy-ethanone,
Quinoxalin-2-yl-(1-{2-[spiro(5-methyl-isobenzofuran-3H-1,4'-piperidine-1'-yl)-]ethyl}-3,4-dihydro-1H-isoquinolin-2-yl)-methanone,
2,2-Dimethyl-1-(1-{2-[4-(3-trifluoromethyl-phenyl)-piperidin-1-yl]-ethyl}-3,4-dihydro-1H-isoquinolin-2-yl)-propan-1-one,
(2,2-Dichloro-cyclopropyl)-(1-{2-[4-(3-trifluoromethyl-phenyl)-piperidin-1-yl]-ethyl}-3,4-dihydro-1H-isoquinolin-2-yl)-methanone,
4-Methylsulfanyl-phenyl-(1-{2-[spiro(5-methyl-isobenzofuran-3H-1,4'-piperidine-1'-yl)]ethyl}-3,4-dihydro-1H-isoquinolin-2-yl)-methanone,
(2,2-Dichloro-cyclopropyl)-(1-{2-[4-(2,3-dihydro-benzofuran-7-yl)-piperidin-1-yl]-ethyl}-3,4-dihydro-1H-isoquinolin-2-yl)-methanone,
1-(1-{2-[4-(4-Isopropyl-phenyl)-piperidin-1-yl]-ethyl}-3,4-dihydro-1H-isoquinolin-2-yl)-3,5,5-trimethyl-hexan-1-one,
2,2-Dichloro-cyclopropyl-(1-{2-[spiro(isobenzofuran-3H-1,4'-piperidine-1'-yl)-]ethyl}-3,4-dihydro-1H-isoquinolin-2-yl)-methanone,
N-(4-Phenyl-1-{2-[2-(1,2,3,4-tetrahydro-naphthalene-2-carbonyl)-1,2,3,4-tetrahydro-isoquinolin-1-yl]-ethyl}-piperidin-4-yl)-acetamide,
Benzo[1,2,5]oxadiazol-5-yl-(1-{2-[4-(4-chloro-phenyl)-piperidin-1-yl]-ethyl}-3,4-dihydro-1H-isoquinolin-2-yl)-methanone,
N-(1-{2-[2-(3,3-Dimethyl-butyryl)-1,2,3,4-tetrahydro-isoquinolin-1-yl]-ethyl}-4-phenyl-piperidin-4-yl)-acetamide,
3-Chloro-2,2-dimethyl-1-(1-{2-[4-(3-trifluoromethyl-phenyl)-piperidin-1-yl]-ethyl}-3,4-dihydro-1H-isoquinolin-2-yl)-propan-1-one,
Tetrahydro-pyran-4-yl-[1-{2-[spiro(5-fluor-benzofuran-2H-3,4'-piperidine-1'-yl)-]ethyl}-3,4-dihydro-1H-isoquinoline-2-yl]-butan-1-one,
1-(1-{2-[4-(5-Fluoro-1H-indol-3-yl)-piperidin-1-yl]-ethyl}-5-chloro-3,4-dihydro-1H-isoquinolin-2-yl)-1-(4-fluoro-phenyl)methanone,
1-Cyclopentyl-1-(1-{2-[4-(5-fluoro-1H-indol-3-yl)-piperidin-1-yl]-ethyl }-5-chloro-3,4-dihydro-1H-isoquinolin-2-yl)methanone,
1-Cyclopentyl-1-(1-{2-[6-fluorospiro[isobenzofuran-1(3H),4'-piperidine-1'-yl]-ethyl}-5-Chloro-3,4-dihydro-1H-isoquinolin-2-yl)methanone,
1-(4-Fluorophenyl)-1-(1-{2-[6-fluorospiro[isobenzofuran-1(3H),4'-piperidine-1'-yl]-ethyl}-5-chloro-3,4-dihydro-1H-isoquinolin-2-yl)methanone,
1-Cyclopentyl-1-(1-{2-[6-trifluoromethylspiro[isobenzofuran-1(3H),4'-piperidine-1'-yl]-ethyl}-5-chloro-3,4-dihydro-1H-isoquinolin-2-yl)methanone,
1-(4-Fluorophenyl)-1-(1-{2-[6-trifluoromethylspiro[isobenzofuran-1(3H),4'-piperidine-1'-yl]-ethyl}-5-chloro-3,4-dihydro-1H-isoquinolin-2-yl)methanone,
N-[1-{2-[2-(1-Cyclopentyl-methanoyl)-1,2,3,4-tetrahydro-isoquinolin-1-yl]-ethyl}-4-(3-fluorophenyl)-piperidin-4-yl]acetamide,
N-[1-{2-[2-(1-(4-Fluorophenyl)-methanoyl)-1,2,3,4-tetrahydro-isoquinolin-1-yl]-ethyl}-4-(3-fluorophenyl)-piperidin-4-yl]acetamide,
N-[1-{2-[2-(1-Cyclopentyl-methanoyl)-1,2,3,4-tetrahydro-isoquinolin-1-yl]-ethyl}-4-phenylpiperidin-4-yl]acetamide,
N-[1-{2-[2-(1-(4-Fluorophenyl)-methanoyl)-1,2,3,4-tetrahydro-isoquinolin-1-yl]-ethyl}-4-phenylpiperidin-4-yl]acetamide,
1-Cyclopentyl-1-{1-[1-acetyl-spiro[2,3-dihydro-1H-indol-3,4'-piperidine-1'-yl]ethyl]-5-chloro-3,4-dihydro-1H-isoquinolin-2-yl}methanone,
1-(4-Fluorophenyl)-1-{1-[1-acetyl-spiro[2,3-dihydro-1H-indol-3,4'-piperidine-1'-yl]ethyl]-5-chloro-3,4-dihydro-1H-isoquinolin-2-yl}methanone,
1-Cyclopentyl-1-{1-[1-acetyl-spiro[2,3-dihydro-5-fluoro 1H-indol-3,4'-piperidine-1'-yl]-ethyl]-5-chloro-3,4-dihydro-1H-isoquinolin-2-yl}methanone,
1-(4-Fluorophenyl)-1-{1-[1-acetyl-spiro[2,3-dihydro-5-fluoro-1H-indol-3,4'-piperidine-1'-yl]ethyl]-5-chloro-3,4-dihydro-1H-isoquinolin-2-yl}methanone,
1-Cyclopentyl-1-(1-{2-[4-(3-trifluoromethylphenyl)-piperidin-1-yl]-ethyl}-5-chloro-3,4-dihydro-1H-isoquinolin-2-yl)methanone,
1-(4-Fluorophenyl)-1-(1-{2-[4-(3-trifluoromethylphenyl)-piperidin-1-yl]-ethyl}-5-chloro-3,4-dihydro-1H-isoquinolin-2-yl)methanone,
1-(1-{2-[4-(6-Fluorobenzo[d]isoxazol-3-yl)-piperidin-1-yl]-ethyl}-5-chloro-3,4-dihydro-1H-isoquinolin-2-yl)-1-(4-fluorophenyl)methanone,
1-(1-{2-[4-(6-Fluorobenzo[d]isoxazol-3-yl)-piperidin-1-yl]-ethyl}-5-chloro-3,4-dihydro-1H-isoquinolin-2-yl)-1-(cyclopentyl)methanone,
1-(4-Fluorophenyl)-1-(1-{2-[5,6-difluorospiro[benzofuran-1(3H),4'-piperidine-1'-yl]-ethyl}-5chloro-3,4-dihydro-1H-isoquinolin-2-yl)-methanone,
1-(4-Fluorophenyl)-1-({2-[6-fluorospiro[benzofuran-1(3H),4'-piperidine-1'-yl]-ethyl}-5-chloro-3,4-dihydro-1H-isoquinolin-2-yl)methanone,
1-Cyclopentyl-1-(1-{2-[5,6-difluorospiro[benzofuran-1(3H),4'-piperidine-1'-yl]-ethyl}-5-chloro-3,4-dihydro-1H-isoquinolin-2-yl)-methanone,
1-Cyclopentyl-1-({2-[6-fluorospiro[benzofuran-1(3H),4'-piperidine-1'-yl]-ethyl}-5-chloro-3,4-dihydro-1H-isoquinolin-2-yl)methanone,
1-(1-{2-[4-(5-Fluoro-1H-indol-3-yl)-piperidin-1-yl]-ethyl}-3,4-dihydro-5-fluoro-1H-isoquinolin-2-yl)-1-(4-fluoro-phenyl)methanone,
1-Cyclopentyl-1-(1-{2-[4-(5-fluoro-1H-indol-3-yl)-piperidin-1-yl]-ethyl}-3,4-dihydro-5-fluoro-1H-isoquinolin-2-yl)methanone,
1-Cyclopentyl-1-(1-{2-[6-fluorospiro[isobenzofuran-1(3H),4'-piperidine-1'-yl]-ethyl}-3,4-dihydro-5-fluoro-1H-isoquinolin-2-yl)methanone,
1-(4-Fluorophenyl)-1-(1-{2-[6-fluorospiro[isobenzofuran-1(3H),4'-piperidine-1'-yl]-ethyl}-3,4-dihydro-5-fluoro-1H-isoquinolin-2-yl)methanone,
1-Cyclopentyl-1-(1-{2-[6-trifluoromethylspiro[isobenzofuran-1(3H),4'-piperidine-1'-yl]-ethyl}-3,4-dihydro-5-fluoro-1H-isoquinolin-2-yl)methanone,
1-(4-Fluorophenyl)-1-(1-{2-[6-trifluoromethylspiro[isobenzofuran-1(3H),4'-piperidine-1'-yl]ethyl}-3,4-dihydro-5-fluoro-1H-isoquinolin-2-yl)methanone,
N-[1-{2-[2-(1-Cyclopentyl-methanoyl)-1,2,3,4-tetrahydro-isoquinolin-1-yl]-ethyl}-4-(3-fluorophenyl)-piperidin-4-yl]acetamide,
N-[1-{2-[2-(1-(4-Fluorophenyl)-methanoyl)-1,2,3,4-tetrahydro-isoquinolin-1-yl]-ethyl}-4-(3-fluorophenyl)-piperidin-4-yl]acetamide,
N-[1-{2-[2-(1-Cyclopentyl-methanoyl)-1,2,3,4-tetrahydro-isoquinolin-1-yl]-ethyl}-4-phenylpiperidin-4-yl]acetamide, N-[1-{2-[2-(1-(4-Fluorophenyl)-methanoyl)-1,2,3,4-tetrahydro-isoquinolin-1-yl]-ethyl}-4-phenylpiperidin-4-yl]acetamide,
1-Cyclopentyl-1-{1-[1-acetyl-spiro[2,3-dihydro-1H-indol-3,4'-piperidin-1'-yl]ethyl]-3,4-dihydro-5-fluoro-1H-isoquinolin-2-yl}methanone,
1-(4-Fluorophenyl)-1-{1-[1-acetyl-spiro[2,3-dihydro-1H-indol-3,4'-piperidin-1'-yl]ethyl]-3,4-dihydro-5-fluoro-1H-isoquinolin-2-yl}methanone,
1-Cyclopentyl-1-{1-[1-acetyl-spiro[2,3-dihydro-5-fluoro1H -indol-3,4'-piperidin-1'-yl]-ethyl]-3,4-dihydro-5-fluoro-1H-isoquinolin-2-yl}methanone,
1-(4-Fluorophenyl)-1-{1-[1-acetyl-spiro[2,3-dihydro-5-fluoro-1H-indol-3,4'-piperidin-1'-yl]ethyl]-3,4-dihydro-5-fluoro-1H-isoquinolin-2-yl}methanone,
1-Cyclopentyl-1-(1-{2-[4-(3-trifluoromethylphenyl)-piperidin-1-yl]-ethyl}-3,4-dihydro-5-fluoro-1H-isoquinolin-2-yl)methanone,
1-(4-Fluorophenyl)-1-(1-{2-[4-(3-trifluoromethylphenyl)-piperidin-1-yl]-ethyl}-3,4-dihydro-5-fluoro-1H-isoquinolin-2-yl)methanone,
1-(1-{2-[4-(6-Fluorobenzo[d]isoxazol-3-yl)-piperidin-1-yl]-ethyl}-3,4-dihydro-5-fluoro-1H-isoquinolin-2-yl)-1-(4-fluorophenyl)methanone,
1-(1-{2-[4-(6-Fluorobenzo[d]isoxazol-3-yl)-piperidin-1-yl]-ethyl}-3,4-dihydro-5-fluoro-1H-isoquinolin-2-yl)-1-(cyclopentyl)methanone,
1-(4-Fluorophenyl)-1-(1-{2-[5,6-difluorospiro[benzofuran-1(3H),4'-piperidine-1'-yl]-ethyl}-3,4-dihydro-5-fluoro-1H-isoquinolin-2-yl)-methanone,
1-(4-Fluorophenyl)-1-({2-[6-fluorospiro[benzofuran-1(3H),4'-piperidine-1'-yl]-ethyl}-3,4-dihydro-5-fluoro-1H-isoquinolin-2-yl)methanone,
1-Cyclopentyl-1-(1-{2-[5,6-difluorospiro[benzofuran-1(3H),4'-piperidine-1'-yl]-ethyl}-3,4-dihydro-5-fluoro-1H-isoquinolin-2-yl)-methanone,
1-Cyclopentyl-1-({2-[6-fluorospiro[benzofuran-1(3H),4'-piperidine-1'-yl]-ethyl}-3,4-dihydro-5-fluoro-1H-isoquinolin-2-yl)methanone,
1-(1-{2-[4-(5-Fluoro-1H-indol-3-yl)-piperidin-1-yl]-ethyl}-5,6-dichloro-3,4-dihydro-1H-isoquinolin-2-yl)-1-(4-fluoro-phenyl)methanone,
1-Cyclopentyl-1-(1-{2-[4-(5-fluoro-1H-indol-3-yl)-piperidin-1-yl]-ethyl}-5,6-dichloro-3,4-dihydro-1H-isoquinolin-2-yl)methanone,
1-Cyclopentyl-1-(1-{2-[6-fluorospiro[isobenzofuran-1(3H),4'-piperidine-1'-yl]-ethyl}-5,6-dichloro-3,4-dihydro-1H-isoquinolin-2-yl)methanone,
1-(4-Fluorophenyl)-1-(1-{2-[6-fluorospiro[isobenzofuran-1(3H),4'-piperidine-1'-yl]-ethyl}-5,6-dichloro-3,4-dihydro-1H-isoquinolin-2-yl)methanone,
1-Cyclopentyl-1-(1-{2-[6-trifluoromethylspiro[isobenzofuran-1(3H),4'-piperidine-1'-yl]-ethyl}-5,6-dichloro-3,4-dihydro-1H-isoquinolin-2-yl)methanone,
1-(4-Fluorophenyl)-1-(1-{2-[6-trifluoromethylspiro[isobenzofuran-1(3H),4'-piperidine-1'-yl]ethyl}-5,6-dichloro-3,4-dihydro-1H-isoquinolin-2-yl)methanone,
N-[1-{2-[2-(1-Cyclopentyl-methanoyl)-1,2,3,4-tetrahydro-isoquinolin-1-yl]-ethyl}-4-(3-fluorophenyl)-piperidin-4-yl]acetamide,
N-[1-{2-[2-(1-(4-Fluorophenyl)-methanoyl)-1,2,3,4-tetrahydro-isoquinolin-1-yl]-ethyl}-4-(3-fluorophenyl)-piperidin-4-yl]acetamide,
N-[1-{2-[2-(1-Cyclopentyl-methanoyl)-1,2,3,4-tetrahydro-isoquinolin-1-yl]-ethyl}-4-phenylpiperidin-4-yl]acetamide, N-[1-{2-[2-(1-(4-Fluorophenyl)-methanoyl)-1,2,3,4-tetrahydro-isoquinolin-1-yl]-ethyl}-4-phenylpiperidin-4-yl]acetamide,
1-Cyclopentyl-1-{1-[1-acetyl-spiro[2,3-dihydro-1H-indol-3,4'-piperidin-1'-yl]ethyl]-5,6-dichloro-3,4-dihydro-1H-isoquinolin-2-yl}methanone,
1-(4-Fluorophenyl)-1-{1-[1-acetyl-spiro[2,3-dihydro-1H-indol-3,4'-piperidin-1'-yl]ethyl]-5,6-dichloro-3,4-dihydro-1H-isoquinolin-2-yl}methanone,
1-Cyclopentyl-1-{1-[1-acetyl-spiro[2,3-dihydro-5-fluoro1H-indol-3,4'-piperidin-1'-yl]-ethyl]-5,6-dichloro-3,4-dihydro-1H-isoquinolin-2-yl}methanone,
1-(4-Fluorophenyl)-1-{1-[-acetyl-spiro[2,3-dihydro-5-fluoro-1H-indol-3,4'-piperidin-1'-yl]ethyl]-5,6-dichloro-3,4-dihydro-1H-isoquinolin-2-yl}methanone,
1-Cyclopentyl-1-(1-{2-[4-(3-trifluoromethylphenyl)-piperidin-1-yl]-ethyl}-5,6-dichloro-3,4-dihydro-1H-isoquinolin-2-yl)methanone,
1-(4-Fluorophenyl)-1-(1-{2-[4-(3-trifluoromethylphenyl)-piperidin-1-yl]-ethyl}-5,6-dichloro-3,4-dihydro-1H-isoquinolin-2-yl)methanone,
1-(1-{2-[4-(6-Fluorobenzo[d]isoxazol-3-yl)-piperidin-1-yl]-ethyl}-5,6-dichloro-3,4-dihydro-1H-isoquinolin-2-yl)-1-(4-fluorophenyl)methanone,
1-(1-{2-[4-(6-Fluorobenzo[d]isoxazol-3-yl)-piperidin-1-yl]-ethyl}-5,6-dichloro-3,4-dihydro-1H-isoquinolin-2-yl)-1-(cyclopentyl)methanone,
1-(4-Fluorophenyl)-1-(1-{2-[5,6-difluorospiro[benzofuran-1(3H),4'-piperidine-1'-yl]-ethyl}-5,6-dichloro-3,4-dihydro-1H-isoquinolin-2-yl)-methanone,
1-(4-Fluorophenyl)-1-({2-[6-fluorospiro[benzofuran-1(3H),4'-piperidine-1'-yl]-ethyl}-5,6-dichloro-3,4-dihydro-1H-isoquinolin-2-yl)methanone,
1-Cyclopentyl-1-(1-{2-[5,6-difluorospiro[benzofuran-1(3H),4'-piperidine-1'-yl]-ethyl}-5,6-dichloro-3,4-dihydro-1H-isoquinolin-2-yl)-methanone,
1-Cyclopentyl-1-({2-[6-fluorospiro[benzofuran-1(3H),4'-piperidine-1'-yl]-ethyl}-5,6-dichloro-3,4-dihydro-1H-isoquinolin-2-yl)methanone,
1-(1-{2-[4-(5-Fluoro-1H-indol-3-yl)-piperidin-1-yl]-ethyl}-5,6-difluoro-3,4-dihydro-1H-isoquinolin-2-yl)-1-(4-fluoro-phenyl)methanone,
1-Cyclopentyl-1-(1-{2-[4-(5-fluoro-1H-indol-3-yl)-piperidin-1-yl]-ethyl}-5,6-difluoro-3,4-dihydro-1H-isoquinolin-2-yl)methanone,
1-Cyclopentyl-1-(1-{2-[6-fluorospiro[isobenzofuran-1(3H),4'-piperidine-1'-yl]-ethyl}-5,6-difluoro-3,4-dihydro-1H-isoquinolin-2-yl)methanone,
1-(4-Fluorophenyl)-1-(1-{2-[6-fluorospiro[isobenzofuran-1(3H),4'-piperidine-1'-yl]-ethyl}-5,6-difluoro-3,4-dihydro-1H-isoquinolin-2-yl)methanone,
1-Cyclopentyl-1-(1-{2-[6-trifluoromethylspiro[isobenzofuran-1(3H),4'-piperidine-1'-yl]-ethyl}-5,6-difluoro-3,4-dihydro-1H-isoquinolin-2-yl)methanone,
1-(4-Fluorophenyl)-1-(1-{2-[6-trifluoromethylspiro[isobenzofuran-1(3H),4'-piperidine-1'-yl]ethyl}-5,6-difluoro-3,4-dihydro-1H-isoquinolin-2-yl)methanone,
N-[1-{2-[2-(1-Cyclopentyl-methanoyl)-1,2,3,4-tetrahydro-isoquinolin-1-yl]-ethyl}-4-(3-fluorophenyl)-piperidin-4-yl]acetamide,
N-[1-{2-[2-(1-(4-Fluorophenyl)-methanoyl)-1,2,3,4-tetrahydro-isoquinolin-1-yl]-ethyl}-4-(3-fluorophenyl)-piperidin-4-yl]acetamide,
N-[1-{2-[2-(1-Cyclopentyl-methanoyl)-1,2,3,4-tetrahydro-isoquinolin-1-yl]-ethyl}-4-phenylpiperidin-4-yl]acetamide, N-[1-{2-[2-(1-(4-Fluorophenyl)-methanoyl)-1,2,3,4-tetrahydro-isoquinolin-1-yl]-ethyl}-4-phenylpiperidin-4-yl]acetamide, 1-Cyclopentyl-1-{1-[1-acetyl-spiro[2,3-dihydro-1H-indol-3,4'-piperidin-1'-yl]ethyl]-5,6-difluoro-3,4-dihydro-1H-isoquinolin-2-yl}methanone, 1-(4-Fluorophenyl)-1-{1-[1-acetyl-spiro[2,3-dihydro-1H-indol-3,4'-piperidin-1'-yl]ethyl]-5,6-difluoro-3,4-dihydro-1H-isoquinolin-2-yl}methanone, 1-Cyclopentyl-1-{1-[1-acetyl-spiro[2,3-dihydro-5-fluoro 1H-indol-3,4'-piperidin-1'-yl]-ethyl]-5,6-difluoro-3,4-dihydro-1H-isoquinolin-2-yl}methanone, 1-(4-Fluorophenyl)-1-{1-[1-acetyl-spiro[2,3-dihydro-5-fluoro-1H-indol-3,4'-piperidin-1'-yl]ethyl]-5,6-difluoro-3,4-dihydro-1H-isoquinolin-2-yl}methanone, 1-Cyclopentyl-1-(1-{2-[4-(3-trifluoromethylphenyl)-piperidin-1-yl]-ethyl}-5,6-difluoro-3,4-dihydro-1H-isoquinolin-2-yl)methanone, 1-(4-Fluorophenyl)-1-(1-{2-[4-(3-trifluoromethylphenyl)-piperidin-1-yl]-ethyl}-5,6-difluoro-3,4-dihydro-1H-isoquinolin-2-yl)methanone, 1-(1-{2-[4-(6-Fluorobenzo[d]isoxazol-3-yl)-piperidin-1-yl]-ethyl}-5,6-difluoro-3,4-dihydro-1H-isoquinolin-2-yl)-1-(4-fluorophenyl)methanone, 1-(1-{2-[4-(6-Fluorobenzo[d]isoxazol-3-yl)-piperidin-1-yl]-ethyl}-5,6-difluoro-3,4-dihydro-1H-isoquinolin-2-yl)-1-(cyclopentyl)methanone, 1-(4-Fluorophenyl)-1-(1-{2-[5,6-difluorospiro[benzofuran-1(3H),4'-piperidine-1'-yl]-ethyl}-5,6-difluoro-3,4-dihydro-1-isoquinolin-2-yl)-methanone, 1-(4-Fluorophenyl)-1-({2-[6-fluorospiro[benzofuran-1(3H),4'-piperidine-1'-yl]-ethyl}-5,6-difluoro-3,4-dihydro-1H-isoquinolin-2-yl)methanone, 1-Cyclopentyl-1-(1-{2-[5,6-difluorospiro[benzofuran-1(3H),4'-piperidine-1'-yl]-ethyl}-5,6-difluoro-3,4-dihydro-1H-isoquinolin-2-yl)-methanone, and 1-Cyclopentyl-1-({2-[6-fluorospiro[benzofuran-1(3H),4'-piperidine-1'-yl]-ethyl}-5,6-difluoro-3,4-dihydro-1H-isoquinolin-2-yl)methanone.

26. A pharmaceutical composition comprising a therapeutically effective amount of a compound according to claim 1 and one or more pharmaceutically acceptable carrier or diluent.

27. A pharmaceutical preparation for the treatment of a disease of the central nervous system comprising a therapeutically effective amount of a compound according to claim 1 and one or more carrier or diluent suitable for administration to a patient in need of said treatment.

28. A method of treatment of a disease of the central nervous system comprising, administering to a patient in need of said treatment a therapeutically effective amount of a compound according to claim 1.

29. The method according to claim 28, wherein said disease of the central nervous system is selected from the group consisting of: depression, manic depression, bipolar disorder, dysthymia, mixed anxiety depression, generalised anxiety disorder, social anxiety disorder, panic anxiety disorder, post traumatic stress disorder, obsessive compulsive disorder, acute stress disorder, phobia, pre-menstrual dysphoric disorder, psychosis, Huntington's disease, Parkinson's dementia, adjustment disorders, pain, emesis, migraine, epilepsy, obesity and cerebrovascular disease.

30. The method according to claim 29, wherein said disease of the central nervous system is selected from the group consisting of depression, manic depression, bipolar disorder, dysthymia, mixed anxiety depression, generalized anxiety disorder, social anxiety disorder, panic anxiety disorder, post-traumatic stress disorder, obsessive compulsive disorder, acute stress disorder, phobia, pre-menstrual dysphoric disorder and psychosis.

31. A pharmaceutical composition comprising a therapeutically effective amount of a compound according to claim 25 and one or more pharmaceutically acceptable carrier or diluent.

32. A pharmaceutical preparation for the treatment of a disease of the central nervous system comprising a therapeutically effective amount of a compound according to claim 25 and one or more carrier or diluent suitable for administration to a patient in need of said treatment.

33. A method of treatment of a disease of the central nervous system comprising, administering to a patient in need of said treatment a therapeutically effective amount of a compound according to claim 25.

34. The method according to claim 33, wherein said disease of the central nervous system is selected from the group consisting of depression, manic depression, bipolar disorder, dysthymia, mixed anxiety depression, generalised anxiety disorder, social anxiety disorder, panic anxiety disorder, post traumatic stress disorder, obsessive compulsive disorder, acute stress disorder, phobia, pre-menstrual dysphoric disorder, psychosis, Huntington's disease, Parkinson's dementia, adjustment disorders, pain, emesis, migraine, epilepsy, obesity and cerebrovascular disease.

35. The method according to claim 34, wherein said disease of the central nervous system is selected from the group consisting of depression, manic depression, bipolar disorder, dysthymia, mixed anxiety depression, generalized anxiety disorder, social anxiety disorder, panic anxiety disorder, post-traumatic stress disorder, obsessive compulsive disorder, acute stress disorder, phobia, pre-menstrual dysphoric disorder and psychosis.

36. A compound selected from the group consisting of:

N-(4-(3-Fluoro-phenyl)-1-{2-[2-(2-methoxy-benzoyl)-1,2,3,4-tetrahydro-isoquinolin-1-yl]-ethyl}-piperidin-4-yl)acetamide, N-(4-(3-Fluoro-phenyl)-1-{2-[2-(2-methoxy-benzoyl)-1,2,3,4-tetrahydro-isoquinolin-1-yl]-ethyl}-piperidin-4-yl)acetamide, N-[1-{2-[2-(4-Chloro-benzoyl)-1,2,3,4-tetrahydro-isoquinolin-1-yl]-ethyl}-4-(3-fluoro-phenyl)-piperidin-4-yl]-acetamide, N-[1-{2-[2-(4-Bromo-benzoyl)-1,2,3,4-tetrahydro-isoquinolin-1-yl]-ethyl}-4-(3-fluoro-phenyl)-piperidin-4-yl]-acetamide, N-[1-{2-[2-(4-Fluoro-benzoyl)-1,2,3,4-tetrahydro-isoquinolin-1-yl]-ethyl}-4-(3-fluoro-phenyl)-piperidin-4-yl]-acetamide, N-(4-(3-Fluoro-phenyl)-1-{2-[2-(4-isopropyl-benzoyl)-1,2,3,4-tetrahydro-isoquinolin-1-yl]-ethyl}-piperidin-4-yl)acetamide, N-(4-(3-Fluoro-phenyl)-1-{2-[2-(4-methyl-benzoyl)-1,2,3,4-tetrahydro-isoquinolin-1-yl]-ethyl}-piperidin-4-yl)acetamide, N-[1-{2-[2-(3-Chloro-benzoyl)-1,2,3,4-tetrahydro-isoquinolin-1-yl]-ethyl}-4-(3-fluoro-phenyl)-piperidin-4-yl]-acetamide, N-[1-{2-[2-(2-Bromo-benzoyl)-1,2,3,4-tetrahydro-isoquinolin-1-yl]-ethyl}-4-(3-fluoro-phenyl)-piperidin-4-yl]-acetamide, N-(1-{2-[2-(4-Bromo-benzoyl)-1,2,3,4-tetrahydro-isoquinolin-1-yl]-ethyl}-4-phenyl-piperidin-4-yl)acetamide, N-(1-{2-[2-(2,4-Dichloro-benzoyl)-1,2,3,4-tetrahydro-isoquinolin-1-yl]-ethyl}-4-phenyl-piperidin-4-yl)acetamide,
N-[1-{2-[2-(2,4-Dichloro-benzoyl)-1,2,3,4-tetrahydro-isoquinolin-1-yl]-ethyl}-4-(3-fluoro-phenyl)-piperidin-4-yl]-acetamide,
N-[1-{2-[2-(Benzo[1,2,5]oxadiazole-5-carbonyl)-1,2,3,4-tetrahydro-isoquinolin-1-yl]-ethyl}-4-(3-fluoro-phenyl)-piperidin-4-yl]-acetamide,
N-(4-(3-Fluoro-phenyl)-1-{2-[2-(naphthalene-1-carbonyl)-1,2,3,4-tetrahydro-isoquinolin-1-yl]-ethyl}-piperidin-4-yl)acetamide,
N-[1-[2-(2-Cyclopentanecarbonyl-1,2,3,4-tetrahydro-isoquinolin-1-yl)-ethyl]-4-(3-fluoro-phenyl)-piperidin-4-yl]-acetamide,
N-(1-{2-[2-(4-Chloro-benzoyl)-1,2,3,4-tetrahydro-isoquinolin-1-yl]-ethyl}-4-phenyl-piperidin-4-yl)acetamide,
N-[1-{2-[2-(Benzo[b]thiophene-3-carbonyl)-1,2,3,4-tetrahydro-isoquinolin-1-yl]-ethyl}-4-(3-fluoro-phenyl)-piperidin-4-yl]-acetamide,
N-[1-{2-[2-(6-Fluoro-4H-benzo[1,3]dioxine-8-carbonyl)-1,2,3,4-tetrahydro-isoquinolin-1-yl]-ethyl}-4-(3-fluoro-phenyl)-piperidin-4-yl]acetamide,
N-[1-{2-[2-(3-Bromo-benzoyl)-1,2,3,4-tetrahydro-isoquinolin-1-yl]-ethyl}-4-(3-fluoro-phenyl)-piperidin-4-yl]acetamide,
N-[1-{2-[2-(2-Fluoro-benzoyl)-1,2,3,4-tetrahydro-isoquinolin-1-yl]-ethyl}-4-(3-fluoro-phenyl)-piperidin-4-yl]acetamide,
N-(1-{2-[2-(4-Methyl-benzoyl)-1,2,3,4-tetrahydro-isoquinolin-1-yl]-ethyl}-4-phenyl-piperidin-4-yl)acetamide,
N-[1-{2-[2-(2-Chloro-benzoyl)-1,2,3,4-tetrahydro-isoquinolin-1-yl]-ethyl}-4-(3-fluoro-phenyl)-piperidin-4-yl]-acetamide,
N-(4-(3-Fluoro-phenyl)-1-{2-[2-(4-methoxy-benzoyl)-1,2,3,4-tetrahydro-isoquinolin-1-yl]-ethyl}-piperidin-4-yl)acetamide,
N-(1-{2-[2-(3-Chloro-benzoyl)-1,2,3,4-tetrahydro-isoquinolin-1-yl]-ethyl}-4-phenyl-piperidin-4-yl)acetamide,
N-(1-{2-[2-(4-Fluoro-benzoyl)-1,2,3,4-tetrahydro-isoquinolin-1-yl]-ethyl}-4-phenyl-piperidin-4-yl)acetamide,
N-{1-[2-(2-Cycloheptanecarbonyl-1,2,3,4-tetrahydro-isoquinolin-1-yl)-ethyl]-4-phenyl-piperidin-4-yl}-acetamide,
N-(1-{2-[2-(3-Bromo-benzoyl)-1,2,3,4-tetrahydro-isoquinolin-1-yl]-ethyl}-4-phenyl-piperidin-4-yl)acetamide,
N-(4-(3-Fluoro-phenyl)-1-{2-[2-(3-methoxy-benzoyl)-1,2,3,4-tetrahydro-isoquinolin-1-yl]-ethyl}-piperidin-4-yl)acetamide,
N-(4-(3-Fluoro-phenyl)-1-{2-[2-(thiophene-3-carbonyl)-1,2,3,4-tetrahydro-isoquinolin-1-yl]-ethyl}-piperidin-4-yl)acetamide,
N-(4-(3-Fluoro-phenyl)-1-{2-[2-(4-pyrazol-1-yl-benzoyl)-1,2,3,4-tetrahydro-isoquinolin-1-yl]-ethyl}-piperidin-4-yl)acetamide,
N-(1-{2-[2-(Naphthalene-1-carbonyl)-1,2,3,4-tetrahydro-isoquinolin-1-yl]-ethyl}-4-phenyl-piperidin-4-yl)acetamide;

wherein the compound is prepared by acylating an enantiomeric amine of formula V:

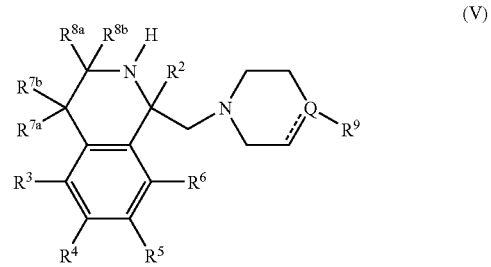

wherein:

$R^2$ is hydrogen, trifluoromethyl or $C_{1-6}$-alkyl;

$R^3$-$R^6$, $R^{7a}$, $R^{7b}$, $R^{8a}$ and $R^{8b}$ each are independently hydrogen, halogen, cyano, nitro, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, amino, $C_{1-6}$-alkylamino, di-($C_{1-6}$-alkyl)amino, $C_{1-6}$-alkylcarbonyl, aminocarbonyl, $C_{1-6}$-alkylaminocarbonyl, di-($C_{1-6}$-alkyl)aminocarbonyl, $C_{1-6}$-alkoxy, $C_{1-6}$-alkylthio, hydroxy, trifluoromethyl, trifluoromethylsulfonyl or $C_{1-6}$-alkylsulfonyl;

$R^9$ is benzyl, benzoyl, 2,3-dihydrobenzofuranyl, mono- or bicyclic aryl, or heteroaryl wherein each benzyl, benzoyl, aryl or heteroaryl optionally is substituted with one or more substituents selected from halogen, cyano, nitro, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, amino, $C_{1-6}$-alkylamino, di-($C_{1-6}$-alkyl)amino, $C_{1-6}$-alkylcarbonyl, aminocarbonyl, $C_{1-6}$-alkylaminocarbonyl, di-($C_{1-6}$-alkyl)aminocarbonyl, $C_{1-6}$-alkoxy, $C_{1-6}$-alkylthio, hydroxy, trifluoromethyl, difluoromethyl, fluoromethyl and trifluoromethylsulfonyl;

Q is C, N or $CR^{10}$;

wherein $R^{10}$ is hydrogen, halogen, cyano, nitro, $C_{1-6}$-alkyl, $C_{2-6}$-alkenyl, $C_{2-6}$-alkynyl, $C_{3-8}$-cycloalkyl, $C_{3-8}$-cycloalkyl-$C_{1-6}$-alkyl, amino, $C_{1-6}$-alkylamino, di-($C_{1-6}$-alkyl)amino, $C_{1-6}$-alkylcarbonyl, aminocarbonyl, $C_{1-6}$-alkylaminocarbonyl, di-($C_{1-6}$-alkyl)aminocarbonyl, $C_{1-6}$-alkoxy, $C_{1-6}$-alkylthio, hydroxy, trifluoromethyl, difluoromethyl, fluoromethyl, trifluoromethylsulfonyl, —$NR^{30}COR^{31}$ wherein $R^{30}$ is hydrogen or $C_{1-6}$-alkyl and $R^{31}$ is $C_{1-6}$-alkyl, —$COOR^{16}$ wherein $R^{16}$ is hydrogen or $C_{1-6}$-alkyl, or —$CONR^{17}R^{18}$ wherein $R^{17}$ and $R^{18}$ each are independently are selected from hydrogen or $C_{1-6}$-alkyl or $R^{17}$ and $R^{18}$, taken together with the nitrogen to which they are attached, form a piperidinyl, piperazinyl or morpholinyl group, wherein said piperidinyl, piperazinyl and morpholinyl group is unsubstituted or substituted with a $C_{1-6}$-alkyl;

or when Q is $CR^{10}$, $R^9$ and $R^{10}$, taken together with a carbon to which they are attached, form a cyclic structure selected from the group consisting of:

1)

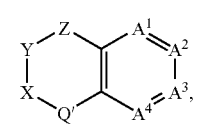

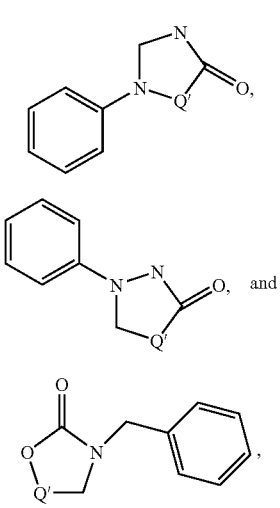

wherein Q' is a carbon shared with a piperidine ring, whereby said cyclic structure together with said piperidine ring forms a spiro structure; and X, Y, and Z each are independently O, NR$^{19}$, CR$^{23}$R$^{24}$, S(O)$_n$ or a bond, wherein: R$^{19}$ is hydrogen, C$_{1-6}$-alkyl, C$_{2-6}$-alkenyl, C$_{2-6}$-alkynyl, C$_{3-8}$-cycloalkyl, C$_{3-8}$cycloalkyl-C$_{1-6}$-alkyl, trifluoromethyl, acyl, thioacyl or trifluoromethylsulfonyl; R$^{19}$ is R$^{20}$SO$_2$—, R$^{20}$OCO— or R$^{20}$SCO— wherein R$^{20}$ is C$_{1-6}$-alkyl, C$_{2-6}$-alkenyl, C$_{2-6}$-alkynyl, C$_{3-8}$-cycloalkyl, C$_{3-8}$-cycloalkyl-C$_{1-6}$-alkyl or aryl; or R$^{19}$ is R$^{21}$R$^{22}$NCO— or R$^{21}$R$^{22}$NCS—, wherein R$^{21}$ and R$^{22}$ each are independently hydrogen, C$_{1-6}$-alkyl, C$_{2-6}$-alkenyl, C$_{2-6}$-alkynyl, C$_{3-8}$-cycloalkyl, C$_{3-8}$-cycloalkyl-C$_{1-6}$-alkyl, or aryl, wherein said aryl is unsubstituted or substituted with one or more substituents selected from C$_{1-6}$-alkyl or halogen; or R$^{21}$ and R$^{22}$, taken together with the N-atom to which they are linked, form a pyrrolidinyl, piperidinyl or perhydroazepinyl group; and R$^{23}$ and R$^{24}$ each are independently hydrogen, halogen, cyano, nitro, C$_{1-6}$-alkyl, C$_{2-6}$-alkenyl, C$_{2-6}$-alkynyl, C$_{3-8}$-cycloalkyl, C$_{3-8}$-cycloalkyl-C$_{1-6}$-alkyl, aryl or heteroaryl, wherein said aryl is unsubstituted or substituted with one or more substituents selected from C$_{1-6}$-alkyl, halogen, amino, C$_{1-6}$-alkylamino, or NR$^{25}$R$^{26}$, wherein R$^{25}$ and R$^{26}$ each are independently C$_{1-6}$-alkyl, C$_{1-6}$-alkylcarbonyl, aminocarbonyl, C$_{1-6}$-alkylaminocarbonyl, di-(C$_{1-6}$-alkyl)aminocarbonyl, C$_{1-6}$-alkoxy, C$_{1-6}$-alkylthio, hydroxy, trifluoromethyl, trifluoromethylsulfonyl or C$_{1-6}$-alkylsulfonyl; or R$^{25}$ and R$^{26}$, taken together, with the N-atom to which they are linked, form a pyrrolidinyl, piperidinyl, perhydroazepinyl or morpholinyl group; or R$^{23}$ and R$^{24}$, taken together form an oxo group; and n is 0, 1 or 2; provided that no more than one of X, Y and Z may be a bond, and provided that two adjacent X, Y or Z may not at the same time be O and S; and A$^1$, A$^2$, A$^3$ and A$^4$ each are independently N or CR$^{27}$, wherein R$^{27}$ is hydrogen, halogen, cyano, nitro, C$_{1-6}$-alkyl, C$_{2-6}$-alkenyl, C$_{2-6}$-alkynyl, C$_{3-8}$-cycloalkyl, C$_{3-8}$-cycloalkyl-C$_{1-6}$-alkyl, C$_{1-6}$-alkylcarbonyl, aminocarbonyl, C$_{1-6}$-alkylaminocarbonyl, di-(C$_{1-6}$-alkyl)aminocarbonyl, C$_{1-6}$-alkoxy, C$_{1-6}$-alkylthio, hydroxy, trifluoromethyl, difluoromethyl, fluoromethyl, trifluoromethylsulfonyl, C$_{1-6}$-alkylsulfonyl, amino, or NR$^{28}$R$^{29}$, wherein R$^{28}$ and R$^{29}$ each are independently hydrogen or C$_{1-6}$-alkyl; or R$^{28}$ and R$^{29}$, taken together with the N-atom to which they are linked, form a pyrrolidinyl, piperidinyl, perhydroazepinyl or morpholinyl group; provided that only one of A$^1$, A$^2$, A$^3$ and A$^4$ may be N; and provided that a dotted line emanating from Q is a bond when Q is C, and no bond when Q is CR$^{10}$ or N; and wherein the enantiomeric amine of formula V is the slower eluting enantiomer of a pair of enantiomeric amines of formula V when the pair is separated by supercritical HPLC at 20 Mpa on a system comprising at least one chiralcel OD column and an eluent comprising carbondioxide (75%), 2-propanol (24.75%), diethylamine (0.125%) and trifluoracetic acid (0.125%).

* * * * *